United States Patent
Radermacher et al.

(10) Patent No.: US 11,229,519 B2
(45) Date of Patent: Jan. 25, 2022

(54) KINEMATIC AND PARAMETERIZED MODELING FOR PATIENT-ADAPTED IMPLANTS, TOOLS, AND SURGICAL PROCEDURES

(71) Applicant: ConforMIS, Inc., Billerica, MA (US)

(72) Inventors: Klaus Radermacher, Aachen (DE); Daniel Steines, Lexington, MA (US)

(*) Notice: Subject to any disclaimer, the term of this patent is extended or adjusted under 35 U.S.C. 154(b) by 0 days.

(21) Appl. No.: 16/822,865

(22) Filed: Mar. 18, 2020

(65) Prior Publication Data

US 2020/0214843 A1    Jul. 9, 2020

Related U.S. Application Data

(63) Continuation of application No. 15/956,378, filed on Apr. 18, 2018, now abandoned, which is a (Continued)

(51) Int. Cl.
G05B 19/4099    (2006.01)
A61F 2/30    (2006.01)
(Continued)

(52) U.S. Cl.
CPC .......... A61F 2/30942 (2013.01); A61B 17/15 (2013.01); A61B 34/10 (2016.02); G05B 19/4099 (2013.01); *A61B 2017/00526* (2013.01); *A61B 2034/105* (2016.02); *A61B 2034/108* (2016.02); *A61B 2034/2051* (2016.02); *A61B 2034/2055* (2016.02); *A61F 2002/30943* (2013.01); *A61F 2002/30948* (2013.01); *A61F 2002/30955* (2013.01);
(Continued)

(58) Field of Classification Search
CPC ...... G05B 19/4099; G05B 2219/35134; A61F 2/30942; A61F 2002/30948; A61F 2002/30955; A61B 34/10; A61B 17/15; A61B 2017/00526
See application file for complete search history.

(56) References Cited

U.S. PATENT DOCUMENTS

| 5,768,134 A | 6/1998 | Swaelens et al. |
| 6,932,842 B1 | 8/2005 | Litschko et al. |

(Continued)

FOREIGN PATENT DOCUMENTS

| JP | 2001502565 | 2/2001 |
| JP | 200285435 | 3/2002 |

(Continued)

OTHER PUBLICATIONS

"Amendment to Office Action dated Dec. 5, 2018 pertaining to U.S. Appl. No. 15/953,378, 8 pages".

(Continued)

*Primary Examiner* — Gary Collins
(74) *Attorney, Agent, or Firm* — Sunstein LLP

(57) ABSTRACT

Patient-adapted articular repair systems, including implants, instruments, and surgical plans, and methods of making and using such systems, are disclosed herein. In particular, various embodiments include methods of selecting and/or designing patient-adapted surgical repair systems using parameterized models and/or multibody simulations.

8 Claims, 19 Drawing Sheets

Related U.S. Application Data continuation of application No. 14/775,190, filed as application No. PCT/US2014/030001 on Mar. 15, 2014, now abandoned.

(60) Provisional application No. 61/801,865, filed on Mar. 15, 2013.

(51) Int. Cl.
*A61B 17/15* (2006.01)
*A61B 34/10* (2016.01)
*A61B 17/00* (2006.01)
*A61B 34/20* (2016.01)

(52) U.S. Cl.
CPC ............... *A61F 2240/001* (2013.01); *G05B 2219/35134* (2013.01)

(56) References Cited

U.S. PATENT DOCUMENTS

| | | | |
|---|---|---|---|
| 7,587,075 | B1 | 9/2009 | Stefan et al. |
| 8,406,908 | B2 | 3/2013 | Moenkmeyer |
| 2005/0197814 | A1 | 9/2005 | Aram et al. |
| 2006/0063135 | A1 | 3/2006 | Mehl |
| 2006/0094951 | A1 | 5/2006 | Dean et al. |
| 2008/0319448 | A1* | 12/2008 | Lavallee .............. G16H 50/50 606/102 |
| 2009/0325128 | A1 | 12/2009 | Holzner et al. |
| 2010/0274534 | A1 | 10/2010 | Steines et al. |
| 2010/0292963 | A1 | 11/2010 | Schroeder |
| 2011/0029093 | A1 | 2/2011 | Bojarski et al. |
| 2011/0087465 | A1* | 4/2011 | Mahfouz ............... G06T 7/35 703/1 |
| 2011/0112808 | A1 | 5/2011 | Anderson et al. |
| 2012/0209394 | A1 | 8/2012 | Bojarski et al. |
| 2013/0211242 | A1 | 8/2013 | Bertrand et al. |

FOREIGN PATENT DOCUMENTS

| | | |
|---|---|---|
| WO | WO-9814128 A1 | 4/1998 |
| WO | WO-0059411 A1 | 10/2000 |
| WO | WO-0166021 A1 | 9/2001 |
| WO | WO-2014145267 A1 | 9/2014 |

OTHER PUBLICATIONS

"European Office Action pertaining to EP Application No. 14765606.0 dated Aug. 11, 2020, 10 pages".
"Extended European Search Report, Application No. 14765606.0 dated Oct. 10, 2016, 5 pages".
International Search Report—International Application No. PCT/US2014/030001 dated Aug. 27, 2014, together with the Written Opinion of the International Searching Authority, 10 pages.
"Office Action dated Oct. 18, 2017, pertaining to U.S. Appl. No. 14/775,190, 11 pages".
"Office Action pertaining to U.S. Appl. No. 15/956,378 dated Decembers, 2018, 7 pages".
"Office Action pertaining to U.S. Appl. No. 15/956,378 dated Sep. 18, 2019, 7 pages".
"Office Action pertaining to JP Application No. 2012-109834, dated Jun. 24, 2016, English translation attached, 11 pages".

\* cited by examiner

KINEMATIC AND PARAMETERIZED MODELING FOR PATIENT-ADAPTED IMPLANTS, TOOLS, AND SURGICAL PROCEDURES

RELATED APPLICATIONS

This application is a continuation of U.S. application Ser. No. 15/956,378, entitled "Kinematic and Parameterized Modeling for Patient-Adapted Implants, Tools, and Surgical Procedures," filed Apr. 18, 2018, which in turn is a continuation of U.S. application Ser. No. 14/775,190, entitled "Kinematic and Parameterized Modeling for Patient-Adapted Implants, Tools, and Surgical Procedures," filed Sep. 11, 2015, which in turn is a U.S. national state entry under 35 USC § 371 of PCT/US14/30001, entitled "Kinematic and Parameterized Modeling for Patient-Adapted Implants, Tools, and Surgical Procedures," filed Mar. 15, 2014, which in turn claims the benefit of U.S. Provisional Application No. 61/801,865, entitled "Modeling, Analyzing And Using Anatomical Data For Patient-Adapted Implants, Designs, Tools And Surgical Procedures" and filed Mar. 15, 2013. Each of the above-described applications is hereby incorporated herein by reference in its entirety.

TECHNICAL FIELD

This application relates to improved methods of modeling, designing and selecting patient-adapted (e.g., patient-specific and/or patient-engineered) implant designs, including the use of novel kinematic modeling systems and techniques in the design, manufacture, testing and surgical planning for joint replacement procedures.

BACKGROUND AND SUMMARY

Recently, the joint repair and replacement field has come to embrace the concept of "patient-specific" and "patient-engineered" implant systems. With such systems, the surgical implants and associated surgical tools and procedures are designed or otherwise modified to account for and accommodate one or more features of the individual anatomy of the patient undergoing the surgical procedure. Such systems typically utilize non-invasive imaging data, taken of the individual pre-operatively, to guide the design and/or selection of the implant, surgical tools, and the planning of the surgical procedure itself. Various objectives of these newer systems include: (1) reducing the amount of bony anatomy removed to accommodate the implant, (2) designing/selecting an implant that replicates and/or improves the function of the natural joint, (3) increasing the durability and functional lifetime of the implant, (4) simplifying the surgical procedure for the surgeon, (5) reducing patient recovery time and/or discomfort, and (6) improving patient outcomes.

Advantages of the various embodiments described herein can include better fit, more natural movement of the joint, reduction in the amount of bone removed during surgery and less invasive surgical procedures. If desired, patient-adapted articular implants can be selected, designed and/or created from images of the patient's joint and/or other anatomical structures. Based on the images, patient-adapted implant components can be selected and/or designed to include features (e.g., surface contours, curvatures, widths, lengths, thicknesses, and other features) that match existing features in the single, individual patient's joint as well as features that approximate an ideal and/or healthy feature that may not exist in the patient prior to a procedure. Moreover, by altering the design and/or selection approach to address various potential and actual implant design issues, non-traditional design approaches have been identified that offer improvements over traditional implant designs and surgical procedures.

Patient-adapted features can include patient-specific features as well as patient-engineered features. Patient-specific (or patient-matched) implant component or guide tool features can include features adapted, designed, modified and/or manufactured to match or substantially match one or more of the patient's biological features, for example, one or more biological/anatomical structures, alignments, kinematics, and/or soft tissue features. Patient-engineered (or patient-derived) features of an implant component can include features adapted, designed, modified and/or manufactured (e.g., preoperatively designed and manufactured) based at least partially on patient-specific data in combination with various other data sources and/or various engineering and design principles to substantially enhance or improve one or more of the patient's anatomical and/or biological features.

In various exemplary embodiments described herein, the design, selection, manufacture, testing and surgical planning associated with patient-specific implant designs can be further improved or refined by various combinations of soft tissue and/or kinematic modeling methods, techniques and considerations. Such approaches represent a quantum leap in the development of joint replacement implants and associated surgical procedures.

In various embodiments, the techniques, methods, implant components, tools and surgical procedures described can be can be applied to any joint, including, without limitation, a spine, spinal articulations, an intervertebral disk, a facet joint, a shoulder, an elbow, a wrist, a hand, a finger, a hip, a knee, an ankle, a foot, or a toe joint. Moreover, the implant components can be selected and/or designed to accommodate any number and/or shape of prepared anatomical support surfaces, including accommodating no prepared surfaces (i.e., attaching to and/or abutting against the pre-existing surfaces of the patient's articular anatomy).

It is to be understood that the features of the various embodiments described herein are not mutually exclusive and may exist in various combinations and permutations.

BRIEF DESCRIPTION OF THE DRAWINGS

The foregoing and other objects, aspects, features, and advantages of embodiments will become more apparent and may be better understood by referring to the following description, taken in conjunction with the accompanying drawings, in which.

HEADINGS

Figure 1:
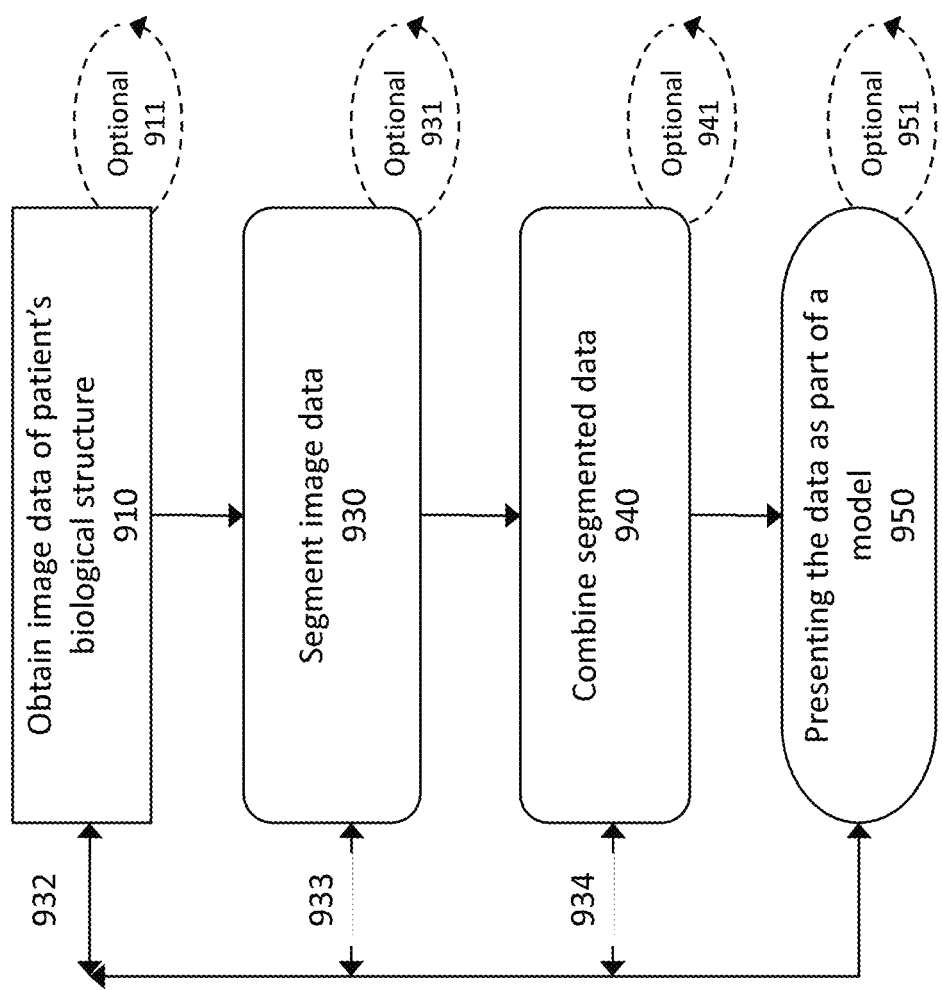
FIG. 1 is a flow chart illustrating a process for generating a model of a patient's joint (and/or a resection cut, guide tool, and/or implant component)

The headings used herein are for convenience only. The headings do not purport to define, limit, or extend the scope or intent of the language of the sections and/or the paragraphs to which they pertain.

INCORPORATION BY REFERENCE

The entire disclosure of each of the publications, patent documents, and other references referred to herein is incorporated herein by reference in its entirety for all purposes to the same extent as if each individual source were individually denoted as being incorporated by reference.

DETAILED DESCRIPTION

Imaging, Computer Modeling and Software

Pre-operative imaging of patient anatomy is constantly improving in accuracy, sensitivity and availability, and the use of such imaging techniques continues to expand and become commonplace. Concurrently, the availability and capabilities of automated and/or semi-automated computing systems have significantly increased, while the cost of such systems has reduced. This convergence creates a significant opportunity for orthopedic implant designers and manufacturers to improve the durability and/or performance of their implants as well as simplify and diversify the surgical implantation procedures associated with such devices.

Various embodiments described herein include the use of automated and/or semi-automated computing systems to obtain, quantify, classify and/or model patient anatomical image data for use in selecting and/or designing surgical tools, implants and/or surgical procedures to repair and/or replace portions of a patient's anatomy. The models created can include actual and/or approximate models of the patient's existing anatomy as well as models of optimal, desired, undesired and/or unacceptable anatomy derived using, at least in part, the patient's existing anatomical data. The derived models can be created using a wide variety of tools, techniques and/or data sources.

The image data, derived models and/or actual models can be utilized to select, design and/or manufacture surgical tools, implants and surgical techniques that, when utilized on the patient, create an optimal and/or otherwise acceptable repair and/or replacement of the relevant patient anatomy. These models will also desirably facilitate the creation of highly durable implant components that can be easily implanted using less invasive and/or least invasive surgical techniques. Various embodiments will desirably increase the availability, performance, convenience, suitability and/or cost of orthopedic implants.

An initial step in repairing and/or replacing one or more anatomical features of a patient is to assess the size, shape and/or condition of the relevant patient anatomy. For an orthopedic implant, this process typically includes obtaining one or more images of the patient's joint and/or other relevant patient anatomy (e.g., adjacent anatomical areas and/or other features of interest) using, for example, non-invasive imaging modalities (as well as other imaging and/or anatomical derivation techniques known in the art). The raw electronic image data can be used to create one or more representations or "models" of the patient's anatomy. These representations can include electronic models as well as 2-Dimensional images and/or 3-Dimensional physical reproductions of the patient anatomy.

In various embodiments, the models can be used to select and/or design an orthopedic implant appropriate for the patient's anatomy. In other embodiments, the models can be processed and/or modified to generate one or more modified versions of the patient anatomy, including portions of a joint and/or surfaces within or adjacent to the joint, with the derived model(s) representing desired (and/or undesired) conditions of the joint at various stages, including after surgical repair and/or replacement. In various embodiments, the raw image data can be used to create models that can be used to analyze the patient's existing joint structure and kinematics, and to devise and evaluate a course of corrective action.

If desired, the data and/or models can be used to design an implant that replaces the existing component having one or more patient-specific features, such as a surface or curvature. In alternative embodiments, the various models described herein can be utilized to plan a surgical procedure as well as to design and/or select surgical tools useful during the procedure. In various embodiments, the models can be optimized or otherwise modified using a wide variety of techniques and/or data sources, to create one or more desired models that represent one or more desired "improvements" or outcomes of a surgical repair and/or replacement.

Obtaining and Modeling Data

One initial step in many embodiments is to obtain image data of a patient's anatomy. As illustrated in FIG. 1, a method of generating a model of a patient's joint or other biological feature can include one or more of the steps of obtaining image data of a patient's biological structure 910; analyzing or segmenting the image data 930; combining the segmented data 940; and presenting the data as part of a model 950.

Image data can be obtained 910 from near or within the patient's biological structure(s) of interest. For example, pixel or voxel data from one or more radiographic or tomographic images of a patient's joint can be obtained, for example, using computed or magnetic resonance tomography. A wide variety of imaging modalities known in the art can be used, including X-ray, ultrasound, laser imaging, MRI, PET, SPECT, radiography including digital radiography, digital tomosynthesis, cone beam CT, and contrast enhanced imaging. Image data can also include electronic image data derived from physical image "films" or "plates" through scanning or other capture techniques.

The one or more pixels or voxels (as well as other electronic values representing the image data) can be converted into one or a set of values. For example, a single pixel/voxel or a group of pixels/voxels can be converted to coordinate values, e.g., a point in a 2D or 3D coordinate system. The set of values also can include a value corresponding to the pixel/voxel intensity or relative grayscale color. Moreover, the set of values can include information about neighboring pixels or voxels, for example, information corresponding to relative intensity or grayscale color and or information corresponding to relative position.

Figure 2B:
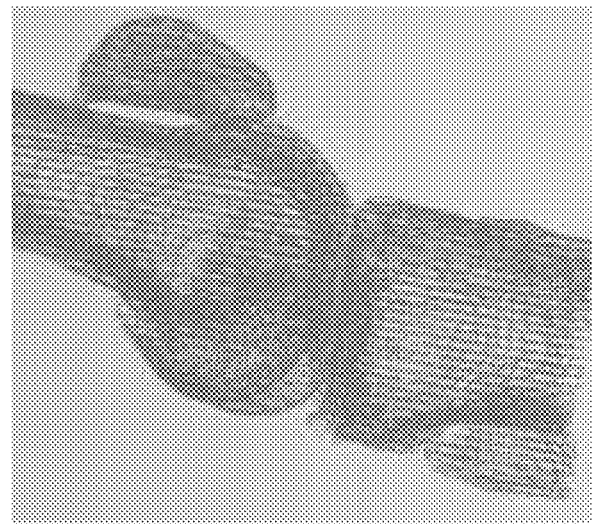
FIGS. 2A and 2B are front and side views of a surface outline for a patient's femur and tibia.
Figure 2A:
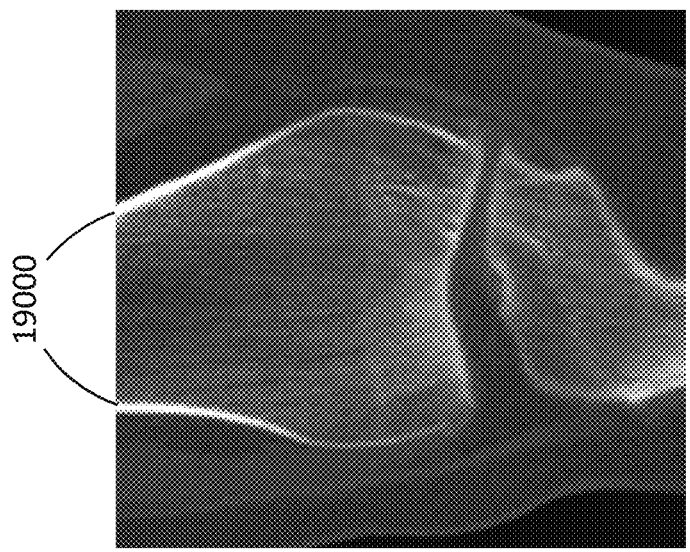

Then, the image data can be analyzed or segmented 930 to identify those data corresponding to a particular biological feature of interest. For example, as shown in FIG. 2A, image data can be used to identify the edges of a biological structure, in this case, the surface outline for each of the patient's femur and tibia. As shown, the distinctive transition in color intensity or grayscale 19000 at the surface of the structure can be used to identify pixels, voxels, corresponding data points, a continuous line, and/or surface data representing the surface or other feature of the biological structure. This step can be performed automatically (for example, by a computer program operator function) or manually (for example, by a clinician or technician), or by a combination of the two.

Optionally, the segmented data can be combined 940. For example, in a single image, segmented and selected reference points (e.g., derived from pixels or voxels) and/or other data can be combined to create one or more lines representing the surface outline of a biological structure. Moreover, as shown in FIG. 2B, the segmented and selected data from multiple images can be combined to create a 3D representation of the biological structure. Alternatively, the images can be combined to form a 3D data set, from which the 3D representation of the biological structure can be derived directly using a 3D segmentation technique, for example an active surface or active shape model algorithm or other model based or surface fitting algorithm.

Optionally, the 3D representation of the biological structure can be generated, manipulated, smoothed and/or corrected, for example, by employing a 3D polygon surface, a subdivision surface or parametric surface such as, for example, a non-uniform rational B-spline (NURBS) surface. For a description of various parametric surface representations see, for example Foley, J. D. et al., Computer Graphics: Principles and Practice in C; Addison-Wesley, 2nd edition (1995). Various methods are available for creating a parametric surface. In various embodiments, the 3D representation can be converted directly into a parametric surface by connecting data points to create a surface of polygons and applying rules for polygon curvatures, surface curvatures, and other features. Alternatively, a parametric surface can be best-fit to the 3D representation, for example, using publicly available software such as Geomagic® software (Research Triangle Park, N.C.).

Then, the data can be presented as part of a model 950, for example, a patient-specific virtual model that includes the biological feature(s) of interest. The data can be utilized to create multiple models, representing different anatomical features (i.e., individual models representing bone surfaces, bone structure variations or interfaces, articulating surfaces, muscles and/or connective tissues, the patient's skin surface, etc.) or a single model can incorporate multiple features of interest.

As will be appreciated by those of skill in the art, one or more of these steps 910, 930, 940, 950 can be repeated 911, 931, 941, 951 as often as desired to achieve the desired result. Moreover, the steps can be repeated reiteratively 932, 933, 934. If desired, the practitioner can proceed directly 933 from the step of segmenting image data 930 to presenting the data as part of a model 950.

Deformable Segmentation and Models

In various embodiments, individual images of a patient's biological structure can be segmented individually and then, in a later step, the segmentation data from each image can be combined. The images that are segmented individually can be one of a series of images, for example, a series of coronal tomographic slices (e.g., front to back) and/or a series of sagittal tomographic slices (e.g., side to side) and/or a series of axial tomographic slices (e.g., top to bottom) of the patient's joint. In some cases, segmenting each image individually can create noise in the combined segmented data. As an illustrative example, in an independent segmentation process, an alteration in the segmentation of a single image may not alter the segmentation in contiguous images in a series. Accordingly, an individual image can be segmented to show data that appears discontinuous with data from contiguous images. To address this issue, certain embodiments include methods for generating a model from a collection of images, for example, simultaneously, rather than from individually segmented images. One such method is referred to as deformable segmentation.

In the deformable segmentation method, a template model having a surface data representation, such as for example a parametric surface, a subdivision surface or a meshed surface, can be deformed to fit a collection of multiple images. By fitting the template model to a collection of images, alterations to one location in the template model can be carried across the model and, therefore, connect information corresponding to various images in the collection, thus preserving continuity and smoothness of the surface model. For example, in certain embodiments, a template model includes a parametric surface that includes multiple patches or sections. During deformation, the patches can maintain a set of properties, such as continuity, curvature, and/or other properties within each patch and/or across patch boundaries with neighboring patches. These properties also can be reinforced during deformation so that the integrity of the model is maintained.

Figure 3:
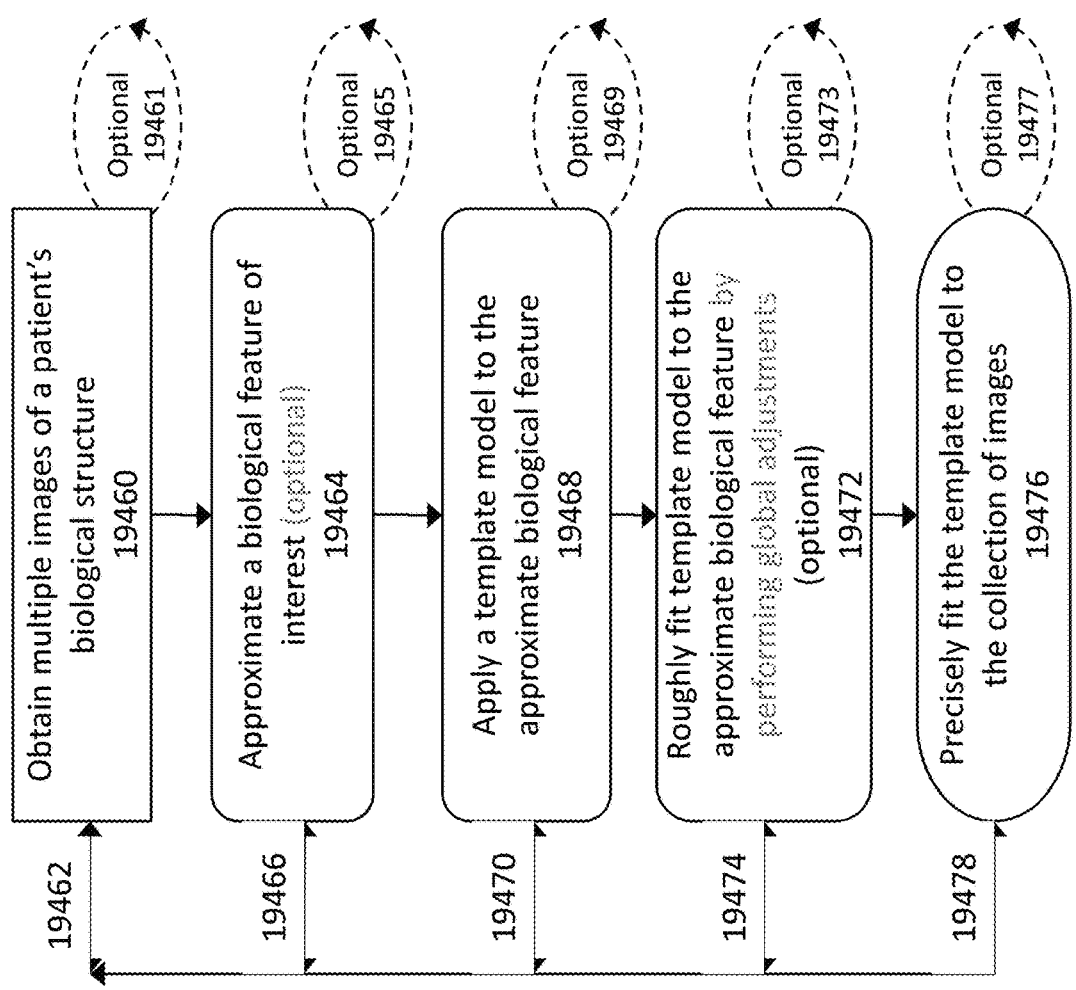
FIG. 3 depicts a flowchart of steps in certain embodiments of a deformable segmentation method.

FIG. 3 shows a flowchart of steps in certain embodiments of a deformable segmentation method. The steps include one or more of collecting multiple images of a patient's biological structure 19460; optionally approximating a biological feature of interest 19464; applying a template model to the approximate biological feature of interest 19468; optionally roughly fitting the template model to the approximate biological feature 19472 (e.g., by performing global adjustments); and precisely fitting the template model to the collection of multiple images 19476. Similar to other methods described herein, one or more of these steps 19460, 19464, 19468, 19472, 19476 can be repeated 19461, 19465, 19469, 19473, 19477 as often as desired to achieve the desired result. Moreover, the steps can be repeated reiteratively 19462, 19466, 19470, 19474, 19478. FIGS. 4A-40 show exemplary images from a computer program that applies an embodiment of the deformable segmentation method.

Figure 4A:
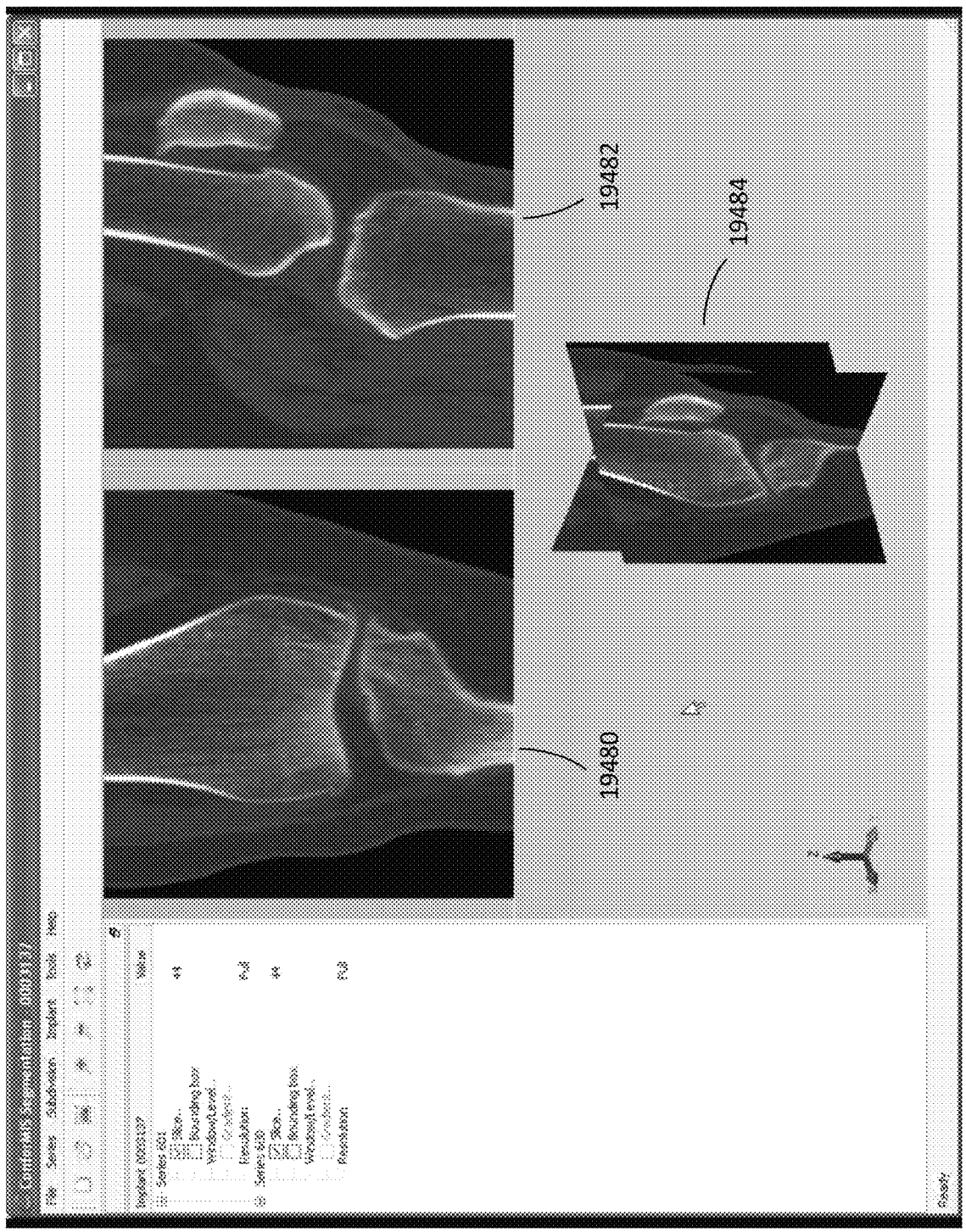
FIGS. 4A through 4I depict various views of a display interface for one embodiment of a computer program that applies a deformable segmentation method.

In one step 19460, multiple images can be collected for processing together, for example, the images can be processed together in a single event rather than individually. As illustrated in FIG. 4A, a computer program can be used to load and view the multiple images as one or more views into one or more 3D image data stacks, for example coronal, sagittal or axial views. In the figure, a series of coronal image slices 19480 and a series of sagittal image slices 19482 can be viewed as separate stacks or decks of 2D images. These stacks of images can result from separate image scans or can be different views of the same scan. In addition, any two or more images can be combined 19484 to provide a 3D image.

Figure 4B:
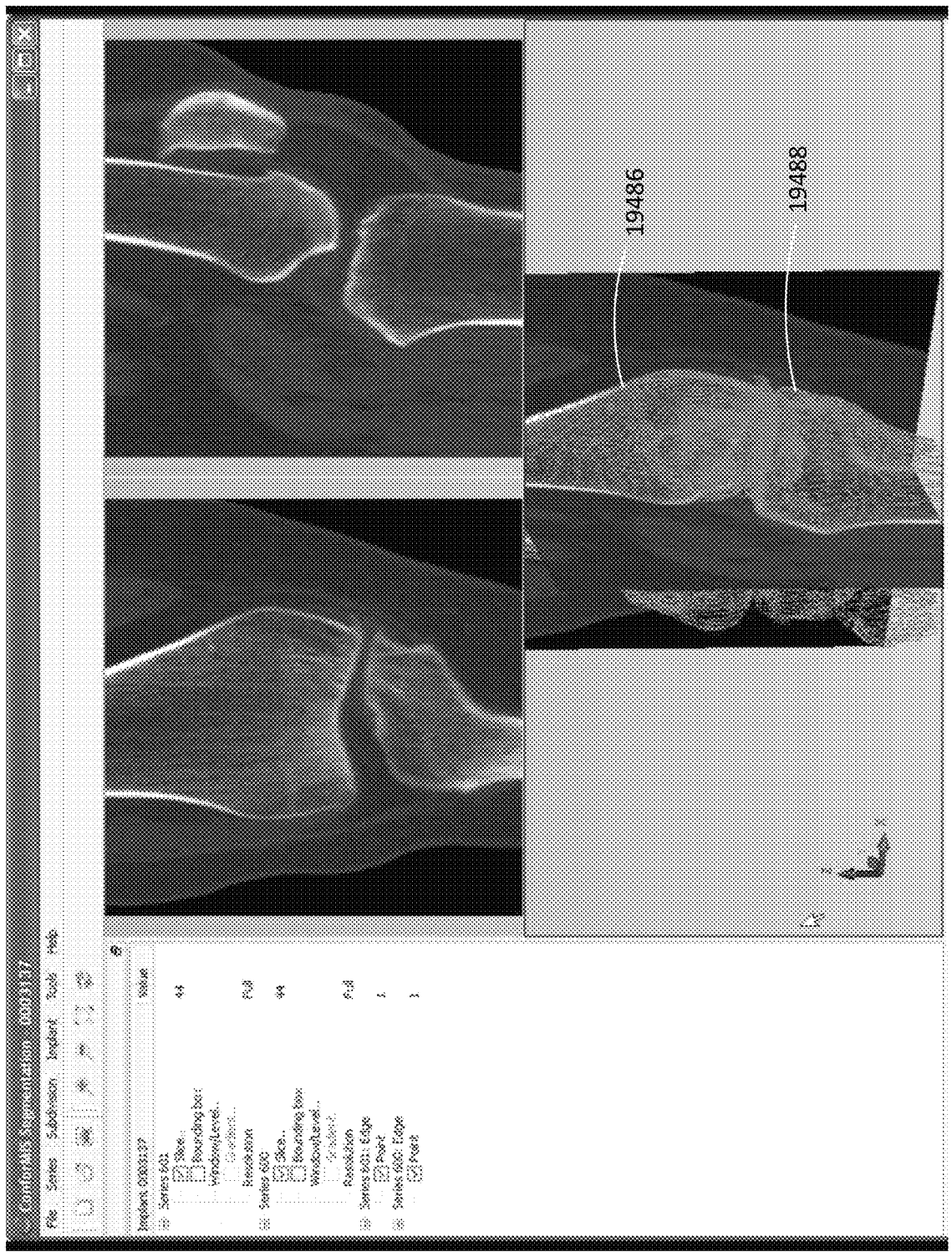

In another step 19464, a biological feature of interest is approximated from the multiple images. FIG. 4B illustrates the approximated biological features of a femoral surface 19486 and a tibial surface 19488. The approximated surface can be provided by the method described above, for example, by detecting edges in each image based on relative grayscale or intensity changes, and then combining the image data. In various embodiments, this step can be optional.

Figure 4C:
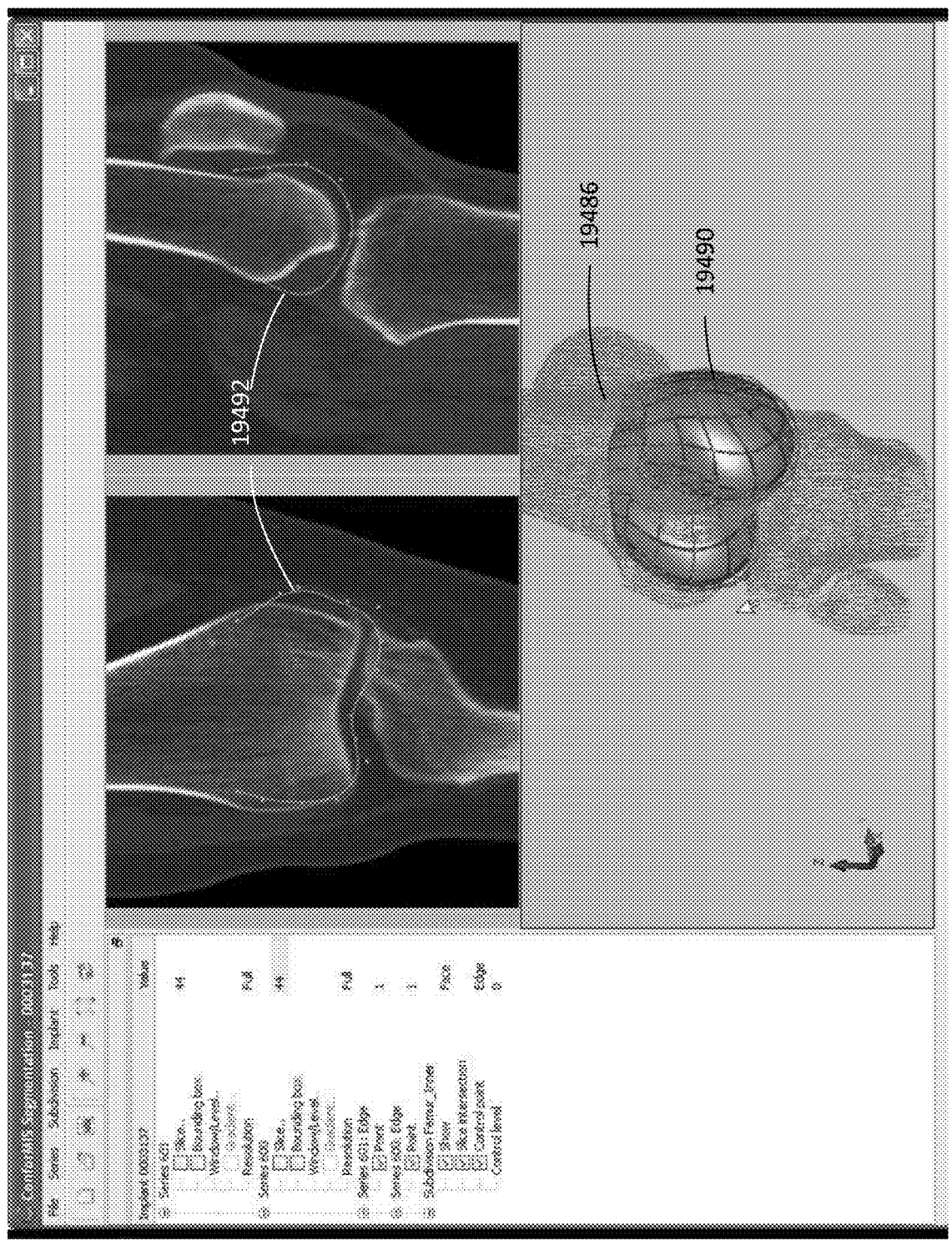

In another step 19468, a template model is applied to the approximate biological feature or directly to the combined image data stack. FIG. 4C illustrates a femoral template model 19490 applied to the approximate femoral surface 19486. In applying a template model, the operator or user of the software can select one or more initial best fit template models. Template models can be available from a library of models, for example, collected from one or more previous assessments.

Figure 4D:
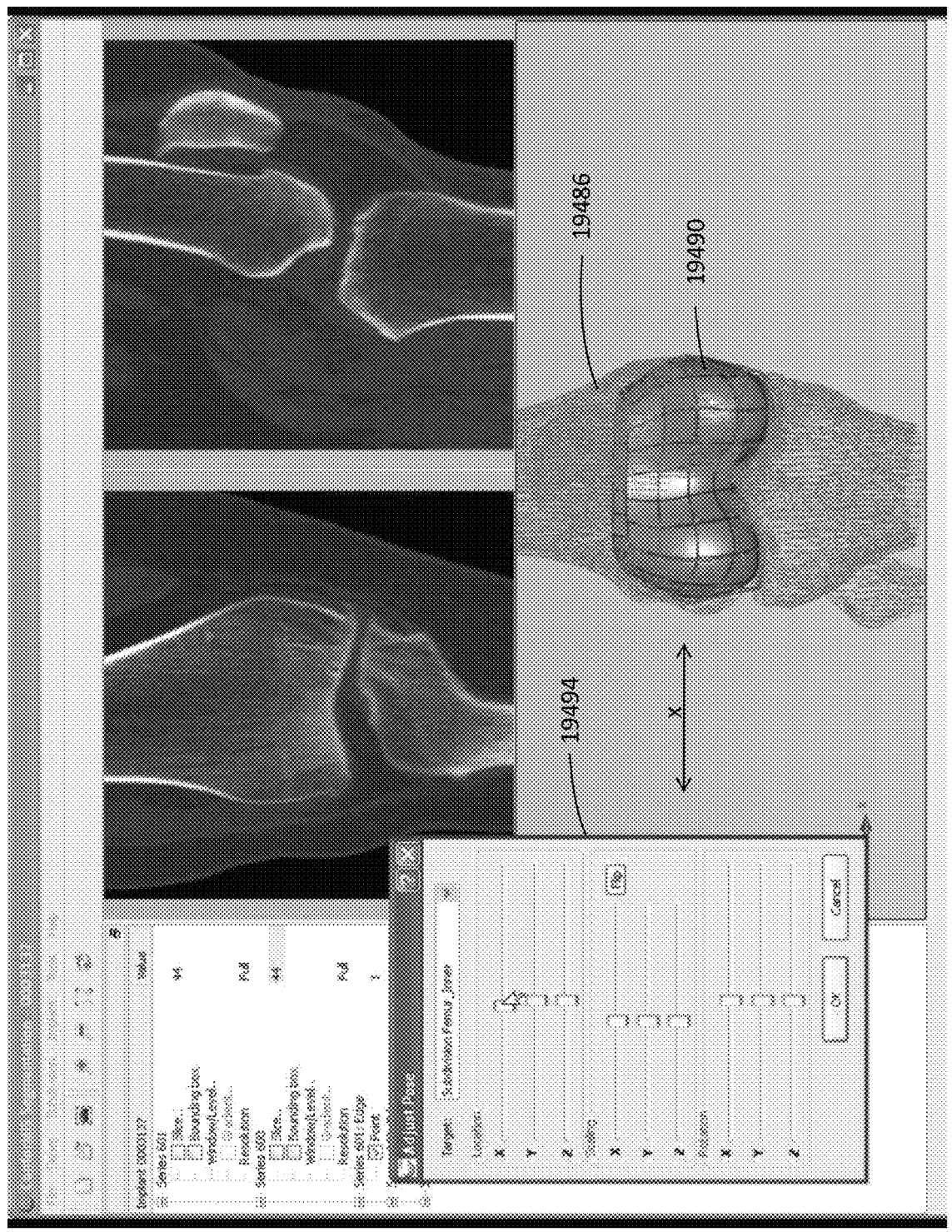
Figure 4E:
Figure 4F:
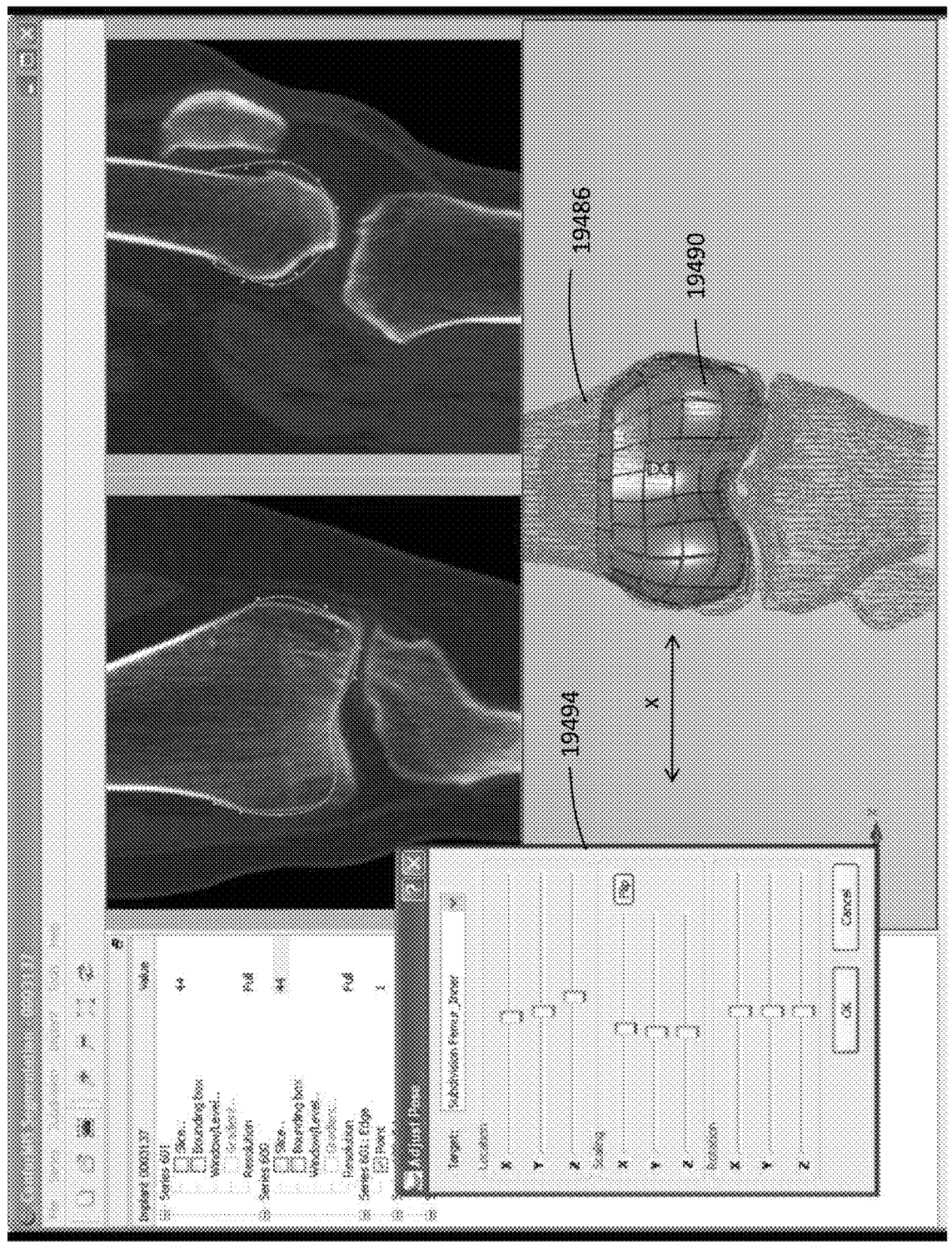
Figure 4G:
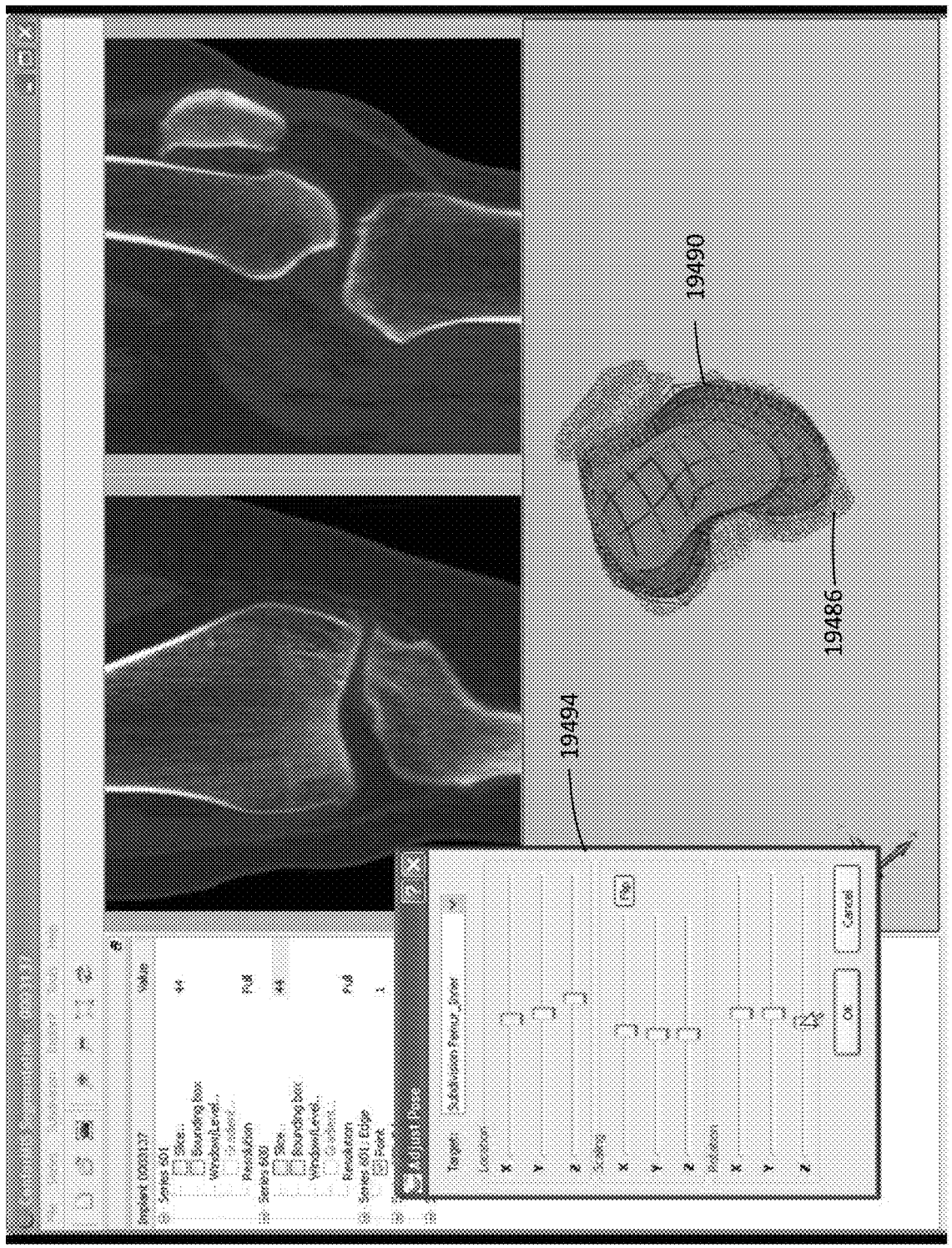
Figure 4H:
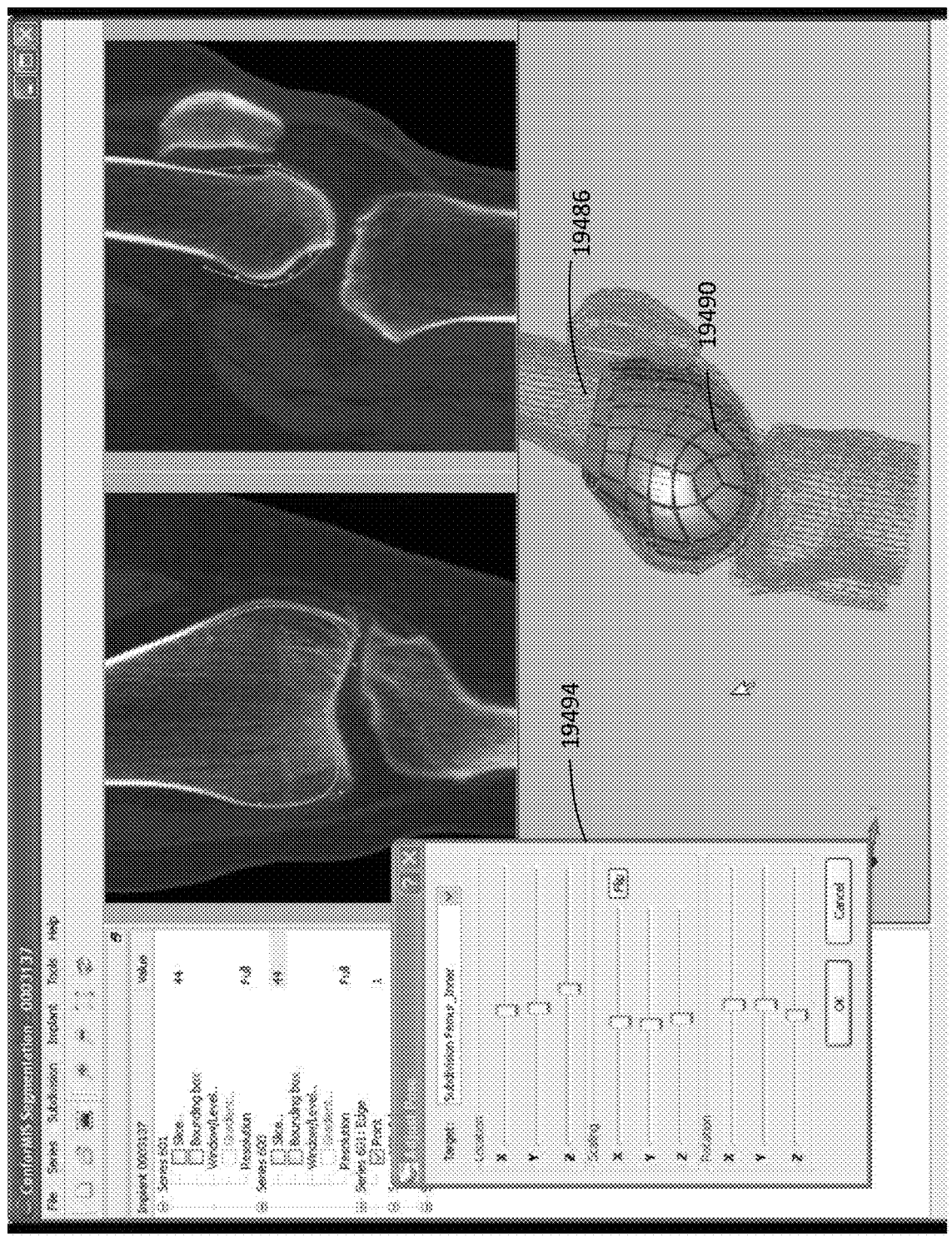

As shown by the template outline 19492 in the 2D images, the femoral template 19490 initially is not a substantial match for the approximate femoral surface 19486. This match can be improved by making global and local adjustments. Global adjustments align the template by performing operations such as rotating, translating or scaling. Local adjustments deform the surface representation of the template in certain subregions. In an optional step 19472, an operator or a user or the software can roughly fit the template model to the biological feature of interest or directly to the image data stack. FIG. 4D-4G illustrate the femoral template model 19490 being roughly adjusted to best-fit the approximate femoral surface 19486. As shown in the figures, a user can perform the adjustments using a control panel 19494. Adjustments can include, for example, adjusting the location of the template in one or more dimensions; adjusting the scale (e.g., size) of the template in one or more dimensions; and adjusting the rotation of the template in one or more dimensions. User-controlled knobs, as shown in the control panel 19494, can be used to induce position changes relative to their initial center positions. FIG. 4D illustrates a user adjustment to the location of the template model in the x axis (e.g., in the M-L direction). FIG. 4E illustrates a user adjustment to the location of the template model in the z axis (e.g., in the proximal-distal direction). FIG. 4F illustrates a user adjustment to the scale (i.e., size) of the template model in the x axis. FIG. 4G illustrates a user adjustment to rotation of the template model about the z-axis (the axis perpendicular to the view). These or other adjustments can be performed in any order and repeated as desired to achieve the best rough fit of the template with the approximate biological feature. In other embodiments, the software can automatically determine the initial best fit of the template model to the biological feature of interest or the image data. This can be achieved by finding the scaling, rotation and translation parameters that result in the closest fit of the template to the structure of interest, for example using a multidimensional optimization algorithm. FIG. 4H illustrates the rough fit of the template to the approximate surface following these adjustments.

Figure 4I:
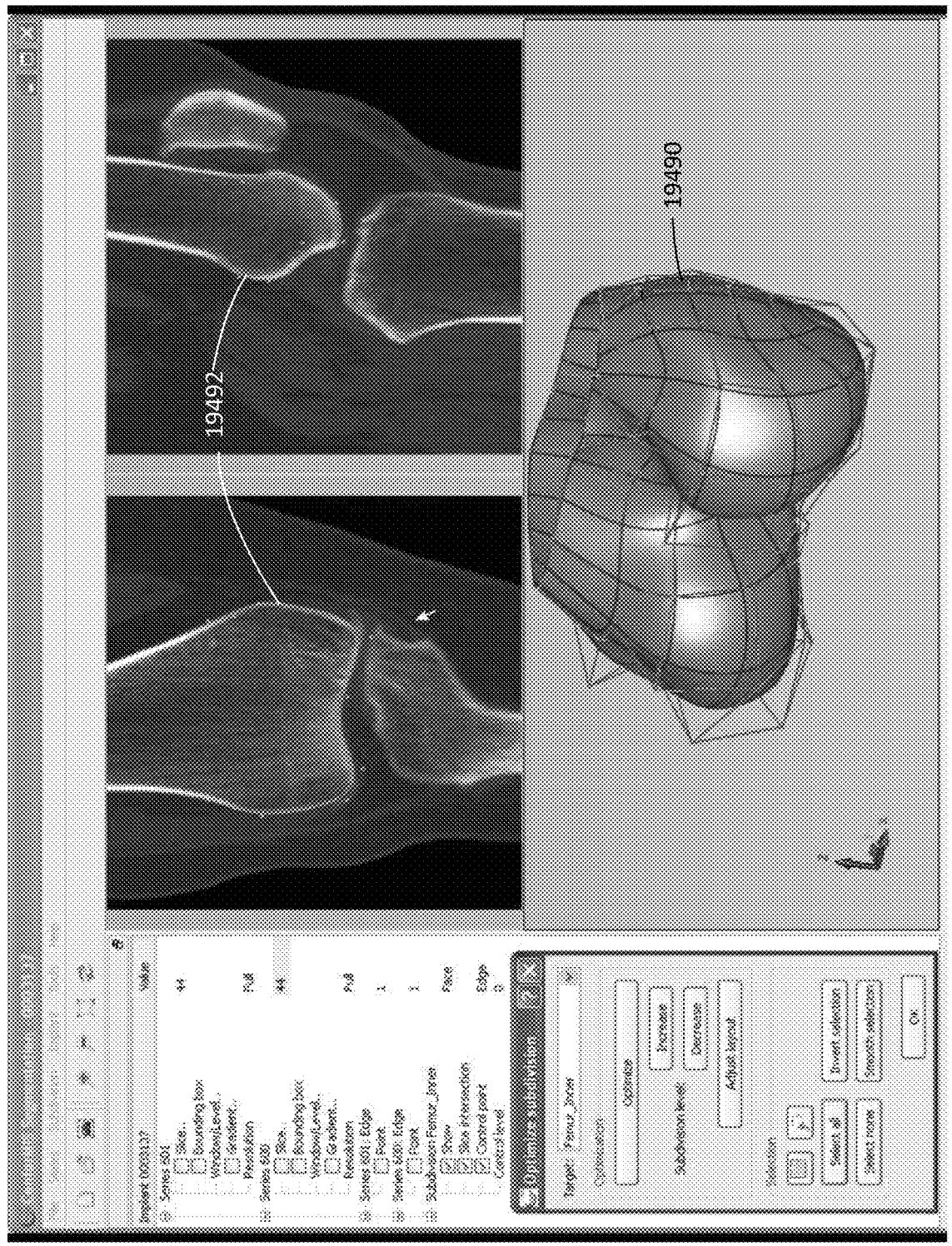

In another step 19476, the model template can be precisely fit to the collection of multiple images (rather than independently processing each image, which can optionally be accomplished using many of the various methods described herein). As shown in FIG. 4I, the surface quadrangles or "patches" of surface data representation of the femoral template 19490 can be deformed to match the surface(s) across the entire collection of images. In certain embodiments, the template patches can be deformed to directly fit the radiographic or tomographic image data (e.g., voxel data) rather than any subsequently processed data, for example, data points representing multiple voxels or data compatible with a computer monitor. If desired, radiographic or tomographic images can include much higher gray value resolution (e.g., can assign one of a much greater number of unique shades of gray to each pixel or voxel) than data compatible with a computer monitor. Accordingly, by deforming the template to directly fit the radiographic images, a high degree of resolution can be maintained, which can provide a highly precise model.

The points or dots shown in association with the template outline 19492 represent control points that can be used by a technician to manually alter the outline and surface of the template. By moving a control point, the user can manually alter and deform adjacent sections of the surface data representation of the template, and the resulting alterations and deformations appear in both the 2D outline view and in the 3D view of the template. In another embodiment, the software can optimize the position of the control points and thus the fit of the surface automatically using various criteria, for example gray values or gray value gradients in the image data or smoothness and continuity constraints in the surface data representation.

In various embodiments, the global transformations and local deformations may be determined by the software, at least in part, based on external design constraints pertinent to a particular implant design. This can include, for example, specific surface curvature radii, minimum distance between structures such as anchoring elements and/or minimum or maximum thickness or length or width dimensions of the implant or parts thereof. The transformations can also be optimized to minimize bone cuts.

In further embodiments, the model can be fit to the patient's anatomy after the axis alignment of the joint, for example the anatomical or biomechanical axis, has been corrected. The fitting, optimization or deformation of the model can then be performed taking the corrected axis into account. Alternatively, the axis alignment is corrected after the model has been fitted. The model can then undergo further adjustments as the alignment correction is performed. Thus, the position or shape of the joint bearing surfaces and other anatomical structures can be determined based on the corrected axis information.

In various embodiments, the virtual model can include, in addition to or instead of the surface model representation, one or more geometric reference structures. This can include, for example, planes, axes, curves or surfaces that can be used as construction parameters for one or more implants, guide tools and/or surgical procedures. The geometric reference structures can be used to define the position and shape of anatomical surfaces as well as the location and direction of any potential anatomical support structures, bone cuts and/or drill holes needed to position implants and/or surgical tools. Similar to the way the surface data representation can be adjusted using global transformations and local deformations as described above to match the individual patient's anatomy, the position, direction, scale and/or shape of the geometric reference structures can be adjusted accordingly—i.e. the software can selectively apply the same global transformations and local deformations applied to the surface model to the geometric reference structures as well. During this process, the position, direction, scale and/or shape of the geometric reference structures can be adjusted as well based on the transformations and deformations of the virtual shape model. Adjusting the position, direction, scale and shape of the geometric reference structures can be performed automatically by the software or based on user or operator input or a combination thereof.

Reference Points and Features

In various embodiments, information collected from a patient or patient group, including the image data and/or models described herein, can include points, surfaces, and/or landmarks, collectively referred to herein as "reference points." In certain embodiments, the reference points can be selected and used to derive a varied or altered surface, such as, without limitation, an ideal surface or structure.

In various embodiments, reference points can be used to create a model of the patient's relevant biological feature(s) and/or one or more patient-adapted surgical steps, tools, and implant components. For example the reference points can be used to design a patient-adapted implant component having at least one patient-specific or patient-engineered feature, such as a surface, dimension, or other feature.

Sets of reference points can be grouped to form reference structures used to create a model of a joint, an implant design, and/or a tool design. Designed implant and/or tool surfaces can be derived from single reference points, triangles, polygons, or more complex surfaces, such as parametric or subdivision surfaces, or models of joint material, such as, for example, articular cartilage, subchondral bone, cortical bone, endosteal bone or bone marrow. Various reference points and reference structures can be selected and manipulated to derive a varied or altered surface, such as, without limitation, an ideal surface or structure.

The reference points can be located on or in the joint that will receive the patient-adapted implant. For example, the reference points can include weight-bearing surfaces or locations in or on the joint, a cortex in the joint, cortical and/or cancellous wall boundaries, and/or an endosteal surface of the joint. The reference points also can include surfaces or locations outside of but related to the joint. Specifically, reference points can include surfaces or locations functionally related to the joint.

For example, in embodiments directed to the knee joint, reference points can include one or more locations ranging from the hip down to the ankle or foot. The reference points also can include surfaces or locations homologous to the joint receiving the implant. For example, in embodiments directed to a knee, a hip, or a shoulder joint, reference points can include one or more surfaces or locations from the contralateral knee, hip, or shoulder joint.

In certain embodiments, imaging data collected from the patient, for example, imaging data from one or more of x-ray imaging, digital tomosynthesis, cone beam CT, non-spiral or spiral CT, non-isotropic or isotropic MRI, SPECT, PET, ultrasound, laser imaging, and/or photo-acoustic imaging, is used to qualitatively and/or quantitatively measure one or more of a patient's biological features, one or more of normal cartilage, diseased cartilage, a cartilage defect, an area of denuded cartilage, subchondral bone, cortical bone, endosteal bone, bone marrow, a ligament, a ligament attachment or origin, menisci, labrum, a joint capsule, articular structures, and/or voids or spaces between or within any of these structures. The qualitatively and/or quantitatively measured biological features can include, but are not limited to, one or more of length, width, height, depth and/or thickness; curvature, for example, curvature in two dimensions (e.g., curvature in or projected onto a plane), curvature in three dimensions, and/or a radius or radii of curvature; shape, for example, two-dimensional shape or three-dimensional shape; area, for example, surface area and/or surface contour; perimeter shape; and/or volume of, for example, the patient's cartilage, bone (subchondral bone, cortical bone, endosteal bone, and/or other bone), ligament, and/or voids or spaces between them.

In certain embodiments, measurements of biological features can include any one or more of the illustrative measurements identified in Table 1.

TABLE 1

Exemplary patient-specific measurements of biological features that can be used in the creation of a model and/or in the selection and/or design of an implant component

| Anatomical feature | Exemplary measurement |
| --- | --- |
| Joint-line, joint gap | Location relative to proximal reference point |
| | Location relative to distal reference point |
| | Angle |
| | Gap distance between opposing surfaces in one or more locations |
| | Location, angle, and/or distance relative to contralateral joint |
| Soft tissue tension and/or balance | Joint gap distance |
| | Joint gap differential, e.g., medial to lateral |
| Medullary cavity | Shape in one or more dimensions |
| | Shape in one or more locations |
| | Diameter of cavity |
| | Volume of cavity |
| Subchondral bone | Shape in one or more dimensions |
| | Shape in one or more locations |
| | Thickness in one or more dimensions |
| | Thickness in one or more locations |
| | Angle, e.g., resection cut angle |
| Cortical bone | Shape in one or more dimensions |
| | Shape in one or more locations |
| | Thickness in one or more dimensions |
| | Thickness in one or more locations |
| | Angle, e.g., resection cut angle |
| | Portions or all of cortical bone perimeter at an intended resection level |
| Endosteal bone | Shape in one or more dimensions |
| | Shape in one or more locations |
| | Thickness in one or more dimensions |
| | Thickness in one or more locations |
| | Angle, e.g., resection cut angle |
| Cartilage | Shape in one or more dimensions |
| | Shape in one or more locations |
| | Thickness in one or more dimensions |
| | Thickness in one or more locations |
| | Angle, e.g., resection cut angle |
| Intercondylar notch | Shape in one or more dimensions |
| | Location |
| | Height in one or more locations |
| | Width in one or more locations |
| | Depth in one or more locations |
| | Angle, e.g., resection cut angle |
| Medial condyle | 2D and/or 3D shape of a portion or all |
| | Height in one or more locations |
| | Length in one or more locations |
| | Width in one or more locations |
| | Depth in one or more locations |
| | Thickness in one or more locations |
| | Curvature in one or more locations |
| | Slope in one or more locations and/or directions |
| | Angle, e.g., resection cut angle |
| | Portions or all of cortical bone perimeter at an intended resection level |
| | Resection surface at an intended resection level |
| Lateral condyle | 2D and/or 3D shape of a portion or all |
| | Height in one or more locations |
| | Length in one or more locations |
| | Width in one or more locations |
| | Depth in one or more locations |
| | Thickness in one or more locations |
| | Curvature in one or more locations |
| | Slope in one or more locations and/or directions |

TABLE 1-continued

Exemplary patient-specific measurements of biological features that can be used in the creation of a model and/or in the selection and/or design of an implant component

| Anatomical feature | Exemplary measurement |
|---|---|
| Trochlea | Angle, e.g., resection cut angle<br>Portions or all of cortical bone perimeter at an intended resection level<br>Resection surface at an intended resection level<br>2D and/or 3D shape of a portion or all<br>Height in one or more locations<br>Length in one or more locations<br>Width in one or more locations<br>Depth in one or more locations<br>Thickness in one or more locations<br>Curvature in one or more locations<br>Groove location in one or more locations<br>Trochlear angle, e.g., groove angle in one or more locations<br>Slope in one or more locations and/or directions<br>Angle, e.g., resection cut angle<br>Portions or all of cortical bone perimeter at an intended resection level<br>Resection surface at an intended resection level |
| Medial trochlea | 2D and/or 3D shape of a portion or all<br>Height in one or more locations<br>Length in one or more locations<br>Width in one or more locations<br>Depth in one or more locations<br>Thickness in one or more locations<br>Curvature in one or more locations<br>Slope in one or more locations and/or directions<br>Angle, e.g., resection cut angle<br>Portions or all of cortical bone perimeter at an intended resection level<br>Resection surface at an intended resection level |
| Central trochlea | 2D and/or 3D shape of a portion or all<br>Height in one or more locations<br>Length in one or more locations<br>Width in one or more locations<br>Depth in one or more locations<br>Thickness in one or more locations<br>Curvature in one or more locations<br>Groove location in one or more locations<br>Trochlear angle, e.g., groove angle in one or more locations<br>Slope in one or more locations and/or directions<br>Angle, e.g., resection cut angle<br>Portions or all of cortical bone perimeter at an intended resection level<br>Resection surface at an intended resection level |
| Lateral trochlea | 2D and/or 3D shape of a portion or all<br>Height in one or more locations<br>Length in one or more locations<br>Width in one or more locations<br>Depth in one or more locations<br>Thickness in one or more locations<br>Curvature in one or more locations<br>Slope in one or more locations and/or directions<br>Angle, e.g., resection cut angle<br>Portions or all of cortical bone perimeter at an intended resection level<br>Resection surface at an intended resection level |
| Entire tibia | 2D and/or 3D shape of a portion or all<br>Height in one or more locations<br>Length in one or more locations<br>Width in one or more locations<br>Depth in one or more locations<br>Thickness in one or more locations<br>Curvature in one or more locations<br>Slope in one or more locations and/or directions (e.g., medial and/or lateral)<br>Angle, e.g., resection cut angle<br>Axes, e.g., A-P and/or M-L axes<br>Osteophytes<br>Plateau slope(s), e.g., relative slopes medial and lateral<br>Plateau heights(s), e.g., relative heights medial and lateral |
| | Bearing surface radii, e.g., relative radii medial and lateral<br>Perimeter profile<br>Portions or all of cortical bone perimeter at an intended resection level<br>Resection surface at an intended resection level |
| Medial tibia | 2D and/or 3D shape of a portion or all<br>Height in one or more locations<br>Length in one or more locations<br>Width in one or more locations<br>Depth in one or more locations<br>Thickness or height in one or more locations<br>Curvature in one or more locations<br>Slope in one or more locations and/or directions<br>Angle, e.g., resection cut angle<br>Perimeter profile<br>Portions or all of cortical bone perimeter at an intended resection level<br>Resection surface at an intended resection level |
| Lateral tibia | 2D and/or 3D shape of a portion or all<br>Height in one or more locations<br>Length in one or more locations<br>Width in one or more locations<br>Depth in one or more locations<br>Thickness/height in one or more locations<br>Curvature in one or more locations<br>Slope in one or more locations and/or directions<br>Angle, e.g., resection cut angle<br>Perimeter profile<br>Portions or all of cortical bone perimeter at an intended resection level<br>Resection surface at an intended resection level |
| Entire patella | 2D and/or 3D shape of a portion or all<br>Height in one or more locations<br>Length in one or more locations<br>Width in one or more locations<br>Depth in one or more locations<br>Thickness in one or more locations<br>Curvature in one or more locations<br>Slope in one or more locations and/or directions<br>Perimeter profile<br>Angle, e.g., resection cut angle<br>Portions or all of cortical bone perimeter at an intended resection level<br>Resection surface at an intended resection level |
| Medial patella | 2D and/or 3D shape of a portion or all<br>Height in one or more locations<br>Length in one or more locations<br>Width in one or more locations<br>Depth in one or more locations<br>Thickness in one or more locations<br>Curvature in one or more locations<br>Slope in one or more locations and/or directions<br>Angle, e.g., resection cut angle<br>Portions or all of cortical bone perimeter at an intended resection level<br>Resection surface at an intended resection level |
| Central patella | 2D and/or 3D shape of a portion or all<br>Height in one or more locations<br>Length in one or more locations<br>Width in one or more locations<br>Depth in one or more locations<br>Thickness in one or more locations<br>Curvature in one or more locations<br>Slope in one or more locations and/or directions<br>Angle, e.g., resection cut angle<br>Portions or all of cortical bone perimeter at an intended resection level<br>Resection surface at an intended resection level |
| Lateral patella | 2D and/or 3D shape of a portion or all<br>Height in one or more locations<br>Length in one or more locations<br>Width in one or more locations<br>Depth in one or more locations |

TABLE 1-continued

Exemplary patient-specific measurements of biological features that can be used in the creation of a model and/or in the selection and/or design of an implant component

| Anatomical feature | Exemplary measurement |
|---|---|
| Femoral head | Thickness in one or more locations<br>Curvature in one or more locations<br>Slope in one or more locations and/or directions<br>Angle, e.g., resection cut angle<br>Portions or all of cortical bone perimeter at an intended resection level<br>Resection surface at an intended resection level<br>2D and/or 3D shape of a portion or all<br>Height in one or more locations<br>Length in one or more locations<br>Width in one or more locations<br>Depth in one or more locations<br>Thickness in one or more locations<br>Curvature in one or more locations<br>Slope in one or more locations and/or directions<br>Angle, e.g., resection cut angle<br>Anteversion or retroversion<br>Portions or all of bone perimeter at an intended resection level<br>Resection surface at an intended resection level |
| Femoral neck | 2D and/or 3D shape of a portion or all<br>Height in one or more locations<br>Length in one or more locations<br>Width in one or more locations<br>Depth in one or more locations<br>Thickness in one or more locations<br>Angle in one or more locations<br>Neck axis in one or more locations<br>Curvature in one or more locations<br>Slope in one or more locations and/or directions<br>Angle, e.g., resection cut angle<br>Anteversion or retroversion<br>Leg length<br>Portions or all of cortical bone perimeter at an intended resection level<br>Resection surface at an intended resection level |
| Femoral shaft | 2D and/or 3D shape of a portion or all<br>Height in one or more locations<br>Length in one or more locations<br>Width in one or more locations<br>Depth in one or more locations<br>Thickness in one or more locations<br>Angle in one or more locations<br>Shaft axis in one or more locations<br>Curvature in one or more locations<br>Angle, e.g., resection cut angle<br>Anteversion or retroversion<br>Leg length<br>Portions or all of cortical bone perimeter at an intended resection level<br>Resection surface at an intended resection level |
| Acetabulum | 2D and/or 3D shape of a portion or all<br>Height in one or more locations<br>Length in one or more locations<br>Width in one or more locations<br>Depth in one or more locations<br>Thickness in one or more locations<br>Curvature in one or more locations<br>Slope in one or more locations and/or directions<br>Angle, e.g., resection cut angle<br>Anteversion or retroversion<br>Portions or all of cortical bone perimeter at an intended resection level<br>Resection surface at an intended resection level |
| Glenoid | 2D and/or 3D shape of a portion or all<br>Height in one or more locations<br>Length in one or more locations<br>Width in one or more locations<br>Depth in one or more locations<br>Thickness in one or more locations<br>Curvature in one or more locations<br>Slope in one or more locations and/or directions<br>Angle, e.g., resection cut angle<br>Anteversion or retroversion |
| Humeral head | Portions or all of cortical bone perimeter at an intended resection level<br>Resection surface at an intended resection level<br>2D and/or 3D shape of a portion or all<br>Height in one or more locations<br>Length in one or more locations<br>Width in one or more locations<br>Depth in one or more locations<br>Thickness in one or more locations<br>Curvature in one or more locations<br>Slope in one or more locations and/or directions<br>Angle, e.g., resection cut angle<br>Anteversion or retroversion<br>Portions or all of cortical bone perimeter at an intended resection level<br>Resection surface at an intended resection level |
| Humeral neck | 2D and/or 3D shape of a portion or all<br>Height in one or more locations<br>Length in one or more locations<br>Width in one or more locations<br>Depth in one or more locations<br>Thickness in one or more locations<br>Angle in one or more locations<br>Neck axis in one or more locations<br>Curvature in one or more locations<br>Slope in one or more locations and/or directions<br>Angle, e.g., resection cut angle<br>Anteversion or retroversion<br>Arm length<br>Portions or all of cortical bone perimeter at an intended resection level<br>Resection surface at an intended resection level |
| Humeral shaft | 2D and/or 3D shape of a portion or all<br>Height in one or more locations<br>Length in one or more locations<br>Width in one or more locations<br>Depth in one or more locations<br>Thickness in one or more locations<br>Angle in one or more locations<br>Shaft axis in one or more locations<br>Curvature in one or more locations<br>Angle, e.g., resection cut angle<br>Anteversion or retroversion<br>Arm length<br>Portions or all of cortical bone perimeter at an intended resection level<br>Resection surface at an intended resection level |
| Ankle joint | 2D and/or 3D shape of a portion or all<br>Height in one or more locations<br>Length in one or more locations<br>Width in one or more locations<br>Depth in one or more locations<br>Thickness in one or more locations<br>Curvature in one or more locations<br>Slope in one or more locations and/or directions<br>Angle, e.g., resection cut angle<br>Portions or all of cortical bone perimeter at an intended resection level<br>Resection surface at an intended resection level |
| Elbow | 2D and/or 3D shape of a portion or all<br>Height in one or more locations<br>Length in one or more locations<br>Width in one or more locations<br>Depth in one or more locations<br>Thickness in one or more locations<br>Curvature in one or more locations<br>Slope in one or more locations and/or directions<br>Angle, e.g., resection cut angle<br>Portions or all of cortical bone perimeter at an intended resection level<br>Resection surface at an intended resection level |
| Wrist | 2D and/or 3D shape of a portion or all<br>Height in one or more locations<br>Length in one or more locations |

TABLE 1-continued

Exemplary patient-specific measurements of biological features that can be used in the creation of a model and/or in the selection and/or design of an implant component

| Anatomical feature | Exemplary measurement |
| --- | --- |
|  | Width in one or more locations |
|  | Depth in one or more locations |
|  | Thickness in one or more locations |
|  | Curvature in one or more locations |
|  | Slope in one or more locations and/or directions |
|  | Angle, e.g., resection cut angle |
|  | Portions or all of cortical bone perimeter at an intended resection level |
|  | Resection surface at an intended resection level |
| Hand | 2D and/or 3D shape of a portion or all |
|  | Height in one or more locations |
|  | Length in one or more locations |
|  | Width in one or more locations |
|  | Depth in one or more locations |
|  | Thickness in one or more locations |
|  | Curvature in one or more locations |
|  | Slope in one or more locations and/or directions |
|  | Angle, e.g., resection cut angle |
|  | Portions or all of cortical bone perimeter at an intended resection level |
|  | Resection surface at an intended resection level |
| Finger | 2D and/or 3D shape of a portion or all |
|  | Height in one or more locations |
|  | Length in one or more locations |
|  | Width in one or more locations |
|  | Depth in one or more locations |
|  | Thickness in one or more locations |
|  | Curvature in one or more locations |
|  | Slope in one or more locations and/or directions |
|  | Angle |
|  | Portions or all of cortical bone perimeter at an intended resection level |
|  | Resection surface at an intended resection level |
| Spine | 2D and/or 3D shape of a portion or all |
|  | Height in one or more locations |
|  | Length in one or more locations |
|  | Width in one or more locations |
|  | Depth in one or more locations |
|  | Thickness in one or more locations |
|  | Curvature in one or more locations |
|  | Slope in one or more locations and/or directions |
|  | Angle, e.g., resection cut angle |
|  | Portions or all of cortical bone perimeter at an intended resection level |
|  | Resection surface at an intended resection level |
| Spinal facet joint | 2D and/or 3D shape of a portion or all |
|  | Height in one or more locations |
|  | Length in one or more locations |
|  | Width in one or more locations |
|  | Depth in one or more locations |
|  | Thickness in one or more locations |
|  | Curvature in one or more locations |
|  | Slope in one or more locations and/or directions |
|  | Angle, e.g., resection cut angle |

Depending on the clinical application, a single or any combination or all of the measurements described in Table 1 and/or known in the art can be used. Additional patient-specific measurements and information that can be used in the evaluation can include, for example, joint kinematic measurements, bone density measurements, bone porosity measurements, soft and connective tissues structures, skin, muscles, identification of damaged or deformed tissues or structures, and patient information, such as patient age, weight, gender, ethnicity, activity level, and overall health status. Moreover, the patient-specific measurements may be compared, analyzed or otherwise modified based on one or more "normalized" patient model or models, or by reference to a desired database of anatomical features of interest. For example, a series of patient-specific femoral measurements may be compiled and compared to one or more exemplary femoral or tibial measurements from a library or other database of "normal" (or other reference population) femur measurements. Comparisons and analysis thereof may concern, but is not limited to, one or more or any combination of the following dimensions: femoral shape, length, width, height, of one or both condyles, intercondylar shapes and dimensions, trochlea shape and dimensions, coronal curvature, sagittal curvature, cortical/cancellous bone volume and/or quality, etc., and a series of recommendations and/or modifications may be accomplished. Any parameter mentioned in the specification and in the various Tables throughout the specification, including anatomic, biomechanical and kinematic parameters, can be utilized, not only in the knee, but also in the hip, shoulder, ankle, elbow, wrist, spine and other joints. Such analysis may include modification of one or more patient-specific features and/or design criteria for the implant to account for any underlying deformity reflected in the patient-specific measurements. If desired, the modified data may then be utilized to select and/or design an appropriate implant and/or tool to match the modified features, and a final verification operation may be accomplished to ensure the selected and/or designed implant and/or tool is acceptable and appropriate to the original unmodified patient-specific measurements (i.e., the selected and/or designed implant and/or tool will ultimately "fit" the original patient anatomy). In alternative embodiments, the various anatomical features may be differently "weighted" during the comparison process (utilizing various formulaic weightings and/or mathematical algorithms), based on their relative importance or other criteria chosen by the designer/programmer and/or physician.

In addition to (or optionally in place of) the above-mentioned measurements, it may be desirable to obtain measurements of the targeted joint (as well as surrounding anatomical areas and or other joints of the patient's anatomy) in a load-bearing or otherwise "real-world" condition. Such measurements can potentially yield extremely useful data on the alignment and/or movement of the joint and surrounding structures (as well as the loading conditions of the various joint components)—information which may be difficult to obtain or model from standard imaging techniques (i.e., sitting or lying X-rays, CT-scans and/or MRI imaging). Such load-bearing measurements can include imaging of the patient standing, walking and/or carrying loads of varying sizes and/or weights.

It may also be desirable to model various patient measurements (including non-load-bearing measurements as described above) to simulate the targeted joint and surrounding anatomy virtually. Such simulations can include virtually modeling the alignment and load bearing condition of the joint and surrounding anatomical structures for the patient standing and/or moving (i.e., walking, running, jumping, squatting, kneeling, walking up and down stairs or inclines/declines, picking up objects, etc.). Such simulations can be used to obtain valuable anatomical, biomechanical and kinematic data including the loaded conditions of various joint components, component positions, component movement, joint and/or surrounding tissue anatomical or biomechanical constraints or limitations, as well as estimated mechanical axes in one or more directions (i.e., coronal, sagittal or combinations thereof). This information could then be utilized (alone or in combination with other data described herein) to design various features of a joint resurfacing/replacement implant. This method can be incorporated in the various embodiments described herein as additional patient measurement and anatomical/joint modeling and design data. This analysis is applicable to many different joints, including those of a medial condyle, a lateral condyle, a trochlea, a medial tibia, a lateral tibia, the entire tibia, a medial patella, a lateral patella, an entire patella, a medial trochlea, a central trochlea, a lateral trochlea, a portion of a femoral head, an entire femoral head, a portion of an acetabulum, an entire acetabulum, a portion of a glenoid, an entire glenoid, a portion of a humeral head, an entire humeral head, a portion of an ankle joint, an entire ankle joint, and/or a portion or an entire elbow, wrist, hand, finger, spine or facet joint.

Modeling Proper Limb Alignment

Proper joint and limb function typically depend on correct limb alignment. For example, in repairing a knee joint with one or more knee implant components, optimal functioning of the new knee will often depend, at least partially, on the correct alignment of the anatomical and/or mechanical axes of the lower extremity. Accordingly, an important consideration in designing and/or replacing a natural joint with one or more implant components is proper limb alignment or, when the malfunctioning joint contributes to a misalignment, proper realignment of the limb. Alignment can include static alignment in various orientations as well as alignment throughout portions and/or all of a range of motion of the joint.

Certain embodiments described herein include collecting and using data from imaging sources and/or tests to virtually determine, in one or more planes, one or more anatomic axes and/or one or more mechanical axes of a joint or extremity and the related misalignment of a patient's limb. The misalignment of a limb joint relative to the axis can identify the degree of deformity, for example, varus or valgus deformity in the coronal plane or genu antecurvatum or recurvatum deformity in the sagittal plane. Then, one or more of the patient-specific implant components and/or the implant procedure steps, such as bone resection, can be designed to help correct the misalignment.

Imaging data can be used to virtually determine a patient's axis and misalignment, anatomic reference points and/or limb alignment, including alignment angles within the same and between different joints or to simulate normal limb alignment. Any anatomic features related to the misalignment can be selected and imaged. For example, in certain embodiments, such as for a knee or hip implant, the imaging test can include data from at least one of, or several of, a hip joint, knee joint and ankle joint. The imaging test can be obtained in lying, prone, supine or standing position. The imaging test can include only the target joint, or both the target joint and also selected data through one or more adjoining and/or opposing joints.

Using the image data, one or more mechanical or anatomical axes, angles, planes or combinations thereof can be determined. In certain embodiments, such axes, angles, and/or planes can include, or be derived from, one or more of a Whiteside's line, Blumensaat's line, transepicondylar line, femoral shaft axis, femoral neck axis, acetabular angle, lines tangent to the superior and inferior acetabular margin, lines tangent to the anterior or posterior acetabular margin, femoral shaft axis, tibial shaft axis, transmalleolar axis, posterior condylar line, tangent(s) to the trochlea of the knee joint, tangents to the medial or lateral patellar facet, lines tangent or perpendicular to the medial and lateral posterior condyles, lines tangent or perpendicular to a central weight-bearing zone of the medial and lateral femoral condyles, lines transecting the medial and lateral posterior condyles, for example through their respective centerpoints, lines tangent or perpendicular to the tibial tuberosity, lines vertical or at an angle to any of the aforementioned lines, and/or lines tangent to or intersecting the cortical bone of any bone adjacent to or enclosed in a joint. Moreover, estimating a mechanical axis, an angle, or plane also can be performed using image data obtained through two or more joints, such as the knee and ankle joint, for example, by using the femoral shaft axis and a centerpoint or other point in the ankle, such as a point between the malleoli.

As one example, if surgery of the knee or hip is contemplated, the imaging test can include acquiring data through at least one of, or several of, a hip joint, knee joint or ankle joint. As another example, if surgery of the knee joint is contemplated, a mechanical axis can be determined. For example, the centerpoint of the hip, knee and ankle can be determined. By connecting the centerpoint of the hip with that of the ankle, a mechanical axis can be determined in the coronal plane. The position of the knee relative to said mechanical axis can be a reflection of the degree of varus or valgus deformity. The same determinations can be made in the sagittal plane, for example to determine the degree of genu antecurvatum or recurvatum. Similarly, any of these determinations can be made in any other desired planes, in two or three dimensions. A desired alignment throughout a desired range of motion may be derived using individual measurements and/or a combination of multiple measurements along multiple planes.

Establishing Normal or Near-Normal Joint Kinematics

In certain embodiments, a computer program simulating biomotion of one or more joints, such as, for example, a knee joint, or a knee and ankle joint, or a hip, knee and/or ankle joint, can be utilized. In certain embodiments, imaging data as previously described, which can include information related to the joint or extremity of interest as well as information regarding adjacent anatomical structures, can be entered into the computer program. In addition to (or in place of) patient-specific image data, patient-specific kinematic data, for example obtained in a gait lab, can be entered into the computer program. Alternatively, patient-specific navigation data, for example generated using a surgical navigation system, image guided or non-image guided, can be entered into the computer program. This kinematic or navigation data can, for example, be generated by applying optical or RF markers to the limb and by registering the markers and then measuring limb movements, for example, flexion, extension, abduction, adduction, rotation, and other limb movements.

Optionally, other data including anthropometric data may be added for each patient. These data can include but are not limited to the patient's age, gender, weight, height, size, body mass index, and race. Desired limb alignment and/or deformity correction can be added into the model. The position of bone cuts on one or more articular surfaces as well as the intended location of implant bearing surfaces on one or more articular surfaces can be entered into the model.

A patient-specific biomotion model can be derived that includes combinations of parameters listed above. The biomotion model can simulate various activities of daily life, including normal gait, stair climbing, descending stairs, running, kneeling, squatting, sitting and any other physical activity (including activities relevant to other joints of interest). The biomotion model can start out with standardized activities, typically derived from reference databases. These reference databases can be generated, for example, using biomotion measurements using force plates and motion trackers using radiofrequency or optical markers and video equipment.

The biomotion model can then be individualized with use of patient-specific information including at least one of, but not limited to, the patient's age, gender, weight, height, body mass index, and race, the desired limb alignment or deformity correction, and the patient's imaging data, for example, a series of two-dimensional images or a three-dimensional representation of the joint for which surgery is contemplated.

An implant shape including associated bone cuts generated in various optimizations and/or modifications discussed herein, for example, limb alignment, deformity correction and/or bone preservation on one or more articular surfaces, can be introduced into the model. Table 2 includes an exemplary list of parameters that can be measured in a patient-specific biomotion model.

TABLE 2

Parameters measured in a patient-specific biomotion model for various implants

| Joint implant | Measured Parameter |
|---|---|
| knee | Medial femoral rollback during flexion |
| knee | Lateral femoral rollback during flexion |
| knee | Patellar position, medial, lateral, superior, inferior for different flexion and extension angles |
| knee | Internal and external rotation of one or more femoral condyles |
| knee | Internal and external rotation of the tibia |
| knee | Flexion and extension angles of one or more articular surfaces |
| knee | Anterior slide and posterior slide of at least one of the medial and lateral femoral condyles during flexion or extension |
| knee | Medial and lateral laxity throughout the range of motion |
| knee | Contact pressure or forces on at least one or more articular surfaces, e.g., a femoral condyle and a tibial plateau, a trochlea and a patella |
| knee | Contact area on at least one or more articular surfaces, e.g., a femoral condyle and a tibial plateau, a trochlea and a patella |
| knee | Forces between the bone-facing surface of the implant, an optional cement interface and the adjacent bone or bone marrow, measured at least one or multiple bone cut or bone-facing surface of the implant on at least one or multiple articular surfaces or implant components. |
| knee | Ligament location, e.g., ACL, PCL, MCL, LCL, retinacula, joint capsule, estimated or derived, for example using an imaging test. |
| knee | Ligament tension, strain, shear force, estimated failure forces, loads for example for different angles of flexion, extension, rotation, abduction, adduction, with the different positions or movements optionally simulated in a virtual environment. |
| knee | Potential implant impingement on other articular structures, e.g., in high flexion, high extension, internal or external rotation, abduction or adduction or any combinations thereof or other angles/positions/movements. |
| Hip, shoulder or other joint | Internal and external rotation of one or more articular surfaces |
| Hip, shoulder or other joint | Flexion and extension angles of one or more articular surfaces |
| Hip, shoulder or other joint | Anterior slide and posterior slide of at least one or more articular surfaces during flexion or extension, abduction or adduction, elevation, internal or external rotation |
| Hip, shoulder or other joint | Joint laxity throughout the range of motion |
| Hip, shoulder or other joint | Contact pressure or forces on at least one or more articular surfaces, e.g., an acetabulum and a femoral head, a glenoid and a humeral head |
| Hip, shoulder or other joint | Forces between the bone-facing surface of the implant, an optional cement interface and the adjacent bone or bone marrow, measured at least one or multiple bone cut or bone-facing surface of the implant on at least one or multiple articular surfaces or implant components. |
| Hip, shoulder or other joint | Ligament location, e.g., transverse ligament, glenohumeral ligaments, retinacula, joint capsule, estimated or derived, for example using an imaging test. |
| Hip, shoulder or other joint | Ligament tension, strain, shear force, estimated failure forces, loads for example for different angles of flexion, extension, rotation, abduction, adduction, with the different positions or movements optionally simulated in a virtual environment. |
| Hip, shoulder or other joint | Potential implant impingement on other articular structures, e.g., in high flexion, high extension, internal or external rotation, abduction or adduction or elevation or any combinations thereof or other angles/positions/movements. |

The above list is not meant to be exhaustive, but only exemplary. Any other biomechanical parameter known in the art can be included in the analysis.

The resultant biomotion data can be used to further optimize the implant and/or procedure design with the objective to establish normal or near normal kinematics. The implant optimizations can include one or multiple implant components. Implant and/or procedure optimizations based on patient-specific data, including image-based biomotion data, include (but are not limited to):

Changes to external, joint-facing implant shape in coronal plane

Changes to external, joint-facing implant shape in sagittal plane

Changes to external, joint-facing implant shape in axial plane

Changes to external, joint-facing implant shape in multiple planes or three dimensions Changes to internal, bone-facing implant shape in coronal plane Changes to internal, bone-facing implant shape in sagittal plane Changes to internal, bone-facing implant shape in axial plane Changes to internal, bone-facing implant shape in multiple planes or three dimensions Changes to one or more bone cuts, for example with regard to depth of cut, orientation of cut Biomotion models for a particular patient can be supplemented with patient-specific finite element modeling, population-specific finite element modeling and/or other biomechanical models known in the art. In many cases, bony anatomy may be readily imaged and/or defined for a given patient's anatomy, but the muscles and connective tissues of the body (and a variety of other such "softer" tissues) may not be so readily identified from anatomical image data. In such cases, additional biomechanical models of softer tissues can be obtained that provide a readily available and accurate source of data for incorporation into the patient's bony anatomical model. The soft tissue models can supplement the bony anatomy models at a wide variety of simulation levels, from "gross movement" anatomical models having low modeling complexity (i.e., only major muscle groups being modeled, with simple lines of action and limited choice of tissue connection points) to highly complex models (i.e., modeling of multiple tissue groups, including muscles, tendons, ligaments, fatty tissues, articular cartilage, etc, with complex lines of action and connection points, including the potential to simulate the actual bony connection points from anatomical images to further refine the combined model).

Using such combined modeling, resultant forces, motions and kinematics of various joints, such as the knee joint, can be calculated for each component for each specific patient. Modeling can include static and dynamic modeling, and can allow simulation of a patient's joint structures at a variety of alignments and/or loading conditions. If desired, an implant can be engineered to accommodate such models, as well as the patient's load and force demands for a variety of conditions. For instance, in one embodiment a 125 lb. patient may not need a tibial plateau as thick as a patient with 280 lbs. Similarly, in various embodiments one or more polyethylene inserts and/or components in various implants can be adjusted in shape, thickness and material properties for each patient. For example, a 3 mm polyethylene insert can be used in a light patient with low force and a heavier or more active patient may need an 8 mm polymer insert or similar device.

Selecting and/or Designing Implants, Tools and/or Procedures

Once one or more desired models has been created using the various techniques described above, the models (optionally with information from other data sources) can be utilized to select and/or design appropriate implant components and/or surgical tools, as well as to plan the surgical procedure.

Templates and Deformable Models

In various embodiments, various aspects of the models and systems described herein, including the virtual model, can include (in addition to or instead of the surface model representation), a template for one or more implants and/or guide tools, including the position and shape of hard and soft tissues, bearing surfaces, and the location and direction of bone cuts and/or drill holes needed to position the implants. Similar to the way the surface data representation is adjusted using global transformations and local deformations as described herein to match the individual patient's anatomy, the shape of the implants and/or guide tools can be adjusted accordingly, i.e., the software applies similar global transformations and/or local deformations, as applied to the surface model, to the implants and/or guide tools as well. During this process, the position and shape of the bearing surfaces as well as the position and direction of bone cuts and/or drill holes can be adjusted based on the transformations and deformations of the virtual shape model. Adjusting the position and shape of bearing surfaces and the position and direction of bone cuts and/or drill holes can be performed automatically by the software or based on user or operator input or a combination thereof.

Library/Databases of Repair Systems

In various embodiments, an articular repair system (e.g., resection cut strategy, guide tools, and implant components) can be formed or selected from a library or database of systems of various sizes, including various medio-lateral (ML), antero-posterior (AP), and supero-inferior (SI) dimensions, curvatures, and thicknesses. The articular repair system may be formed or selected such that it achieves various parameters, such as, for example, a near anatomic fit or match with the surrounding or adjacent cartilage, cortical bone, trabecular bone, subchondral bone, menisci, and/or cut bone (including bone cut before or after preparing an implantation site). The shape of the repair system can be based on the analysis of an electronic image. If the articular repair system is intended to replace an area of diseased cartilage or lost cartilage, the near anatomic fit can be achieved using a method that provides a virtual reconstruction of the shape of healthy cartilage in an electronic image. These systems can be pre-made or made to order for an individual patient.

In order to control the fit or match of the articular repair system with the surrounding or adjacent cartilage, cortical bone, trabecular bone, subchondral bone, cut bone and/or menisci and other tissues preoperatively, a software program can be used that projects the articular repair system over the anatomic position where it will be implanted. Suitable software is commercially available and/or can be readily modified or designed by a skilled programmer. In some embodiments, an articular surface repair system can be projected over the implantation site prior to, during or after planning or simulating the surgery virtually using one or more 3-D images. The cartilage, cortical bone, trabecular bone, subchondral bone, cut bone, menisci, and/or other anatomic structures are extracted from a 3-D electronic image such as an MRI or a CT using manual, semi-automated and/or automated segmentation techniques. In select embodiments, segmentation is not necessary and data are directly displayed using the grayscale image information. Optionally, a 3-D representation of the cartilage, cortical bone, trabecular bone, subchondral bone, cut bone, menisci, and/or other anatomic structures as well as the articular repair system is generated, for example, using a polygon or non-uniform rational B-spline (NURBS) surface or other parametric surface representation. For a description of various parametric surface representations see, for example, Foley, J. D. et al., Computer Graphics: Principles and Practice in C; Addison-Wesley, 2nd edition (1995).

The 3D representations of the cartilage, cortical bone, trabecular bone, subchondral bone, cut bone, menisci, and/or other anatomic structures and the articular repair system can be merged into a common coordinate system. The articular repair system can then be placed at the desired implantation site. The representations of the cartilage, cortical bone, trabecular bone, subchondral bone, cut bone, menisci, and/or other anatomic structures and the articular repair system can be rendered into a 3-D image in application programming interfaces (APIs), such as, for example, OpenGL® (standard library of advanced 3-D graphics functions developed by SG, Inc.; available as part of the drivers for PC-based video cards, for example from www.nvidia.com for NVIDIA video cards or www.3dlabs.com for 3Dlabs products, or as part of the system software for Unix workstations) or DirectX® (multimedia API for Microsoft Windows® based PC systems; available from www.microsoft.com). The 3-D image can be rendered showing the cartilage, cortical bone, trabecular bone, subchondral bone, cut bone, menisci and/or other anatomic objects and the articular repair system from varying angles, e.g., by rotating or moving them interactively or non-interactively, in real-time or non-real-time.

In various embodiments, articular repair systems (e.g., including resection cut strategy, guide tools, and implant components) can be formed or selected to achieve various parameters including a near anatomic fit or match with the surrounding or adjacent cartilage, subchondral bone, menisci and/or other tissue. The shape of the repair system can be based on the analysis of an electronic image. If the articular repair system is intended to replace an area of diseased cartilage or lost cartilage, the near anatomic fit can be achieved using a method that provides a virtual reconstruction of the shape of healthy cartilage in an electronic image.

Virtual and Physical Models

In certain embodiments, models can be generated to show defects of interest in a patient's joint. Computer software programs to generate models of patient-specific renderings of implant assembly and defects (e.g., osteophyte structures), together with bone models, to aid in surgery planning can be developed using various publicly available programming environments and languages, for example, Matlab 7.3 and Matlab Compiler 4.5, C++ or Java. In certain embodiments, the computer software program can have a user interface that includes, for example, one or more of the components including a 3D render canvas, a data path selector, an ID listbox, a report views selection, a scan selection, a generate report button, a generate views button, an image display, and an image slice slider. Alternatively, one or more off-the-shelf applications can be used to generate the models, such as SolidWorks, Rhinoceros, 3D Slicer or Amira.

If desired, in various embodiments a patient-specific bone-surface model can be obtained and/or rendered. The bone surface model can provide basic patient-specific features of the patient's biological structure and serve as a reference for comparison against a model or value that includes the defect(s) of interest. As an illustrative example, previously generated patient-specific files, for example, STL files exported from "SOLID" ICES files in SolidWorks, can be loaded as triangulation points with sequence indices and normal vectors. The triangles then can be rendered (e.g., using Matlab TRISURF function) to supply or generate the bone-surface model. The bone surface model can include corrections of defects, such as osteophytes removed from the bone. In a similar fashion, one or more guide tool models can be obtained and/or rendered.

If desired, models can be used to detect interference between any defect volume and the placement of one or more guide tools and/or implant components. For example, guide tool model triangulation points can be transformed onto an image volume space to obtain a binary representation of the guide tool. The binary structure then can be manipulated (e.g., dilated and eroded using voxel balls having pre-set diameters) to obtain a solid field mask. The solid field mask can be compared against the defect volume, for example, the osteophyte binary volume, to identify interfering defect volume, for example, interfering osteophyte binary volume. In this way, interfering defect volume and non-interfering defect volume can be determined (e.g., using Matlab ISOSURFACE function), for example, using representative colors or some other distinguishing features in a model. The resulting model image can be rendered on a virtual rendering canvas (e.g., using Matlab GETFRAME function) and saved onto a computer-readable medium.

Deformity Correction and Optimizing Limb Alignment

In certain embodiments, the degree of deformity correction that is necessary to establish a desired limb alignment can be calculated based on information from the alignment of a virtual model of a patient's limb. The virtual model can be generated from patient-specific data, such 2D and/or 3D imaging data of the patient's limb. The deformity correction can correct varus or valgus alignment or antecurvatum or recurvatum alignment. In a preferred embodiment, the desired deformity correction returns the leg to normal alignment, for example, a zero degree biomechanical axis in the coronal plane and absence of genu antecurvatum and recurvatum in the sagittal plane, or various other user-defined alignment(s) can be designated and obtained.

Once the proper and/or desired alignment of the patient's extremity has been determined virtually, one or more surgical steps (e.g., resection cuts) may be planned and/or accomplished, which may include the use of surgical tools (e.g., tools to guide the resection cuts), and/or implant components (e.g., components having variable thicknesses to address misalignment). Various features of the patient-adapted implant components and/or the planned surgical steps, including bone cut angles, bone cut slopes, bone cut number, implant thickness in one or more portions, joint facing curvature, implant component thickness, and other features, can be selected and/or designed, at least in part, to optimize the parameter of deformity correction and/or limb alignment, for example, using the virtual alignment method described herein. Optionally, one or more other parameters can simultaneously be factored into the selection and/or design of implant component features and/or surgical procedure. For example, in addition to limb alignment, the implant component and/or surgical procedure features also can be selected or designed meet one or more of the following parameters: (1) preserving, restoring, or enhancing the patient's joint kinematics; (2) deformity correction; (3) maximizing preservation of bone cartilage, or ligaments (e.g., resulting from the resection); (4) maximizing preservation and/or optimization of other features of the patient's anatomy, such as trochlea and trochlear shape; (5) restoration or optimization of joint-line location and/or joint gap width, and (6) preservation, restoration, or enhancement of other target features.

If desired, an implant design can alter the kinematics of the patient knee as desired, such as, for example, by altering a condyle location and/or surface to alter the implant motion and ultimately the kinematics of the patient's limb. In a similar manner, a surgical procedure plan can include modified resection and bone cut planes that reposition and/or reorient the various surfaces of a predetermined implant design, thereby altering the location and/or orientation of articulating surfaces of a condyle implant to desirably alter the implant motion and ultimately the kinematics of the patient's limb.

Matching to Reference Databases

In various embodiments, one or more measured anatomical features may be modeled, derived and/or modified using information from one or more reference databases. For example, existing patient information can be obtained from patient measurements through the various methods described herein. Such information can include various information regarding a targeted femur, tibia and patella of a targeted knee joint, which in this case includes information regarding the patient's femoral/tibial/patellar shape, length, width, condyle dimensions, features and slopes, angles, e.g., trochlear angles, Q angle, trochlea characteristics, tibial characteristics, tibial tuberosity, medial/lateral slopes, tibial spine height, coronal curvatures, sagittal curvatures and general joint dimensions, as well as any number of biomechanical or kinematic parameters as described in the various sections and Tables herein as well as those known in the art. The information can also include anatomical and biomechanical axes, angles and other information from the patient's opposing joint and well as information regarding adjacent joint structures (i.e., hip and/or ankle information) from the treated leg or the opposing leg or both. Additional information collected can include body weight, race, gender, activity level, health conditions, other disease or medical conditions, etc. If desired, weighting parameters may be assigned to various measurements or series of measurements (or other collected or derived information), as well as to one or more joint surfaces, including opposing joint surfaces.

Various disclosed embodiments contemplate utilizing various of the collected and/or derived patient-specific information (as well as any optional weighting parameters), which methods can include identifying one or more "matching subjects" from one or more reference databases, comparing features from the matching subject to the patient-specific information, and optionally creating a comparison or "weighting score" to evaluate and display the results of the various comparisons (relative to individual feature comparisons and/or an overall composite score for the comparison of each subject). The databases can comprise information from various sources, including cadaveric data, imaging, biomechanical or kinematic data, historic data and/or data regarding previous knee implant cases from various manufacturers, including ConforMIS-specific case data. Such data can be specific to gender, age, weight, health, size, etc., or can be selected based on weighting (as previously described) or other criteria.

Next, the method manually or automatically selects one or more anatomic shapes or features from one or more matching subjects to create one or more "derived anatomic matches" and/or to modify the patient-specific data. The "derived anatomic matches" may comprise the features from one or more subjects, or may comprise a composite anatomy derived from such shapes and/or subjects (which may also be identified and/or derived utilizing a weighting score, if desired). In addition, or if place of, this step, the method may utilize the matching subject data to normalize or "smooth" the patient-specific data and/or model, which can desirably correct or normalize the patient-specific data and potentially correct the patient-specific data for inherent deformities like osteophytes, axis deformity and/or cartilage degradation.

In various alternative embodiments, one or more databases may be created that include anatomical information of multiple individuals, with preplanned surgical steps/tools and/or pre-designed implant components associated with relevant anatomical information. The associated information may be compiled from records of previous surgeries and/or may be created by designers and/or physicians using patient anatomical information from specific patients and/or from general population groups and/or averages. If desired, an automated and/or semi-automated system may search these one or more databases using various data from a prospective patient (utilizing one or more of any data sources described herein, including actual anatomical data, variations, reference points and features and/or models) and identify one or more matches (or other relationships, such as similarities of various relevant component features of individual anatomy) to one or more individuals. The preplanned surgical steps/tools and/or pre-designed implant components associated with such anatomy may then be assessed, evaluated, rated and/or combined (if desired), and the resulting information may be utilized to design and/or select an appropriate implant and surgical plan/tools for the prospective patient.

Using Parameters to Assess Implants, Tools and Procedures

Correcting a joint deformity and/or a limb alignment deformity can include, for example, generating a virtual model of the patient's joint, limb, and/or other relevant biological structure(s); virtually correcting the deformity and/or aligning the limb; and selecting and/or designing one or more surgical steps (e.g., one or more resection cuts), one or more guide tools, and/or one or more implant components to physically perform and/or accommodate the correction.

Certain embodiments described herein include generating and/or using a model, for example, a virtual model, of the patient's joint that includes selected parameters and/or parameter measurements and virtually selecting and/or designing one or more implant components, and optionally resection cuts and/or guide tools to fit the virtual model in accordance with the selected parameters and/or parameter measurements. This approach allows for iterative selection and/or design improvement and can include steps to virtually assess fit relative to the selected parameters and/or parameter measurements, such as (1) correction of a joint deformity; (2) correction of a limb alignment deformity; (3) preservation of bone, cartilage, and/or ligaments at the joint; (4) preservation, restoration, or enhancement of one or more features of the patient's biology, for example, trochlea and trochlear shape; (5) preservation, restoration, or enhancement of joint kinematics, including, for example, ligament function and implant impingement; (6) preservation, restoration, or enhancement of the patient's joint-line location and/or joint gap width; and (7) preservation, restoration, or enhancement of other target features.

Software for Testing/Verification of Component Suitability

In various embodiments, it is important to ensure that optimization, correction and/or modifications of the joint, implant, tools and/or procedure in one given manner do not adversely and/or unacceptably affect the implant components or joint in some other manner. In various embodiments, this cross-checking or cross-referencing of proposed individual modifications to the joint, implant, tools and/or surgical procedure can be accomplished using software and automated and/or semi-automated systems.

For example, an implant component may be selected and/or adapted in shape so that it stays clear of (i.e., avoids incidental and/or long-term contact with) important ligament structures (either or both during the surgical insertion procedure as well as after implantation). Imaging data can help identify or derive shape or location information on such ligamentous structures.

As will be appreciated by those of skill in the art, the process of selecting and/or designing an implant component feature and/or feature measurement, resection cut feature and/or feature measurement, and/or guide tool feature and/or feature measurement can be tested against the information obtained regarding the patient's biological features and/or other models, for example, from one or more MRI or CT or x-ray images from the patient, to ensure that the features and/or feature measurements are optimum with respect to the selected parameter targets or thresholds. Testing can be accomplished by, for example, superimposing the implant image over the image for the patient's joint. In a similar manner, load-bearing measurements and/or virtual simulations thereof may be utilized to optimize or otherwise alter a derived implant design. For example, where a proposed implant for a knee implant has been designed, it may then be virtually inserted into a biomechanical model or otherwise analyzed relative to the load-bearing conditions (or virtually modeled simulations thereof) it may encounter after implantation. These conditions may indicate that one or more features of the implant are undesirable for varying reasons (i.e., the implant design creates unwanted anatomical impingement points, the implant design causes the joint to function in an undesirable fashion, the joint design somehow interferes with surrounding anatomy, the joint design creates a cosmetically-undesirable feature on the repaired limb or skin covering thereof, FEA or other loading analysis of the joint design indicates areas of high material failure risk, FEA or other loading analysis of the joint design indicates areas of high design failure risk, FEA or other loading analysis of the joint design indicates areas of high failure risk of the supporting or surrounding anatomical structures, etc.). In such a case, such undesirable features may be accommodated or otherwise ameliorated by further design iteration and/or modification that might not have been discovered without such analysis relative to the "real world" measurements and/or simulation.

Such load-bearing/modeling analysis may also be used to further optimize or otherwise modify the implant design, such as where the implant analysis indicates that the current design is "over-engineered" in some manner than required to accommodate the patient's biomechanical needs. In such a case, the implant design may be further modified and/or redesigned to more accurately accommodate the patient's needs, which may have an unintended (but potentially highly-desirable) consequence of reducing implant size or thickness, reducing the required amount of bony support material removal, increasing or altering the number and/or type of potential implant component materials (due to altered requirements for material strength and/or flexibility), increasing estimate life of the implant, reducing wear and/or otherwise altering one or more of the various design "constraints" or limitations currently accommodated by the present design features of the implant and/or surgical procedure.

In various embodiments, a finite element analysis can be conducted on device components as one parameter in the optimization of the features of an implant, which can include analyses of multiple or "competing" potential designs for a given implant component. In various alternative embodiments, implant components such as a tibial tray can comprise sections of varying thickness. If desired, the modeling software may conduct FEA or other load analysis on the tibial tray (incorporating various patient-specific information, including patient weight and intended activity levels, among other factors) and determine if specific areas of the intended implant design at are an undesirable risk of failure or fatigue. Such areas can be reinforced, thickened or otherwise redesigned (if desired) to accommodate and/or alleviate such risks (desirably before actual manufacture of the implant). In a similar manner, areas of lower stress/fracture risk can be redesigned (if desired) by removal of material, etc., which may improve the fit and/or performance of the implant in various ways. Of course, either or both of the upper and lower surfaces of the tibial tray may be processed and/or redesigned in this manner.

Software and Data Libraries

Data and models can be collected in one or more libraries for subsequent use for the same patient or for a different patient (e.g., a different patient with similar data). In certain embodiments, a library can be generated to include images from a particular patient at one or more ages prior to the time that the patient needs a joint implant. For example, a method can include identifying patients eliciting one or more risk factors for a joint problem, such as low bone mineral density score, and collecting one or more images of the patient's joints into a library. In certain embodiments, all patients below a certain age, for example, all patients below 40 years of age can be scanned to collect one or more images of the patient's joint. The images and data collected from the patient can be banked or stored in a patient-specific database. For example, the articular shape of the patient's joint or joints can be stored in an electronic database until the time when the patient needs an implant. Then, the images and data in the patient-specific database can be accessed and a patient-specific and/or patient-engineered partial or total joint replacement implant using the patient's original anatomy, not affected by arthritic deformity yet, can be generated. This process results in a more functional and more anatomic implant.

In a similar manner, pre-existing implant designs and/or implant components can be selected from, catalogued in, and/or stored in a library. The library can include a virtual library of implants, or components, or component features that can be combined and/or altered to create a final implant. The library can include a catalogue of physical implant components. In certain embodiments, physical implant components can be identified and selected using the library. The library can include previously-generated implant components having one or more patient-adapted features, and/or components with standard or blank features that can be altered to be patient-adapted. Accordingly, implants and/or implant features can be selected from the library.

A virtual or physical implant component can be selected from the library based on similarity to prior or baseline parameter optimizations, such as one or more of (1) deformity correction and limb alignment (2) maximum preservation of bone, cartilage, or ligaments, (3) preservation and/or optimization of other features of the patient's biology, such as trochlea and trochlear shape, (4) restoration and/or optimization of joint kinematics, and (5) restoration or optimization of joint-line location and/or joint gap width. Accordingly, one or more implant component features, such as (a) component shape, external and/or internal, (b) component size, and/or (c) component thickness, can be determined precisely and/or determined within a range from the library selection. Then, the selected implant component can be designed or engineered further to include one or more patient-specific features.

Accordingly, in certain embodiments an implant can include one or more features designed patient-specifically and one or more features selected from one or more library sources. For example, in designing an implant for a total knee replacement comprising a femoral component and a tibial component, one component can include one or more patient-specific features and the other component can be selected from a library.

The process can include generating and/or using a model, for example, a virtual model, of the patient's joint that includes the selected measurements and virtually fitting one or more selected and/or designed implants into the virtual model. This approach allows for iterative selection and/or design improvement and can include steps to virtually assess the fit, such as virtual kinematics assessment.

Modeling and Uses of Blanks and Blank Libraries

If desired, various components may be constructed as a "standard" or "blank" in various sizes or may be specifically formed for each patient based on their imaging data and anatomy. Computer modeling may be used and a library of virtual standards may be created for each of the components. A library of physical In various embodiments, the surgical alteration can be simulated on a computer and the insert blank can then be shaped based on the result of the simulation.

Surgical Repair and Kinematics Optimization

The modeling of a patient's anatomy, and the surgical repair and/or replacement of a patient's anatomical features, provides the surgeon and implant manufacturers with an opportunity to modify, correct and/or otherwise optimize/enhance at least a portion of the patient's anatomy. Many of the embodiments described herein relate to improvements, alterations, optimizations and/or modifications to the patient's biological features and/or to articular repair systems (including implant components, tools/jigs and/or surgical procedures), with an ultimate objective being the modification of and/or improvement to joint and/or extremity alignment and/or kinematics. Various embodiments include implant components that incorporate various patient-engineered features optimized from patient-specific data. Such patient-engineered features can include (but are not limited to) one or more implant component surfaces, such as surface contours, angles or bone cuts, and dimensions, such as thickness, width, depth, or length of one or more aspects of the implant component. Some embodiments can include alterations or modifications to surgical tools/jigs and/or various surgical procedure steps to modify the underlying anatomical support surfaces in one or more desirable manners. Additional embodiments can include inserts, spacers or other components to modify and/or enhance the positioning, orientation and/or performance of the implant, as well as the performance, kinematics and/or alignment of the joint and/or extremity. Various combinations of the above embodiments are contemplated as well, with varying results.

Preservation or restoration of the patient's joint kinematics can include, for example, selecting and/or designing one or more surgical steps (e.g., one or more resection cuts), one or more guide tools, and/or one or more implant components so that the patient's post-operative joint kinematics substantially match the patient's pre-operative joint kinematics and/or substantially match the patient's healthy joint kinematics (e.g., as identified from previous images of the patient's joint when it was healthy or from an image of the patient's contralateral healthy joint).

Enhancing the patient's joint kinematics can include, for example, selecting and/or designing one or more surgical steps (e.g., one or more resection cuts), one or more guide tools, and/or one or more implant components that provide healthy joint kinematics estimated for the particular patient and/or that provide proper joint kinematics to the patient. Optimization of joint kinematics also can include optimizing ligament loading or ligament function during motion.

Enhancing the patient's joint-line location and/or joint gap width can include, for example, selecting and/or designing one or more surgical steps (e.g., one or more resection cuts), one or more guide tools, and/or one or more implant components that provide a healthy joint-line location and/or joint gap width and/or estimated for the particular patient and/or that provide proper kinematics to the patient.

Patient Anatomy Modeling

As described herein, a computer program or other automated processing equipment can be utilized in effectuating the various methods and systems described herein. An initial step in assessing one or more anatomical features of a patient is to obtain information about the size, shape and/or condition of the relevant patient anatomy. For an orthopedic implant, this process typically includes obtaining one or more images of the patient's joint and/or other relevant patient anatomy (i.e., adjacent anatomical areas and/or other features of interest) using, for example, non-invasive imaging modalities or scans (including those previously described, as well as those known in the art). The raw electronic image data can be used to create one or more representations or "models" of the patient's anatomy. These representations can include electronic and/or virtual models as well as 2-Dimensional images and/or 3-Dimensional physical reproductions of the patient anatomy.

In various embodiments, the models can include anatomic reference points and/or limb alignments, including alignment angles within the same and between different joints as well as comparisons to simulated normal limb alignment(s). Any anatomic features, including those related to alignment and/or misalignment, can be selected and imaged. For example, in certain embodiments, such as for a knee or hip implant, the imaging test can include data from at least one of, or several of, a hip joint, knee joint and ankle joint. The imaging test can be obtained in lying, prone, supine or standing position. The imaging test can include only the target joint, or both the target joint and also selected data through one or more adjoining joints as well as data from opposing joints and/or structures adjacent thereto.

The models (as well as the raw anatomical information) can be used to simulate biomotion of one or more joints and/or extremities, such as a knee joint, or a knee and ankle joint, or a hip, knee and/or ankle joint. In various embodiments, the computer can model the existing patient anatomy for various uses, including (1) to create patient-specific imaging data and/or models thereof, (2) to identify deficiencies in the existing anatomy, (3) to determine if replication of the existing patient anatomy would create a desired or acceptable outcome for the joint repair/replacement procedure, (4) to derive, identify and/or plan modifications or alterations to the existing anatomy to create one or more desired anatomical features for the patient's anatomy, (5) to design joint repair/replacement implant components, surgical tools and surgical procedures for treating the relevant patient anatomy, and/or (6) to plan surgical repair and replacement procedures for display to and/or further use by surgeons and/or patients.

Various additional information can be incorporated into the model(s), including patient-specific kinematic data, such as obtained in a gait lab. If desired, patient-specific navigation data, for example generated using a surgical navigation system, image guided or non-image guided can be fed into the computer program. This kinematic or navigation data can, for example, be generated by applying optical or RF markers to the limb and by registering the markers and then measuring limb movements, for example, flexion, extension, abduction, adduction, rotation, and other limb movements. Optionally, other data including anthropometric data may be added for each patient. These data can include but are not limited to the patient's age, gender, weight, height, size, body mass index, and race. Desired limb alignment and/or deformity correction can also be added into the model.

A patient-specific biomotion model can be derived that includes combinations of parameters listed above. The biomotion model can simulate various activities of daily life including normal gait, stair climbing, descending stairs, running, kneeling, squatting, sitting and any other physical activity. The biomotion model can start out with standardized activities, typically derived from reference databases. These reference databases can be, for example, generated using biomotion measurements using force plates and motion trackers using radiofrequency or optical markers and video equipment. If desired, the biomotion model can subsequently be modified and/or queried by the inclusion of patient-specific activities, such as golfing, mountain climbing, swimming, scuba diving, etc.

In addition to (or in place of) the above-mentioned measurements, it may be desirable to obtain measurements of the targeted joint (as well as surrounding anatomical areas and or other joints of the patient's anatomy) in a load-bearing or otherwise "real-world" condition. Such measurements can potentially yield extremely useful data on the alignment and/or movement of the joint and surrounding structures (as well as the loading conditions of the various joint components)—information which may be difficult to obtain or model from standard imaging techniques (i.e., sitting or lying X-rays, CT-scans and/or MRI imaging). Such load-bearing measurements can include imaging of the patient standing, walking and/or carrying loads of varying sizes and/or weights.

It may also be desirable to model various of the patient measurements (especially non-load-bearing measurements as described above) to simulate the targeted joint and surrounding anatomy virtually. Such simulations can include virtually modeling the alignment and load bearing condition of the joint and surrounding anatomical structures for the patient standing and/or moving (i.e., walking, running, jumping, squatting, kneeling, walking up and down stairs or inclines/declines, picking up objects, etc.). Such simulations can be used to obtain valuable anatomical, biomechanical and kinematic data including the loaded condition of various joint components, component positions, component movement, joint and/or surrounding tissue anatomical or biomechanical constraints or limitations, as well as estimated mechanical axes in one or more directions (i.e., coronal, sagittal or combinations thereof). This information could then be utilized (alone or in combination with other data described herein) to design various features of a joint resurfacing/replacement implant. This method can be incorporated in the various embodiments described herein as additional patient measurement and anatomical/joint modeling and design data. This analysis is applicable to many different joints, including a medial condyle, a lateral condyle, a trochlea, a medial tibia, a lateral tibia, the entire tibia, a medial patella, a lateral patella, an entire patella, a medial trochlea, a central trochlea, a lateral trochlea, a portion of a femoral head, an entire femoral head, a portion of an acetabulum, an entire acetabulum, a portion of a glenoid, an entire glenoid, a portion of a humeral head, an entire humeral head, a portion of an ankle joint, an entire ankle joint, and/or a portion or an entire elbow, wrist, hand, finger, spine or facet joint.

The biomotion model can then be individualized with use of patient-specific information including at least one of, but not limited to the patient's age, gender, weight, height, body mass index, and race, the desired limb alignment or deformity correction, and the patient's imaging data, for example, a series of two-dimensional images or a three-dimensional representation of the joint for which surgery is contemplated.

Modeling and Model Correction/Modification

At any point in the design and/or selection procedure, including any point before or after initial design and/or selection of implant components, tools and/or surgical procedure planning has been completed, biomotion models for a particular patient can be supplemented with patient-specific finite element modeling, kinematic modeling and/or other biomechanical models known in the art. Anticipated motion and/or resultant forces in the knee joint can be calculated for each component or combination of components for each specific patient. The implant and/or surgical procedure can be engineered to the patient's load and force demands. For instance, in one embodiment a patient weighing 125 lbs. may not need a tibial plateau as thick as a patient weighing 280 lbs. Similarly, the polyethylene can be adjusted in shape, thickness and material properties for each patient. For example, a 3 mm polyethylene insert can be used in a light lite patient with low force, and a heavier or more active patient may need an 8 mm polymer insert or similar device. Such considerations may require and/or recommend changes to the initially designed and/or selected implant components, tools and/or surgical procedure steps.

From a three-dimensional perspective, the lower extremity of the body ideally functions within a single plane known as the median anterior-posterior plane (MAP-plane) throughout the flexion-extension arc. In order to accomplish this, the femoral head, the mechanical axis of the femur, the patellar groove, the intercondylar notch, the patellar articular crest, the tibia and the ankle will desirably remain within the MAP-plane during the flexion-extension movement. During movement, the tibia rotates as the knee flexes and extends in the epicondylar axis, which is perpendicular to the MAP-plane.

Using Kinematics to Plan Implants/Procedure Steps

Once one or more reference points, measurements, structures, surfaces, models, or combinations thereof have been determined, selected, varied, deformed, altered or derived, the resulting models and/or features can be used to select and/or design one or more implant components having an ideal or optimized feature or shape, e.g., corresponding to the measured, deformed, altered and/or corrected joint feature(s) or shape(s). For example, one application of this embodiment could create an ideal or optimized implant shape that reflects the shape of the patient's joint before he or she developed arthritis.

In various embodiments, the comparison, analysis and/or modifications may include modification of one or more patient-specific features and/or design criteria for the implant to account for any underlying deformity reflected in the patient-specific measurements. If desired, the modified data may then be utilized to choose or design an appropriate implant to match the modified features, and a final verification operation may be accomplished to ensure the chosen implant is acceptable and appropriate to the original unmodified patient-specific measurements (i.e., the chosen implant will ultimately "fit" the original patient anatomy). In alternative embodiments, the various anatomical features may be differently "weighted" during the comparison process (utilizing various formulaic weightings and/or mathematical algorithms), based on their relative importance or other criteria chosen by the designer/programmer and/or physician.

Figure 5:
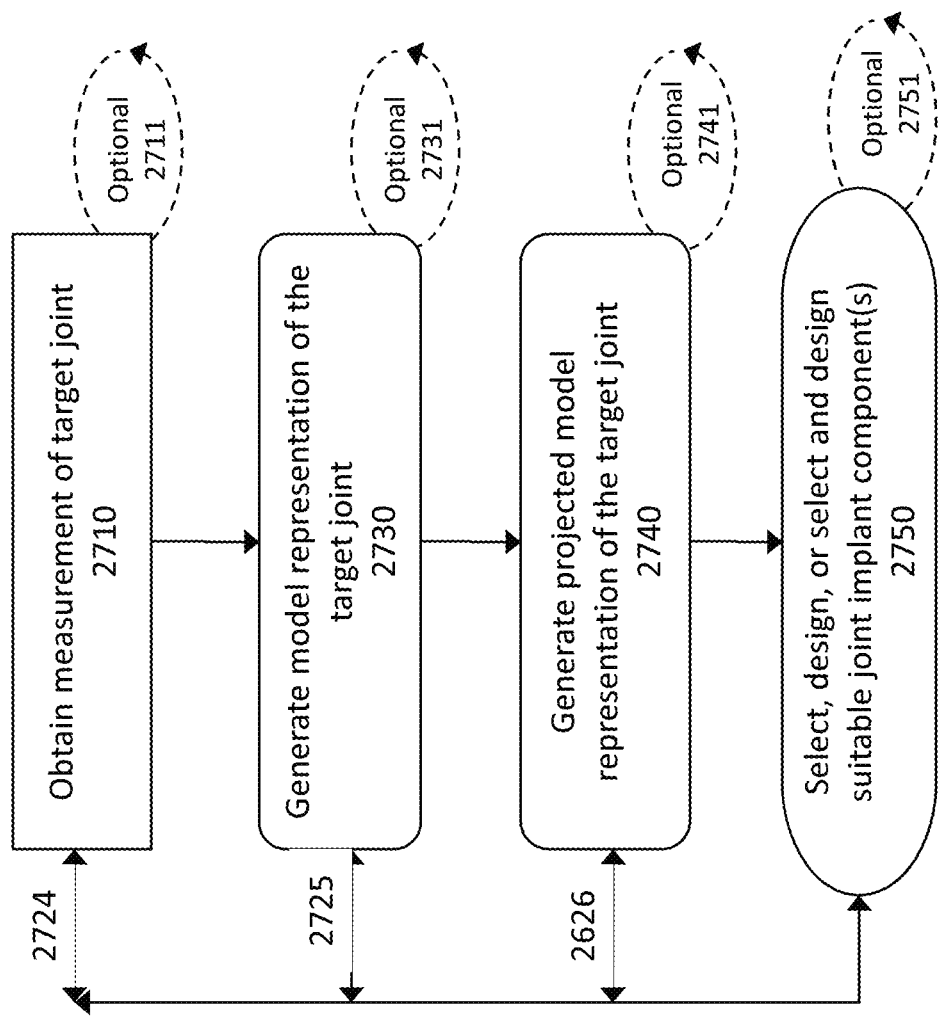
FIG. 5 is an illustrative flow chart showing exemplary steps taken by a practitioner in assessing a joint and selecting and/or designing a suitable replacement implant component.
Figure 6:
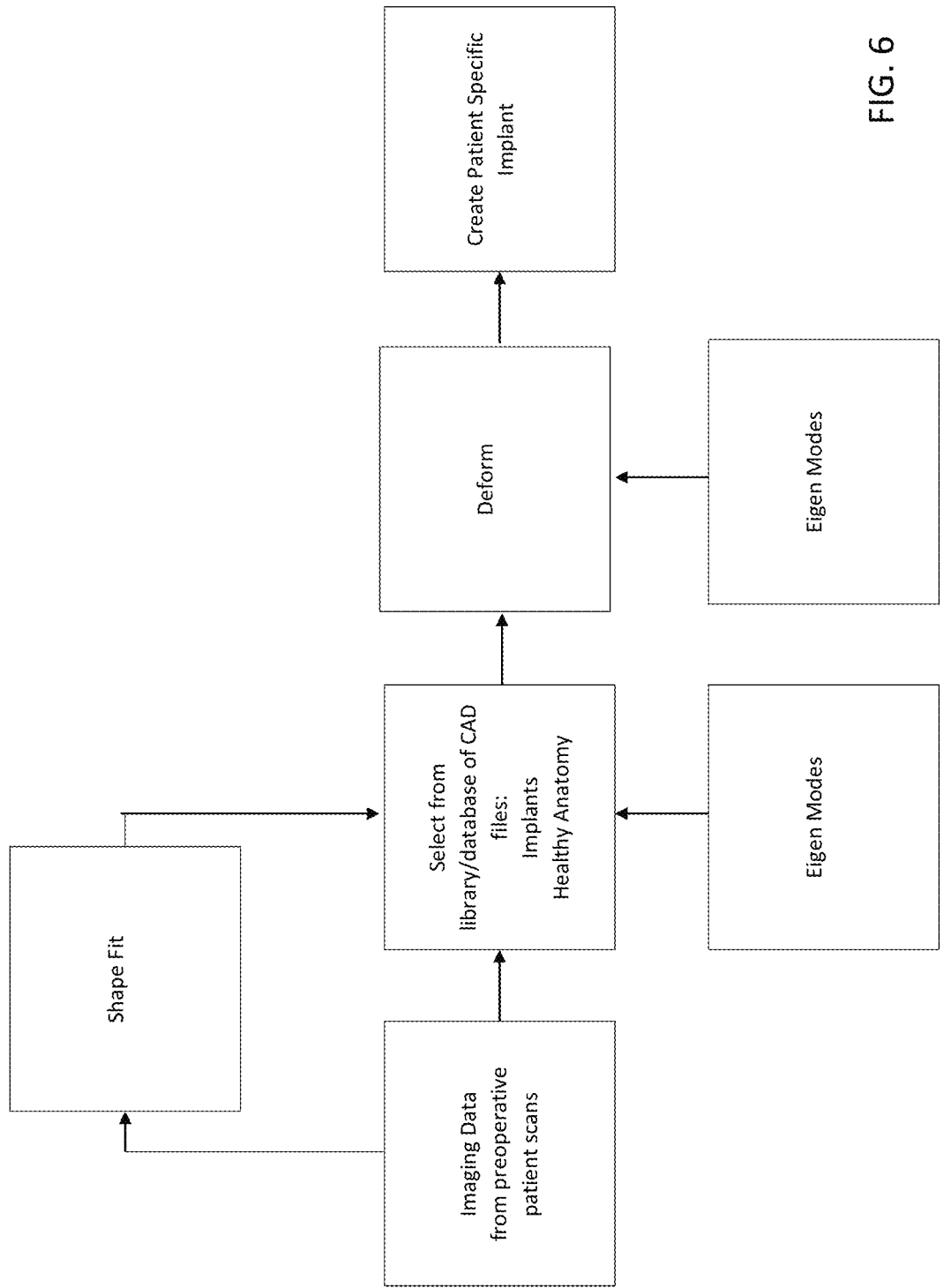
FIG. 6 is a flowchart depicting an exemplary embodiment for using eigen modes to select and deform implant designs to create a patient-specific implant.
Figure 7:
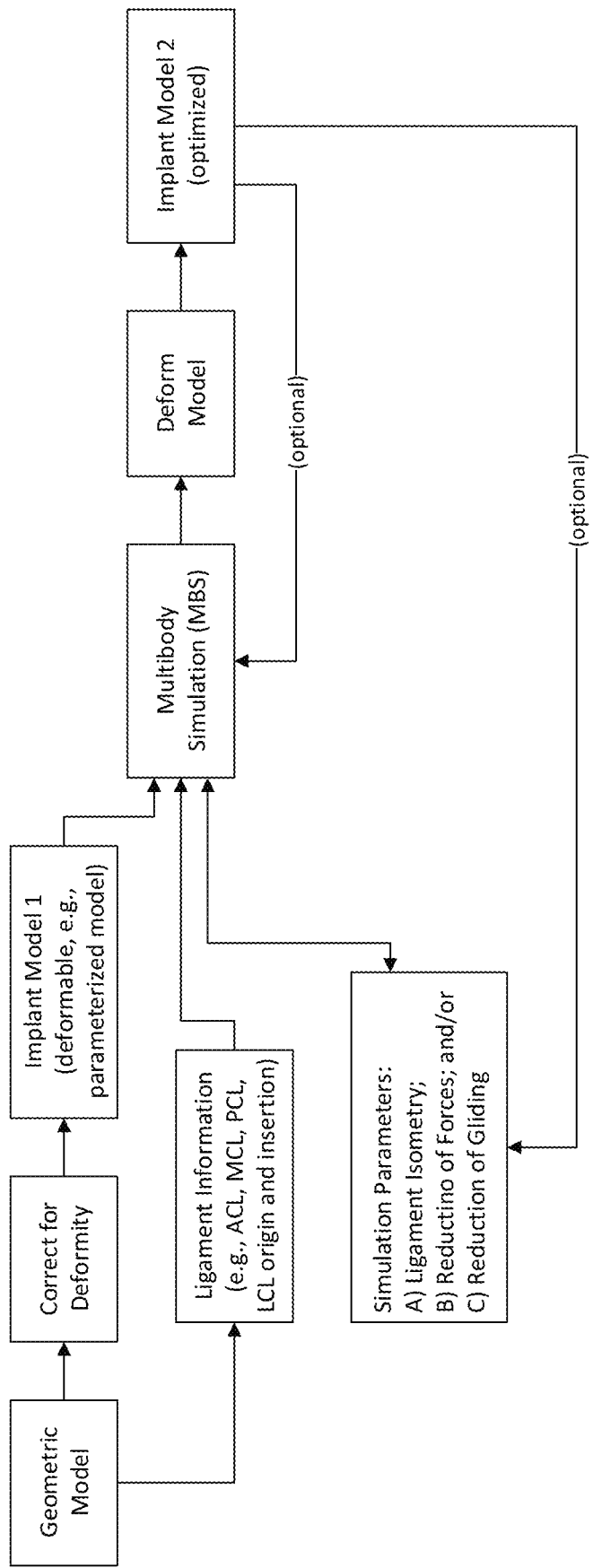
FIG. 7 is a flowchart depicting an exemplary embodiment for employing multibody simulation to optimize kinematics of an implant model.
Figure 8:
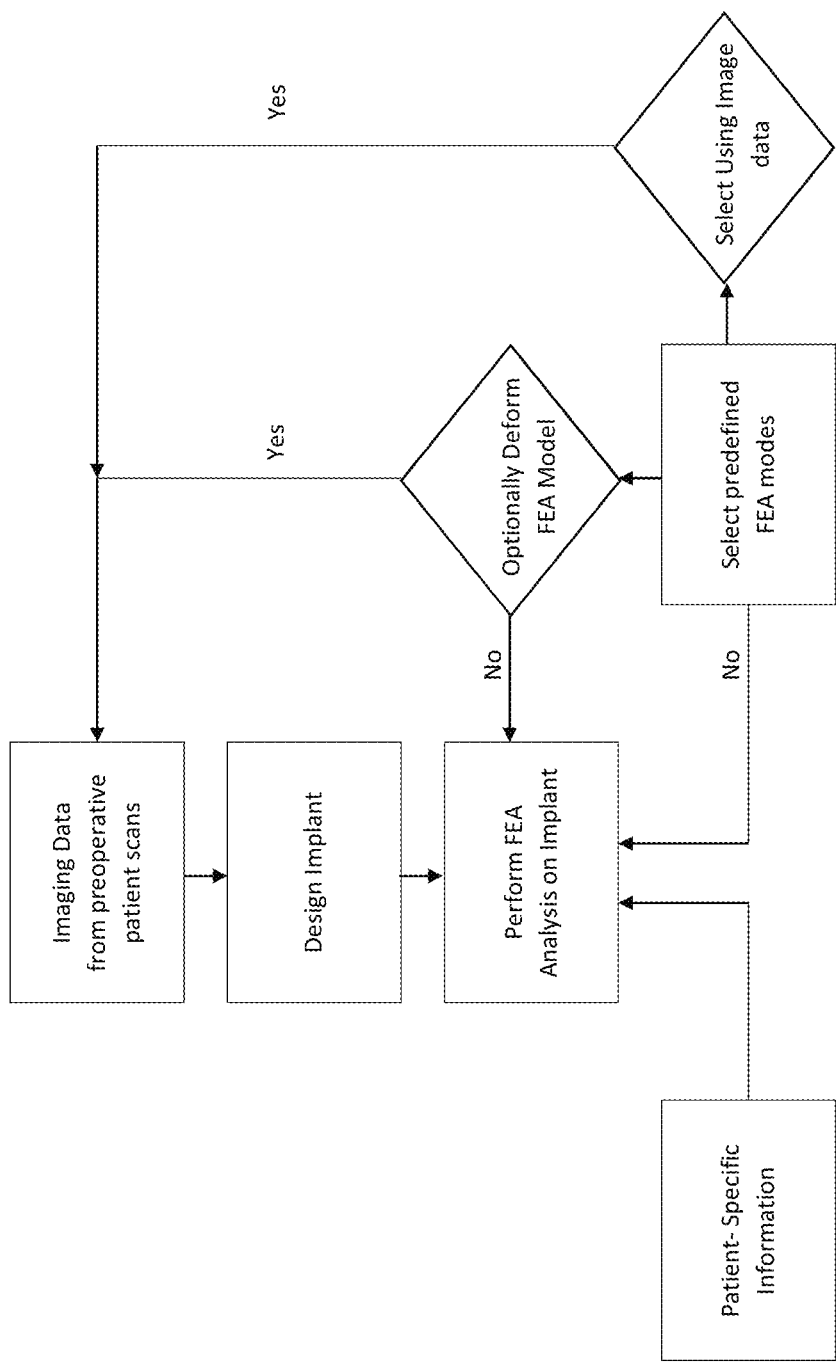
FIG. 8 is a flowchart depicting an exemplary embodiment for performing a FEA analysis on an implant design.
Figure 9:
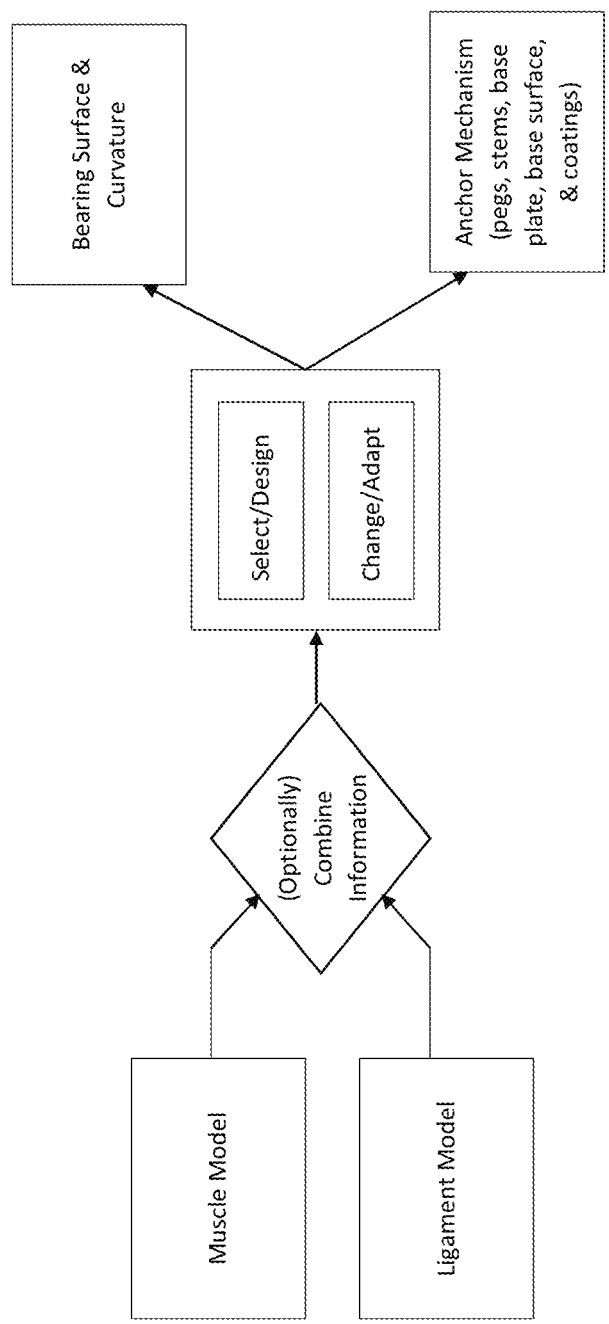
FIG. 9 is a flowchart depicting an exemplary embodiment for using muscle and ligament models to adapt implant component features.
Figure 10:
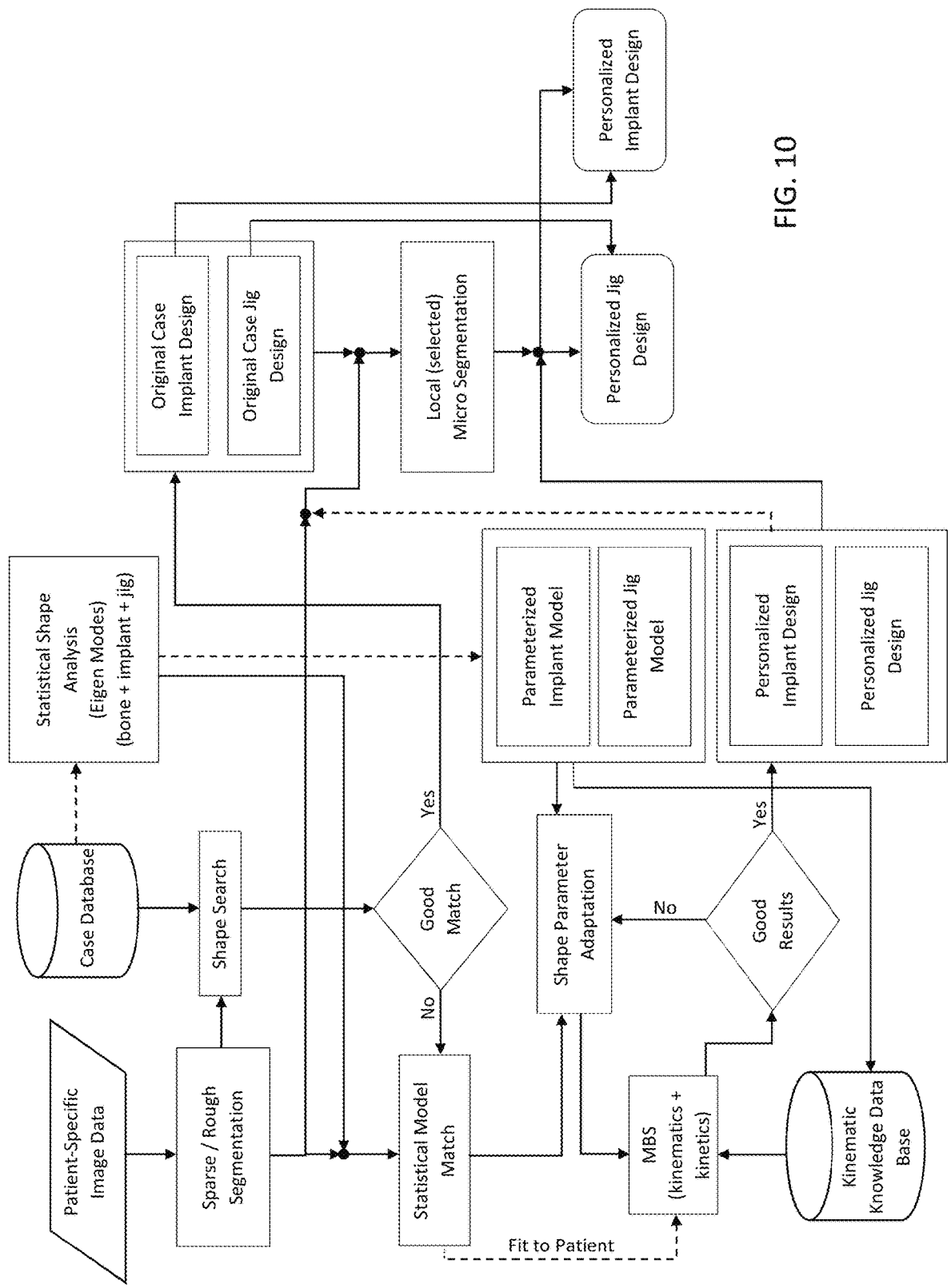
FIG. 10 is a flowchart depicting exemplary embodiments of using shape matching, parameterized models, and/or multibody simulations for selecting and/or designing personalized implant and jig design.
Figure 11:
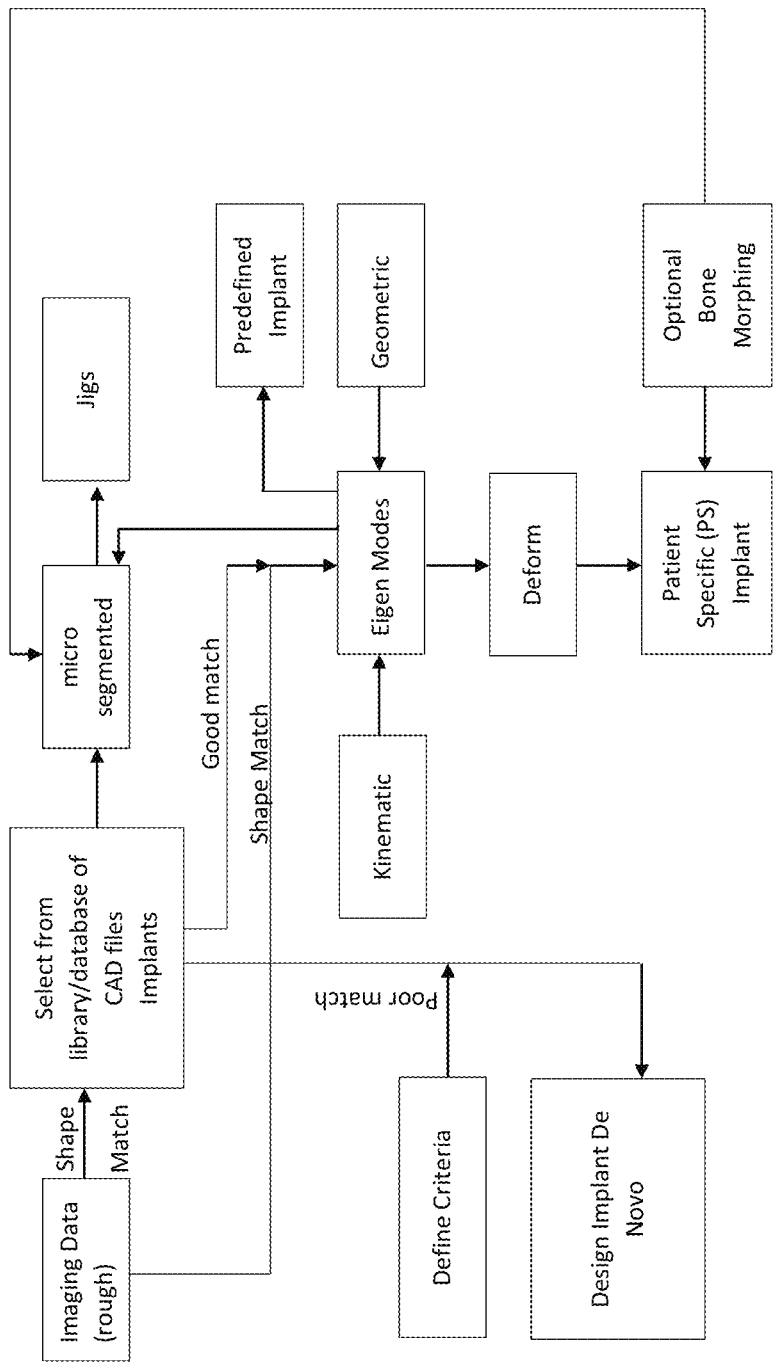
FIG. 11 is a flowchart depicting an exemplary embodiment of using eigen modes to select and/or design an implant.

In various exemplary embodiments, such as shown in FIG. 5, after a model representation of a joint is generated 2730, the practitioner optionally can generate a projected model representation of the target joint in a corrected condition 2740, e.g., based on a previous image of the patient's joint when it was healthy, based on an image of the patient's contralateral healthy joint, based on a projected image of a surface that negatively-matches the opposing surface, based on one or more database images of various patient or population-matched "normal" or "healthy" joints, or various combinations thereof. This step can be repeated 2741, as necessary or as desired. Using the difference between the topographical condition of the joint and the projected image of the joint, the practitioner can then select a joint implant 2750 that is suitable to achieve the corrected joint anatomy. As will be appreciated by those of skill in the art, the selection and/or design process 2750 can be repeated 2751 as often as desired to achieve the desired result. Additionally, it is contemplated that a practitioner can obtain a measurement of a target joint 2710 by obtaining, for example, an x-ray, and then selects a suitable joint replacement implant 2750.

In various embodiments, virtual models of a patient's misaligned lower limb can be virtually corrected. In particular, the patient's lower limb may be misaligned in the coronal plane, for example, a valgus or varus deformity. The deformity correction can be achieved by designing and/or selecting one or more of a resection dimension, an implant component thickness, and an implant component surface curvature that adjusts the mechanical axis or axes into alignment in one or more planes. For example, a lower limb misalignment can be corrected in a knee replacement by designing or selecting one or more of a femoral resection dimension, a femoral implant component thickness, a femoral implant component surface curvature, a tibial resection dimension, a tibial implant component thickness, a tibial implant component insert thickness, and a tibial implant component surface curvature to adjust the femoral mechanical axis and tibial mechanical axis into alignment in the coronal plane.

Information regarding the misalignment and the proper mechanical alignment of a patient's limb can be used to preoperatively design and/or select one or more features of a joint implant and/or implant procedure. For example, based on the difference between the patient's misalignment and the proper mechanical axis, a knee implant and implant surgical procedure can be designed and/or selected preoperatively to include implant and/or resection dimensions that substantially realign the patient's limb to correct or improve a patient's alignment deformity. In addition, the process can include selecting and/or designing one or more surgical tools (e.g., guide tools or cutting jigs) to direct the clinician in resectioning the patient's bone(s) in accordance with the preoperatively designed and/or selected resection dimensions.

In certain embodiments described herein, an implant or implant system can include one, two, three, four or more components having one or more patient-specific features that substantially match one or more of the patient's biological features, for example, one or more dimensions and/or measurements of an anatomical/biological structure, such as bone, cartilage, tendon, or muscle; a distance or space between two or more aspects of a biological structure and/or between two or more different biological structures; and a biomechanical or kinematic quality or measurement of the patient's biology. In addition or alternatively, an implant component can include one or more features that are engineered to optimize or enhance one or more of the patient's biological features, for example, (1) deformity correction and limb alignment (2) preserving bone, cartilage, and/or ligaments, (3) preserving and/or optimizing other features of the patient's anatomy, such as trochlea and trochlear shape, (4) restoring and/or optimizing joint kinematics or biomechanics, and/or (5) restoring and/or optimizing joint-line location and/or joint gap width. In addition, an implant component can be designed and/or manufactured to include one or more standard (i.e., non-patient-adapted) features.

Designing Implants/Procedures to Alter Kinematics

There are several advantages that a patient-specific implant designed and/or engineered to meet or improve one of more of these parameters can have over a traditional implant. These advantages can include, for example: improved mechanical stability of the extremity; improved fit with existing or modified biological features; improved motion and kinematics, and other advantages.

In various embodiments, an implant component (such as a tibial component) can be designed either before or after virtual removal of various features of the underlying anatomical support structure (i.e., a tibial bone) have been accomplished. In one embodiment, the initial design and placement of a tibial tray and associated components can be planned and accomplished utilizing information directly taken from the patient's natural anatomy. In various other embodiments, the design and placement of the tibial components can be planned and accomplished after virtual removal of various bone portions, including the removal of one or more cut planes (to accommodate the tibial implant) as well as the virtual removal of various potentially-interfering structures (i.e., overhanging osteophytes, etc.) and/or the virtual filling of voids, etc. Prior virtual removal/filling of such structures can facilitate and improve the design, planning and placement of tibial components, and prevent anatomic distortion from significantly affecting the final design and placement of the tibial components. For example, once one or more tibial cut planes has been virtually removed, the size, shape and rotation angle of a tibial implant component can be more accurately determined from the virtual surface, as compared to determining the size, shape and/or tibial rotation angle of an implant from the natural tibial anatomy prior to such cuts. In a similar manner, structures such as overhanging osteophytes can be virtually removed (either alone or in addition to virtual removal of the tibial cut plane(s)), with the tibial implant structure and placement (i.e., tibial implant size, shape and/or tibial rotation, etc.) subsequently planned. Of course, virtually any undesirable anatomical features or deformity, including (but not limited to) altered bone axes, flattening, potholes, cysts, scar tissue, osteophytes, tumors and/or bone spurs may be similarly virtually removed and then implant design and placement can be planned.

Kinematic Libraries

As part of the selection and/or design process, a virtual or physical implant component can be selected from a library based on similarity to prior or baseline parameter optimizations, such as one or more of (1) deformity correction and limb alignment (2) maximum preservation of bone, cartilage, or ligaments, (3) preservation and/or optimization of other features of the patient's biology, such as trochlea and trochlear shape, (4) restoration and/or optimization of joint kinematics, and (5) restoration or optimization of joint-line location and/or joint gap width. Accordingly, one or more implant component features, such as (a) component shape, external and/or internal, (b) component size, and/or (c) component thickness, can be determined precisely and/or determined within a range from the library selection. Then, the selected implant component can be designed or engineered further to include one or more patient-specific features. For example, a joint can be assessed in a particular subject and a pre-existing implant design having the closest shape and size and performance characteristics can be selected from the library for further manipulation (e.g., shaping) and manufacturing prior to implantation. For a library including physical implant components, the selected physical component can be altered to include a patient-specific feature by adding material (e.g., laser sintering) and/or subtracting material (e.g., machining).

In certain embodiments, the library could be generated to include images from the particular patient (or a similar patient or patient population) at one or more ages prior to the time that the patient needs a joint implant. Then, the images and data in the patient-specific database can be accessed and a patient-specific and/or patient-engineered partial or total joint replacement implant using the patient's original anatomy, not affected by arthritic deformity yet, can be generated. This process could result in an implant with improved kinematics and/or alignment as compared to the patient's current condition.

Modeling Procedural Steps to Alter Kinematics

In certain embodiments, bone cuts and/or implant shape including at least one of a bone-facing surface of the implant can be designed or selected to achieve normal and/or desired joint kinematics. For example, in certain embodiments, the joint-facing surface of an implant component is designed to match the shape of the patient's articular cartilage. If desired, the joint-facing surface can substantially positively-match one or more features of the patient's existing cartilage surface and/or healthy cartilage surface and/or a calculated cartilage surface, on the articular surface that the component replaces. Alternatively, it can substantially negatively-match one or more features of the patient's existing cartilage surface and/or healthy cartilage surface and/or a calculated cartilage surface, on the opposing articular surface in the joint.

If desired, corrections can be performed to the shape of diseased cartilage by designing surgical steps (and, optionally, patient-adapted surgical tools) to re-establish a normal or near normal cartilage shape that can then be incorporated into the shape of the joint-facing surface of the component. These corrections can be implemented and, optionally, tested in virtual two-dimensional and three-dimensional models. The corrections and testing can include kinematic analysis and/or surgical steps.

Modeling Exemplary Designs to Alter Kinematics

A wide variety of implant component designs and/or selections can be employed to alter, modify and/or optimize the kinematics and/or performance of a patient's joint and joint replacement implant. Moreover, it is often possible to attain a desired extremity alignment through a variety of implant and surgical procedure designs and/or selections. For example, a desired change in the alignment of a knee implant can accomplished by using an implant component specifically designed to create a specific alignment of one or more articulating surfaces. As an alternative approach, surgical resection cuts can be planned such that, in conjunction with a standard implant component, the specific alignment of one or more articulating surfaces of the standard implant can be attained. In a similar manner, a desired alteration of the alignment of medial and lateral condyles of a tibial implant component (relative to a femoral implant component) can be obtained via numerous approaches and techniques, including (1) by increasing the height of the medial component relative to the lateral component, (2) by decreasing the height of the lateral component relative to the medial component, (3) by altering the angle and/or thickness of the tibial tray, (4) by altering the tibial cut surfaces and/or angulations, and (5) by altering the surfaces of the opposing femoral component condyles, etc.

Kinematic Balancing in Various Joints

The use of techniques similar to those discussed herein can be applied to a wide variety of joints, some of which may be modified or altered to varying degrees to account for unique or dissimilar anatomical features. For example, in some embodiments, imaging data can initially be obtained and analyzed, either manually or with computer assistance, to determine the patient specific parameters relevant for placing an implant component in a particular anatomical location. The parameters can include patient specific articular dimensions and geometry and also information about ligament location, size, and orientation, as well as potential soft-tissue impingement, and, optionally, kinematic information for the particular joint or anatomy of interest.

Guide Tools and Surgical Jigs

A variety of traditional guide tools are available to assist surgeons in preparing a joint for an implant, for example, for resectioning one or more of a patient's biological structures during a joint implant procedure. However, these traditional guide tools typically are not designed to match the shape (contour) of a particular patient's biological structure(s). Moreover, these traditional guide tools typically are not designed to impart patient-optimized placement for the resection cuts. Thus, using and properly aligning traditional guide tools, as well as properly aligning a patient's limb (e.g., in rotational alignment, in *varus* or valgus alignment, or alignment in another dimension) in order to orient these traditional guide tools, can be an imprecise and complicated part of the implant procedure.

Kinematic Modeling of Soft Tissues

In an effort to improve the design and/or selection of implant components, tools and/or surgical procedures for a given patient, the accurate modeling and reproduction of in vivo joint kinematics can include the incorporation of soft tissue modeling. Because the constraints provided by soft tissues are very complex in nature, and can include the application of nonlinear force displacement characteristics and axis coupled behavior, inclusion of such information in a joint model can significantly alter the anticipated quantity and direction of loading or other forces that may be experienced by one or more joint resurfacing/replacement implant components over a wide range of joint motion. The proper consideration and/or use of such information has the potential to significantly improve the clinical outcomes of joint arthroplasty procedures.

In various embodiments, a kinematic profile and/or model of a joint can include biomechanical modeling, e.g., of muscles, ligaments and other soft tissues associated with the joint. If desired, this modeling can be in addition to kinematic modeling of the hard tissue structures and/or articulating surfaces of the joint, and such models can include hybrid models incorporating various features of both hard and soft tissue structures. Such "hybrid" biomechanical models can be built with generic information (e.g., related to the muscles, ligaments or other soft tissues), or can include patient-specific information (e.g., information derived from a patient's image data or non-image derived patient-specific information), or various combinations thereof. Such patient-specific image data can include different joint positions, motion imaging and motion analysis. Such non-image derived patient-specific information can include biomechanical properties of the muscles, e.g., contractile response (e.g., force produced or changes in muscle length, width or other dimensions during a contractile response) of the muscles.

A hybrid kinematic model as described herein can include muscle simulations including muscle activation and ligament simulations. The muscle data and/or ligament data can be selected from a pre-existing database. Alternatively, the patient's scan data can be used to introduce muscle data or ligament data of the patient or combinations thereof. For example, the location of a muscle, its width and volume can be introduced into the hybrid kinematic model, for example for purposes of estimating muscle strength and forces. The moment arms can be determined based on the location of the muscles and their tendons. Tendon location, width, length, thickness can be introduced into the hybrid model, for example derived from the patient's scan data. Tendons can be directly visualized on the scan and segmented and introduced into the model. Alternatively, the tendon origin and insertion can be identified on the scan and can be used for kinematic modeling.

In various embodiments, the results of such hybrid kinematic modeling can be utilized to assess and/or modify the design and/or selection of one or more patient-adapted implants, surgical tools and/or surgical procedure plans. For example, a hybrid kinematic model incorporating soft tissue modeling may be utilized to determine a maximum material stress throughout the entirety of a joint implant's range of motion, which may indicate that the implant design is under-designed to accommodate some portion of the anticipated loading. In contrast, a static kinematic model of the same joint and implant components in pure flexion and/or extension (without soft tissue modeling information included) could potentially conclude that the implant component is adequately designed to accommodate the anticipated forces. By including soft tissue modeling, therefore, it can be possible to more accurately estimate the various loading conditions experienced by implant components, and anticipate and/or accommodate undesired loading conditions revealed therewith.

In various embodiments, an implant component position and/or orientation could be adjusted in a hybrid kinematic model to achieve desired post-implantation joint kinematics or biomotion patterns or performance. Bone cuts or reaming or drilling or other surgical interventions could be simulated and/or adjusted to change the implant position, for example in a knee joint, a hip joint or a shoulder joint. The adjustment or optimization of the implant position and orientation and any related surgical interventions could be performed manually, with optionally re-assessment of the kinematic or biomotion pattern or performance after adjustment. The adjustment or optimization of the implant position and orientation and any related surgical interventions could also be performed automatically or semi-automatically, e.g. with optional manual user interaction or input. By utilizing the patient's anatomic information to select an implant and by optionally utilizing the patient's demographic, anatomic, axis, biomechanical and/or hybrid kinematic information, it can be possible to optimize implant placement/position and orientation on one or more articular sides or portions thereof, thereby potentially improving the postoperative kinematic results. In one exemplary embodiment, the optimizations could be focused towards achieving a postoperative, e.g. post implantation, condition for a given patient that would result in a natural or near natural state of joint kinematics or biomotion similar to a health, unoperated state.

In various embodiments, the hybrid kinematic model with one or more implant components incorporated therein could also include information about the patient's bone quality parameters, bone stock, bone shape, cartilage shape, articular curvatures, slopes as well as ligament and muscle information.

In a given hybrid kinematic model, the position and/or orientation of one or more implant components could be adjusted by adjusting the position of one or more patient-adapted guide tools or templates or by adjusting the position of drill guides or cut guides or other guides within these molds or attached to these molds, thereby adjusting the implant position or orientation. Exemplary parameters of implant position or orientation that could be influenced or optimized in this manner could include parameters based on database information, pre-operative scan measurements and/or scan data, as well as intraoperative measurements including, but not limited to:

Implant position, e.g. AP, ML, SI
Implant position to avoid notching, e.g. in knee implants
Implant orientation
Implant rotation, e.g. internal or external
Implant flexion
Implant extension
Implant anteversion
Implant retroversion
Implant abduction
Implant adduction
Implant joint line, e.g. between a femoral component and a tibial component In various embodiments, a hybrid kinematic model could include data obtained by moving a joint through a range of motion, which can include pre-operative imaging of the joint as well as intraoperative imaging of the joint with a trial or actual implant or implant component in place, but not permanently affixed yet to the joint. Various such measurements could be obtained, including:

Preoperative
   Active
   Passive
   With optional stress testing
Intraoperative prior to performing surgical steps, i.e. on the unaltered joint
   Active, e.g. before anesthesia
   Passive
   Passive with optional stress testing
Intraoperative after performing surgical steps
   Passive
   Passive with optional stress testing
Intraoperative with trial implant in place
   Passive
   Passive with optional stress testing
Intraoperative with definitive implant in place, not affixed yet.
   Passive
   Passive with optional stress testing
Intraoperative with definitive implant in place, affixed to joint/bone
   Passive
   Passive with optional stress testing In various embodiments, the same or similar measurements could be obtained for a given joint from a contralateral joint, pre-operatively or intraoperatively. Alternatively, a database of the same of contralateral joints from a given patient and/or patient population may be queried and/or utilized.

Based on joint kinematics assessment and hybrid modeling, the position or orientation of a guide tool could optionally be adjusted as a technique for adjusting the position or orientation of the implant after placement in order to achieve a better or more desired kinematic result. The position or orientation of a guide within a guide tool could similarly and/or alternatively be optionally adjusted as a technique for adjusting the position or orientation of the implant after placement in order to achieve a better or more desired kinematic result. The position or orientation of both a guide tool and a guide within a guide tool could be optionally adjusted as a technique of adjusting the position or orientation of the implant after placement in order to achieve a better or more desired kinematic result. A wide variety of improved and/or desired kinematic results could be obtained, including:

improvements in ligament balancing, e.g. optimization of flexion and extension gap or balancing;

improvements in range of motion, e.g. flexion and extension;

improvements in joint stability, e.g. as a means of reducing the possibility of subluxation or dislocation;

improvements in performance for select daily activities, e.g. stair climbing or going downstairs;

avoidance or reduction of well know problems with joint replacement, e.g. mid-flexion instability.

In various embodiments described herein, thereof, one can measure joint motion prior to implantation (e.g. pre-operatively or intra-operatively) or after performing select surgical steps. Preoperative (e.g. via a virtual simulation of joint kinematics optionally including patient data including scan data) and intraoperative measurements can include measurements of one or more dimensions of the joint (e.g. in an AP, ML, SI or oblique planes), one or more curvatures of the joint (e.g. of cartilage or subchondral bone), one or more slopes of the joint (e.g. from a medial to a lateral condyle), measurements of distances (e.g. a condylar length or height or width of a notch), and measurements or estimations of ligaments, ligament locations, strength, insertion, origin, muscle location, strength, insertion, origin and the like. Any of these simulations and/or models, both pre-operatively and intraoperatively, can also include finite element modeling, for example for estimating the stress or forces exerted on an implant (e.g. in select implant locations or along a chamfer cut). The finite element data can be augmented with patient specific data (e.g., data obtained from the patient's scan including also for example bone mineral density or structure) or any of the parameters mentioned above and throughout the specification.

If kinematic optimizations are simulated pre-operatively, they can be used to adjust the position or orientation of a mold or guide or combinations thereof used during surgery. This can, optionally, result in a change of the physical shape of the guide or the mold. If kinematic measurements are performed during the surgical procedure, for example by measuring marker motion during a range of motion prior to placing an implant, the position or orientation of a patient specific mold or guide included therein or attached thereto can be adjusted intraoperatively. Such adjustments can be, for example, performed with use of shims, spacers, spacer blocks, ratchet-like mechanisms, dial-like mechanisms, electronic mechanisms, and other mechanisms known in the art or developed in the future. Alternatively, the guide tool can include more than one guide so that the position of a drill hole, a peg hole or a cut can be adjusted intraoperatively. Alternatively, the guide tool can allow for attachment of a block, e.g. for drilling or cutting, either in multiple different locations for kinematic optimization, or the position of the guide tool can be adjusted by inserting, for example, shims or spacers between the guide tool and the block.

Thus, while patient adapted guide tools will typically place an implant in a fixed position and orientation, for example relative to one or more anatomic or biomechanical axes or anatomic landmarks, the methods described herein allow for optimization of implant position for a desired, improved kinematic result.

A wide variety of possible adjustments for implant components are contemplated in the various embodiments discussed herein, including: adjustment of implant flexion (or extension) relative to one or more anatomic or biomechanical axes (e.g. femoral component flexion in a knee prosthesis); adjustment of implant rotation (e.g. internal or external) relative to one or more anatomic or biomechanical axes or landmarks (e.g. femoral component rotation for flexion and/or extension balancing), or tibial component rotation; adjustment of anterior or posterior implant position (e.g. femoral component position—for flexion balancing) or tibial component position relative to one or more anatomic or biomechanical axes or landmarks; adjustment of medial or lateral implant position (e.g. femoral component position or tibial component position relative to one or more anatomic or biomechanical axes or landmarks); and/or adjustment of superior or inferior implant position (e.g. femoral component position or tibial component position relative to one or more anatomic or biomechanical axes or landmarks—optionally performed via recuts).

The various adjustments contemplated herein can include repositioning and/or rotating an AP cut guide on a distal femur, in order to rotate the implant position. A flexion spacer or cut guide can be rotated or changed in position, for example with a spacer or shim, in order to change implant position or orientation, for example for flexion balancing. A tibial guide can be rotated, for example for controlling varus or valgus or for controlling tibial component rotation.

In various embodiments, an ultrasound scan can be obtained. The ultrasound scan can be obtained in 1D, 2D and 3D. The scan can include information about the curvature of the joint, e.g. a cartilage or subchondral bone, and its surface shape. This information can be used to generate a patient adapted guide tool with at least one portion including a patient specific surface derived from the scan.

In various embodiments, 4D imaging can be employed, as it can be a preferred mode for imaging of joint motion, with the three dimensions being space and the 4th dimension being time or motion. Joint motion that can be measured can include, but is not limited to: translation of one articular surface relative to the other; rotation of one articular surface relative to the other during: Flexion; Extension; Abduction; Adduction; Elevation; Internal rotation; External rotation; and other joint movements.

In various embodiments, the resultant kinematic scan data (3D or 4D) can be used to assess joint motion prior to surgery. Such ultrasound based kinematic data can be captured for the joint that will be operated or for the contralateral joint. A surgical procedure, e.g. a ligament repair (e.g. ACL), an osteotomy or an implant placement can then be simulated on the data. If an implant placement is performed, optionally virtual cuts, drilling or reaming can be introduced. The implant surfaces can be superimposed and the kinematics or biomotion after implant placement can be assessed and compared to the unoperated state.

Many simulations and optimizations can be performed in order to achieve postoperative kinematics that closely resemble the preoperative kinematics or in the case of severe arthritis that resemble the kinematics of the patient in the pre-arthritic state. These simulations or optimizations can include:

Selection of an implant size;
Selection of implant shape(s), e.g. on a femur or a tibia or a tibial insert shape (including, for example, sagittal curvature, coronal curvature of femoral component(s), tibial component, insert height etc.)
Selection of an implant position;
Selection of an implant orientation;
Selection of a resection height or level, e.g. on a femur or a tibia or a glenoid or an acetabulum or a femoral neck in order to maintain a joint line location after implantation similar to the unoperated state.

If a patient specific implant is employed as part of the various embodiments described herein, any of the parameters in Table 1 can be adapted or changed in order to optimize the kinematic result relative to the preoperative simulation (based on ultrasound, other scans or databases or combinations thereof).

Muscle Kinematics

Various embodiments described herein can include the modeling of muscle kinematics as part of a hybrid kinematics analysis and modeling technique to facilitate a joint arthroplasty procedure. A human body typically includes four muscle regions: head and neck; trunk, front and back; brachium, antebrachium and hand; thigh, leg and foot. Each muscle region includes certain muscle groups, and each muscle group includes certain muscles with their own origins and insertions, as well as distinct functions. As described below, various muscle groups and/or component muscles therein may be modeling and included in a hybrid kinematic model:

| Muscle Region | Muscle Group | Muscle | Origin | Insertion | Action |
|---|---|---|---|---|---|
| Head and Neck | Suboccipital | Obliquus capitis inferior | spinous process of axis (C2) | transverse process of atlas (C1) | rotates the head to the contracted side |
| | | Obliquus capitis superior | transverse process of atlas (C1) | between superior and inferior nuchal line of occiput | bilaterally extends the head; laterally flexes to the contracted side |
| | | Rectus capitis posterior major | spinous process of axis (C2) | inferior nuchal line (lateral to minor) | bilaterally extends the head; rotates the head to the contracted side |
| | | Rectus capitis posterior minor | posterior tubercle of atlas (C1) | inferior nuchal line (adjacent to midline) | bilaterally extends the head |
| | Prevertebral | Longus colli | lower anterior vertebral bodies and transverse processes | anterior vertebral bodies and transverse processes several segments above | flexes the head and neck |
| | | Longus capitis | upper anterior vertebral bodies and transverse processes | anterior vertebral bodies and transverse processes several segments above | flexes the head and neck |
| | | Rectus capitis anterior | anterior base of the transverse process of the atlas | occipital bone anterior to foramen magnum | flexes the head |
| | | Rectus capitis lateralis | transverse process of the atlas | jugular process of the occipital bone | bends the head laterally |
| | Anterolateral Neck | Anterior scalene | anterior tubercles of transverse processes of C3-C6 | 1st rib | if transverse process fixed: elevates the ribs for respiration; if ribs fixed: rotates to side opposite of contraction laterally flexes to the contracted side bilaterally flexes the neck |
| | | Scalenus minimus | anterior tubercles of transverse processes of C6 & 7 | 1st rib and/or supraplural membrane | if transverse process fixed: elevates the ribs for respiration; if ribs fixed: rotates to side opposite of |

-continued

| Muscle Region | Muscle Group | Muscle | Origin | Insertion | Action |
|---|---|---|---|---|---|
| | | | | | contraction laterally flexes to the contracted side bilaterally flexes the neck |
| | | Middle scalene | transverse processes of all cervical vertebrae | 1st rib (behind anterior scalene) | if transverse process fixed: elevates the ribs for respiration; if ribs fixed: rotates to side opposite of contraction laterally flexes to the contracted side bilaterally flexes the neck |
| | | Posterior scalene | posterior tubercles of transverse processes of C5 & C6 | 2nd and/or 3rd rib | if transverse process fixed: elevates the ribs for respiration if ribs fixed, rotates to side opposite of contraction laterally flexes to the contracted side bilaterally flexes the neck |
| | Superficial Neck | Sternocleidomastoid | (two heads) manubrium of sternum; medial portion of clavicle | mastoid process of temporal bone | rotates to side opposite of contraction laterally flexes to the contracted side bilaterally flexes the neck |
| | | Platysma | subcutaneous skin over delto-pectoral region | invests in the skin widely over the mandible | depress mandible and lower lip tenses the skin over the lower neck |
| Anterior Neck | | Sternohyoid | posterior aspect of manubrium sternal end of clavicle | body of hyoid | depresses hyoid & larynx acts eccentrically with the suprahyoid muscles to provide them a stable base |
| | | Omohyoid | superior belly: hyoid bone (lateral to sternohyoid) inferior belly: superior scapular border (medial to suprascapular notch) | both bellies meet at the clavicle & are held to the clavicle by a pulley tendon | depresses hyoid & larynx acts eccentrically with the suprahyoid muscles to provide them a stable base |
| | | Sternothyroid | posterior aspect of manubrium | oblique line of thyroid cartilage | depresses hyoid & larynx; acts eccentrically with the suprahyoid muscles to provide them a stable base |
| | | Thyrohyoid | oblique line of thyroid cartilage | body of hyoid | depresses hyoid; may assist in larynx elevation |

-continued

| Muscle Region | Muscle Group | Muscle | Origin | Insertion | Action |
|---|---|---|---|---|---|
| | | Stylohyoid | styloid process of temporal bone | lateral margin of hyoid (near greater horn) | pulls the hyoid superiorly & posteriorly during swallowing fixes the hyoid bone for infrahyoid action |
| | | Digastric | post belly: mastoid process of temporal bone; anterior belly: digastric fossa of internal mandible | both bellies meet and attach at the lateral aspect of body of hyoid by a pulley tendon | open mouth by depressing mandible; fixes hyoid bone for infrahyoid action |
| | | Mylohyoid | inner surface of mandible off the mylohyoid line | body of hyoid along midline at mylohyoid raphe | elevates the hyoid bone; raises floor of mouth (for swallowing); depresses mandible when hyoid is fixed |
| | | Geniohyoid | inner surface of the mandible off the mental spines | body of hyoid (paired muscles separated by a septum) | elevates the tongue; depress the mandible; works with mylohyoid |
| | Epicranial | Occipitalis (2 bellies) | lateral ⅔ of superior nuchal line; external occipital protuberance | galea aponeurosis, over the occipital bone | draws back the scalp to raise the eyebrows and wrinkle the brow |
| | | Frontalis (2 bells) | galea aponeurosis, anterior to the vertex | skin above the nose and eyes | draws back the scalp to raise the eyebrows and wrinkle the brow |
| | Muscles of Facial Expression | Orbicularis oculi | orbital portion: nasal process of frontal bone; palpebral portion: palpebral ligament; lacrimal portion: lacrimal crest of lacrimal bone | circumferentially around orbit; meeting in palpebral raphe | powerfully closes the eye |
| | | Corrugator supercilii | frontal bone just above the nose | skin of the medial portion of the eyebrows | draws the eyebrows downward and medially |
| | | Orbicularis oris | alveolar border of maxilla; lateral to midline of mandible | circumferentially around mouth; blends with other muscles | closes the lips; protrudes the lips |
| | | Levator labii superioris alaeque nasi | frontal process of maxilla | upper lip muscles; nasal cartilage | elevates the upper lip; flares the nostrils |
| | | Levator labii superioris | medial ½ of infraorbital margin | upper lip muscles | elevates the upper lip |
| | | Zygomaticus minor | zygomatic bone, posterior to maxillary-zygomatic suture | skin of the upper lip | elevates the upper lip |

| Muscle Region | Muscle Group | Muscle | Origin | Insertion | Action |
|---|---|---|---|---|---|
| | | Zygomaticus major | anterior to zygomatic-temporal suture | modiolus (angle of the mouth) | lifts and draws back the angle(s) of the mouth (as in smiling) |
| | | Risorius | parotid fascia | modiolus (angle of the mouth) | draws the mouth laterally (as in smiling) |
| | | Levator anguli oris | maxilla, inferior to infraorbital foramen | modiolus (angle of the mouth) | lifts the angle(s) of the mouth (as in smiling) |
| | | Buccinator | posterior alveolar process of maxilla; posterior alveolar process of mandible; along the pterygomandibular raphe | modiolus | compresses the cheek(s) |
| | | Depressor anguli oris | along the oblique line of mandible; lateral aspect of mental tubercle of the mandible | modiolus | lowers the angle(s) of the mouth (as in frowning) |
| | | Depressor labii inferioris | mandible, between symphysis and mental foramen; along oblique line of the mandible | skin of the lower lip | draws the lower lip downward and laterally |
| | Muscles of Mastication | This group includes: Masseter; Medial pterygoid; Lateral pterygoid; their actions relate to movement of jaw and mouth. | | | |
| | Extraocular | This musculature group includes: Levator palpebrae superioris; Lateral rectus; Medial rectus; Superior rectus; Inferior rectus; Superior oblique; Inferior oblique; their actions are related to eyelid and eye movements. | | | |
| | Laryngeal | This musculature group includes: sternothyroid; thyrohyoid; stylopharyngeus; palatopharyngeus; posterior cricoarytenoid; arytenoid, oblique; arytenoid, transverse; aryepiglottic; cricothyroid; lateral cricoarytenoid; thyroarytenoid; thyroepiglottic; vocalis; constrictor, inferior pharyngeal; cricopharyngeus. | | | |
| Trunk, front and back | Superficial Back | Trapezius | external occipital protuberance; along the medial sides of the superior nuchal line; ligamentum nuchae (surrounding the cervical spinous processes); spinous processes of C1-T12 | posterior, lateral 1/3 of clavicle; acromion; superior spine of scapula | elevates scapula; upward rotation of the scapula (upper fibers); downward rotation of the scapula (lower fibers); retracts scapula |
| | | Latissimus dorsi | spinous process of T7-L5; upper 2-3 sacral segments; iliac crest; lower 3 or 4 Ribs | lateral lip of the intertubercular groove | adduction of humerus; medial rotation of the humerus; extension from flexed position; downward rotation of the scapula |

-continued

| Muscle Region | Muscle Group | Muscle | Origin | Insertion | Action |
|---|---|---|---|---|---|
| | Pectoral | Subclavius | first rib about the junction of bone and cartilage | lower surface of clavicle | assists in stabilizing the clavicle |
| | | Pectoralis major | medial ⅓ of clavicle; anterior aspect of manubrium & length of body of sternum; cartilaginous attachments of upper 6 ribs; external oblique's aponeurosis | lateral lip of bicipital groove to the crest of the greater tubercle; clavicular fibers insert more distally; sternal fibers more proximally | adducts humerus; medially rotates humerus; flexion of the arm from extension (clavicular portion) |
| | | Pectoralis minor | outer surface of ribs 2-5 or 3-5 or 6 | medial aspect of coracoid process of the scapula | depresses & downwardly rotates the scapula; assists in scapular protraction from a retracted position; stabilizes the scapula |
| | Shoulder Girdle | Levator scapulae | transverse processes of C1-C3 or C4 | superior angle of scapula toward the scapular spine | elevates the scapula; extends and/or laterally flexes the head |
| | | Rhomboid minor | spinous process of C7 &T1; ligamentum nuchae; supraspinous ligament | medial margin of the scapula at the medial angle | retract scapula |
| | | Rhomboid major | spinous processes of T2-T5; supraspinous ligament | medial scapula from the scapular spine to the inferior angle | retract scapula |
| | | Serratus anterior | fleshy slips from the outer surface of upper 8 or 9 ribs | costal aspect of medial margin of the scapula | protract scapula; stabilize scapula; assists in upward rotation |
| | | Deltoid | lateral, anterior ⅓ of distal clavicle; lateral boarder of the acromion; scapular spine | deltoid tuberosity of humerus | abducts arm; flexion and medial rotation (anterior portion); extension and lateral rotation (posterior portion) |
| | | Supraspinatus | supraspinous fossa; muscle fascia | uppermost of three facets of the greater tubercle of humerus | abduction of arm (first 15-20°); stabilizes glenohumeral joint |
| | | Infraspinatus | infraspinous fossa; muscle fascia | middle facet of greater tubercle of humerus | external rotation of the humerus; stabilizes the glenohumeral joint |
| | | Teres minor | middle half of the scapula's lateral margin | lowest of three facets of the greater tubercle of humerus | lateral rotation of the humerus; stabilizes the glenohumeral joint |

-continued

| Muscle Region | Muscle Group | Muscle | Origin | Insertion | Action |
|---|---|---|---|---|---|
| | | Teres major | inferior, lateral margin of the scapula | crest of lesser tubercle Oust medial to the insertion of latissimus dorsi) | assists in adduction of arm assists in medial rotation of arm assists in extension from an flexed position |
| | | Subscapularis | subscapular fossa | lesser tubercle of humerus | medial rotation of the humerus; stabilizes the glenohumeral joint |
| | Splenius | Splenius capitis | lower portion of ligamentum nuchae; spinous processes of C3-T3(4) | superior nuchal line; mastoid process of temporal bone | bilateral contraction: extend head & neck; unilateral contraction: rotate and laterally bend head & neck to the contracted (same) side |
| | | Splenius cervicis | spinous process of T3-T6 | posterior tubercles of transverse processes of C2-C4 | |
| | Erector Spinae | lliocostalis lumborum | common tendinous origin: (same for all lower erector spinae) sacrum; iliac crest; spinous processes of lower thoracic & most lumbar vertebrae | lower border of angles of ribs (5)6-12 | bilateral: extension of vertebral column; maintenance of erect posture (pneumonic = I Like Standing); stabilization of vertebral column during flexion, acting in contrast to abdominal muscles and the action of gravity; unilateral: lateral bend to same side; rotation to same side; opposite muscles contract eccentrically for stabilization |
| | | lliocostalis thoracis | upper border of ribs 6-12 (medial to I. lumborum's insertion.) | lower border of angles of ribs 1-6 (sometimes transverse process of C7) | |
| | | lliocostalis cervicis | angles of ribs 1-6 | transverse processes of C4-C6 | |
| | | Longissimus thoracis | common tendinous origin: (see above) | transverse processes of all thoracic vertebrae; all ribs between tubercles and angles; transverse processes of upper lumbar vertebrae | |
| | | Longissimus cervicis | transverse processes of T1-T5(6) | transverse processes of C2-C6 | |
| | | Longissimus capitis | transverse and articular processes of middle and lower cervical vertebrae; transverse processes of upper thoracic vertebrae | posterior aspect of mastoid process of temporal bone | |
| | | Spinalis thoracis | common tendinous origin: (see above) | spinous processes T3(4)-T8(9) | |

| Muscle Region | Muscle Group | Muscle | Origin | Insertion | Action |
|---|---|---|---|---|---|
| | | Spinalis cervicis | spinous processes of C6-T2 | Spinous processes of C2 (and possibly extend to C3 or C4) | |
| | | Spinalis capitis | spinous processes of lower cervical & upper thoracic vertebrae | between superior & inferior nuchal lines of occipital bone | |
| | Transverso-spinal | Semispinalis thoracis | transverse processes of T6-T12 vertebrae | spinous processes of upper thoracic & lower cervical vertebrae | bilaterally extends vertebral column, especially head and neck; controls lateral flexion to side opposite contraction (eccentric for stability); maintains head posture |
| | | Semispinalis cervicis | transverse processes of T1-T6 vertebrae and can go down to lower thoracic | spinous processes of C2-T5(6) | bilaterally extends vertebral column, especially head and neck; controls lateral flexion to side opposite contraction (eccentric for stability); maintains head posture |
| | | Semispinalis capitus | transverse processes of T1-T6; articular processes of C4-C7 | between superior & inferior nuchal lines of occipital bone | bilaterally extends vertebral column, especially head and neck; controls lateral flexion to side opposite contraction (eccentric for stability); maintains head posture |
| | | Multifidus | cervical region: from articular processes of lower cervical vertebrae; thoracic region: from transverse processes of all thoracic vertebrae; lumbar region: lower portion of dorsal sacrum; PSIS; deep surface of tendenous origin of erector spinae; mamillary processes of | spinous process of all vertebrae extending from L5-C2 (skipping 1-3 segments) | bilaterally extends vertebral column; controls lateral flexion to side opposite contraction (eccentric for stability); unilaterally rotate vertebral bodies (column) to opposite side |

-continued

| Muscle Region | Muscle Group | Muscle | Origin | Insertion | Action |
|---|---|---|---|---|---|
| | | Long rotators | all lumbar vertebrae transverse process of one vertebra | skips one vertebra to insert on the base of spinous process of vertebra above | rotate to opposite side; bilateral extension |
| | | Short rotators | transverse process of one vertebra | base of spinous process of vertebra immediately above | rotate to opposite side; bilateral extension |
| | Segmental | Interspinalis | spinous processes of each vertebra | to the spinous process of vert. immediately above | extension of the vertebrae segments |
| | | Intertransversi | cervical region: from the anterior tubercle of transverse process; from the posterior tubercle of transverse process; thoracic region: (poorly developed); lumbar region: lateral aspect of the transverse process; mamillary process | cervical region: to the anterior tubercle immediately above; to the posterior tubercle immediately above; thoracic region: (poorly developed); lumber region: lateral aspect of the transverse process immediately above; to the accessory process on the vertebra immediately above | laterally flexes each respective pair of vertebrae; (also eccentric muscle contraction provides stability) |

Various additional muscle groups can be modeled as of a hybrid kinematics analysis and modeling technique to facilitate joint arthroplasty procedures. Such muscle groups can include the following and information regarding the, including:

Brachium to Hand Musculature—this region includes four muscle groups: Brachium; Antebrachial Flexors; Antebrachial Extensors; Hand & Wrist.

The Brachium Musculature includes:
Coracobrachialis:
Origin: coracoid process of the scapula;
Insertion: medial shaft of the humerus at about its middle
Action: flexes the humerus; assists to adduct the humerus
Biceps brachii:
Origin: long head—supraglenoid tubercle and glenohumeral labrum; short head—tip of the coracoid process of the scapula
Insertion: radial tuberosity; bicipital aponeurosis
Action: flexes the forearm at the elbow (when supinated); supinates forearm from neutral; stabilizes anterior aspect of shoulder; flexes shoulder (weak if at all)
Brachialis:
Origin: lower ½ of anterior humerus; both intermuscular septa
Insertion: ulnar tuberosity; coronoid process of ulna slightly
Action: elbow flexion (major mover)
Triceps brachii:
Origin: long head—infraglenoid tubercle of the scapula; lateral head—upper half of the posterior surface of the shaft of the humerus, and the upper part of the lateral intermuscular septum; medial head—posterior shaft of humerus, distal to radial groove and both the medial and lateral intermuscular septum (deep to the long & lateral heads)
Insertion: posterior surface of the olecranon process of the ulna; deep fascia of the antebrachium
Action: long—adducts the arm, extends at the shoulder, and a little elbow flexion;
lateral—extends the forearm at the elbow; medial—extends the forearm at the elbow
Anconeus:
Origin: posterior surface of the lateral epicondyle of the humerus
Insertion: lateral aspect of olecranon extending to the lateral part of ulnar body
Action: extends the forearm at the elbow; supports the elbow when in full extension
The Antebrachial Flexor Musculature includes:
Pronator teres:
Origin: humeral head: upper portion of medial epicondyle via the CFT (common flexor tendon), medial brachial intermuscular septum; ulnar head—coronoid process of ulna, antebrachial fascia
Insertion: lateral aspect of radius at the middle of the shaft (pronator tuberosity)
Action: pronates forearm (during rapid or forced pronation); weakly flexes the elbow Flexor carpi radialis:
Origin: medial epicondyle via the CFT (common flexor tendon); antebrachial fascia;
Insertion: base of the 2nd and sometimes 3rd metacarpals
Action: flexes the hand at the wrist; radially deviates the wrist; may assist to pronate the forearm Palmaris longus:
Origin: medial epicondyle via the CFT (common flexor tendon); antebrachial fascia
Insertion: central portion of the flexor retinaculum; superficial portion of the palmar aponeurosis;
Action: flexes the hand at the wrist Flexor carpi ulnaris:
Origin: humeral head—medial epicondyle via the CFT (common flexor tendon); ulnar head: medial aspect of olecranon; proximal ⅗ of dorsal ulnar shaft; antebrachial fascia
Insertion: pisiform & hamate bones (via the pisohamate ligament); base of the 5th metacarpal (via the pisometacarpal ligament)
Action: flexes the hand at the wrist; ulnarly deviates the wrist; stabilizes wrist to permit powerful thumb motion Flexor digitorum superficialis:
Origin: humeral-ulnar head: medial epicondyle via the CFT (common flexor tendon), medial boarder of base of coronoid process of ulna, medial (ulnar) collateral ligament, antebrachial fascia; radial head: oblique line of radius along its upper anterior boarder
Insertion: both sides of the base of each middle phalanx of the 4 fingers
Action: flexes the proximal and middle phalanges; flexes the wrist if fingers are extended Flexor digitorum profundus:
Origin: anterior & medial surface of upper ¾ ulna; adjacent interosseous membrane;
Insertion: distal phalanx of medial 4 digits (through FDS tunnel)
Action: flexes the distal IP joints and in so doing flexes the proximal and middle IP joints; flexes the wrist if fingers are extended Flexor pollicis longus:
Origin: middle anterior surface of the radius; interosseous membrane (may also originate from lateral boarder of coronoid process or medial epicondyle) Insertion: palmar aspect of base of the distal phalanx of thumb (deep to flexor retinaculum)
Action: flexes the distal phalanx of the thumb (IP joint); flexes the other joints to the wrist (McP, CMc and weakly at the wrist)

Pronator quadratus:
Origin: distal ¼ anteriomedial surface of ulna
Insertion: distal ¼ anteriolateral surface of radius
Action: pronates the forearm and hand The Antebrachial Extensor Musculature includes:
Brachioradialis:
Origin: upper lateral supracondylar ridge of humerus (between the triceps and brachialis muscles); lateral intermuscular septum of humerus
Insertion: superior aspect of styloid process of radius; lateral side of the distal ½ to ⅓ of the radius; antebrachial fascia
Action: flexes the forearm at the elbow; pronates the forearm when supinated; supinates the forearm when pronated Extensor carpi radialis longus:
Origin: lower lateral supracondylar ridge (below the brachioradialis); lateral intermuscular septum of humerus
Insertion: base of 2nd metacarpal
Action: extends the hand at the wrist; radially deviates the hand at the wrist; weakly flexes the forearm at the elbow; weakly supinates the forearm Extensor carpi radialis *brevis*:
Origin: lateral epicondyle via the CET (common extensor tendon); radial collateral ligament; antebrachial fascia
Insertion: base of 3rd metacarpal
Action: extends the hand at the wrist; radially deviates the hand at the wrist Extensor digitorum:
Origin: lateral epicondyle via the CET (common extensor tendon); antebrachial fascia
Insertion: base of middle phalanx of each of the four fingers (central band); base of distal phalanx of each of the four fingers (2 lateral bands)
Action: extends the four medial digits; extends the wrist if fingers flexed; abducts the digits (spreads the digits as it extends them)

Extensor digiti minimi:
Origin: lateral epicondyl via the CET (common extensor tendon); antebrachial fascia; ulnar aspect of extensor digitorum
Insertion: base of middle phalanx of the 5th digit (central band); base of distal phalanx of the 5th digit (2 lateral bands)
Action: extends the 5th digit; abducts the 5th digit Extensor carpi ulnaris:
Origin: 1st head—lateral epicondyle via the CET (common extensor tendon); 2nd head—posterior body of ulna; antebrachial fascia
Insertion: medial side of base of the 5th metacarpal
Action: extends the hand at the wrist; ulnarly deviates the hand at the wrist Supinator:
Origin: lateral epicondyle of humerus; supinator crest of ulna; radial collateral ligament; annular ligament; antebrachial fascia
Insertion: proximal portion of anteriorlateral surface of the radius
Action: supinates the forearm Abductor pollicis longus:
Origin: posterior surfaces of ulna and radius; interosseous membrane; antebrachial fascia
Insertion: lateral aspect of base of 1st metacarpal
Action: abducts the 1st metacarpal; assists to extend & rotate the thumb; radially deviates the hand at the wrist; flexes the hand at the wrist Extensor pollicis *brevis*:
Origin: posterior surfaces of radius (below abductor pollicis longus); interosseous membrane; antebrachial fascia
Insertion: base of proximal phalanx of thumb (often a slip inserts into extensor pollicis longus tendon)
Action: extends the proximal phalanx and 1st metacarpal of the thumb; radially deviates the hand at the wrist Extensor pollicis longus:
Origin: posterior surface of ulna; interosseous membrane; antebrachial fascia
Insertion: distal phalanx of thumb
Action: extends distal phalanx of thumb; extends proximal phalanx of thumb; assists to extend the hand at the wrist (if fingers flexed)

Extensor indicis:
Origin: posterior surface of ulna (distal to extensor pollicis longus); interosseous membrane; antebrachial fascia Insertion: base of middle and distal phalanx of the index finger Action: extends the 2nd digit (McP & IP joints); adducts the 2nd digit; assists to extend the hand at the wrist; stabilizes McP joint for flexion of IP solely The Hand and Wrist Musculature includes:

Abductor pollicis brevis:

Origin: distal border of flexor retinaculum; trapezium (may be variable)

Insertion: lateral aspect of base of proximal phalanx of the thumb; may also send a slip to the tendon of extensor pollicis longus Action: abducts thumb (at the McP joint); participates to flex the thumb (at the McP joint); if attached to extensor pollicis longus, it might assist to extend the thumb Flexor pollicis brevis:

Origin: superficial head: distal border of flexor retinaculum, trapezium; deep head: floor of carpal tunnel, indirectly to scaphoid & trapezium Insertion: base of proximal phalanx of thumb; can also attach to the lateral sesamoid bone at the McP joint Action: powerfully flexes the thumb (at the McP joint)

Opponens pollicis:

Origin: distal border of flexor retinaculum; trapezium

Insertion: lateral aspect of the 1st metacarpal

Action: opposes the thumb to the fingers

Adductor pollicis:

Origin: transverse head: 3rd metacarpal; oblique head: base of 1st, 2nd and 3rd metacarpals; floor of carpal tunnel Insertion: medial aspect of the base of proximal phalanx; medial sesamoid at McP Action: adducts the thumb; may assist to flex the thumb (at the McP joint)

Palmaris brevis:

Origin: medial margin of palmar aponeurosis

Insertion: skin of ulnar border of palm; may insert on the pisiform

Action: tenses the skin on the ulnar side, which is used in a grip action

Abductor digiti minimi:

Origin: pisiform & tendon of flexor carpi ulnaris

Insertion: medial aspect of the base of proximal phalanx of the 5th digit; may send a slip to the ulnar side of the dorsal expansion Action: abduct 5th digit (requires pisiform stabilized by FCU); assists to flex the 5th digit (at McP); may assist in extension of 5th digit (at IP due to slips to extensor digitorum)

Flexor digiti minimi brevis:

Origin: distal border of flexor retinaculum; hook of the hamate

Insertion: medial aspect of the base of proximal phalanx

Action: flexes the 5th digit (at the McP joint)

Opponens digiti minimi

Origin: distal border of flexor retinaculum; hook of the hamate

Insertion: medial aspect of the 5th metacarpal

Action: opposes the 5th digit with the thumb; assists to "cup" the palm

Palmar interossei:

Origin: from the side of the metacarpal that faces the midline—to adduct them

Insertion: on the base of the proximal phalanx of the digit of origin (same side toward the midline); extensor hood of the same digit(s)

Action: adducts the fingers; flexes the fingers (at the McP while IP joints are extended)

Dorsal interossei:

Origin: between each metacarpal

Insertion: directly distal to the origin on the base of the proximal phalanx closest to the midline (to abduct them); extensor hood of the same digit(s)

Action: abducts the fingers (hint: DAB); flexes the fingers (at the McP while IP joints are extended)

Lumbricals:

Origin: tendon of flexor digitorum profundus; 1 & 2 have a single head of origin (from radial aspect of tendon); 3 & 4 have two heads of origin (each head from an adjacent tendon)

Insertion: extensor hood of digits 2-5

Action: flexes the fingers (at the McP joints); extend IPs

Thigh to Foot Musculature

Muscle Groups within this Region includes: Gluteal; Posterior Thigh; Adductor Thigh; Anterior Thigh; Posterior Leg; Anterolateral Leg; Foot The Gluteal Musculature includes:

Tensor fascia lata:

Origin: anterior aspect of iliac crest; anterior superior iliac spine (ASIS)

Insertion: anterior aspect of IT band, below greater trochanter

Action: hip flexion; medially rotate & abduct a flexed thigh; tenses IT tract to support femur on the tibia during standing Gluteus maximus:

Origin: outer rim of ilium (medial aspect); dorsal surface of sacrum and coccyx; sacrotuberous ligament Insertion: IT band (primary insertion); gluteal tuberosity of femur Action: powerful extensor of hip; laterally rotates thigh; upper fibers aid in abduction of thigh; fibers of IT band stabilize a fully extended knee Gluteus medius:

Origin: outer aspect of ilium (between iliac crest and anterior and posterior gluteal lines); upper fascia (AKA gluteal aponeurosis)

Insertion: superior aspect of greater trochanter

Action: anterior and lateral fibers abduct and medially rotate the thigh; posterior fibers may laterally rotate thigh; stabilizes the pelvis and prevents free limb from sagging during gait Gluteus minimus:

Origin: outer aspect of ilium (between anterior and inferior gluteal lines)

Insertion: greater trochanter (anterior to medius); articular capsule of hip joint Action: abduct and medially rotate the thigh; stabilizes the pelvis and prevents free limb from sagging during gait Piriformis:

Origin: pelvic surface of sacrum (anterior portion)

Insertion: medial surface of greater trochanter (through greater sciatic foramen)

Action: lateral rotation of extended thigh; abducts a flexed thigh

Superior gemellus:

Origin: ischial spine

Insertion: medial aspect of greater trochanter via upper tendon of obturator internus Action: laterally rotates femur; abducts thigh when flexed Obturator internus:

Origin: internal aspect margins of obturator foramen; obturator membrane

Insertion: medial aspect of greater trochanter (through lesser sciatic foramen)
Action: laterally rotates femur; abducts thigh when flexed
Inferior gemellus:
Origin: ischial tuberosity
Insertion: medial aspect of greater trochanter via lower tendon of obturator internus
Action: laterally rotates femur
Quadratus femoris:
Origin: lateral aspect of ischial tuberosity
Insertion: quadrate line (along posterior aspect of femur and intertrochanteric crest)
Action: laterally rotates femur
Posterior Thigh Musculature includes:
Semitendinosus:
Origin: ischial tuberosity
Insertion: medial aspect of tibial shaft; contributes to the pez anserine
Action: extends hip; flexes knee; medially rotates tibia
Semimembranosus:
Origin: ischial tuberosity
Insertion: posterior medial aspect of medial tibial condyle; fibers join to form most of oblique popliteal ligament (& medial meniscus)
Action: flexes knee; extends hip; medially rotates tibia; pulls medial meniscus posterior during flexion
Biceps femoris:
Origin: long head: ischial tuberosity; short head: lateral lip of linea aspera and the lateral intermuscular septum
Insertion: head of fibula; maybe to the lateral tibial condyle
Action: flexor at the knee (mainly short head); laterally rotates thigh if flexed at the knee; extends hip (long head)
Adductor magnus: posterior fibers are sometimes considered part of this group. Its information is listed below with the other thigh adductors.
Adductor Thigh Musculature includes:
Adductor longus:
Origin: anterior surface of pubis, just inferior to the pubic tubercle
Insertion: medial lip of linea aspera on middle half of femur
Action: adducts thigh; flexes thigh; may laterally rotate thigh at the hip
Adductor brevis:
Origin: body & inferior ramus of pubis
Insertion: superior portion of linea aspera
Action: adducts thigh (major); aids in flexion of thigh; may laterally rotate thigh at the hip
Adductor magnus:
Origin: anterior fibers: inferior pubic ramus; oblique fibers: ischial ramus; posterior fibers: ischial tuberosity
Insertion: proximal ⅓ of linea aspera; adductor tubercle
Action: adducts the thigh; posterior fibers also extend and laterally rotate thigh
Gracilis:
Origin: body of pubis & inferior pubic ramus
Insertion: medial surface of proximal tibia, inferior to tibial condyle; contributes to the pez anserine
Action: adducts thigh; flexes knee; medially rotates tibia
Obturator externus:
Origin: medial surface of obturator foramen; external surface of obturator membrane
Insertion: trochanteric fossa of femur
Action: laterally rotates thigh; assists in flexion of hip joint Anterior Thigh Musculature includes:
Sartorius:
Origin: anterior superior iliac spine (ASIS)
Insertion: upper medial surface of body of tibia; contributes to pez anserine
Action: flexes hip and knee; laterally rotates thigh if flexed at the hip
Rectus femoris:
Origin: anterior head: anterior inferior iliac spine (AI'S); posterior head: ilium just above the acetabulum
Insertion: common quadriceps tendon into patella; tibial tuberosity via patellar ligament
Action: extends knee; flexes hip
Vastus lateralis:
Origin: greater trochanter; lateral lip of linea aspera; lateral intermuscular septum
Insertion: common quadriceps tendon into patella; tibial tuberosity via patellar ligament
Action: extends knee; can abnormally displace patella
Vastus intermedius:
Origin: anterior lateral aspect of the femoral shaft
Insertion: common quadriceps tendon into patella; tibial tuberosity via patellar ligament
Action: extends knee
Vastus medialis:
Origin: intertrochanteric line of femur; medial aspect of linea aspera
Insertion: common quadriceps tendon into patella; tibial tuberosity via patellar ligament
Action: extends knee
Articularis genus:
Origin: distal portion of anterior femoral surface, close to the knee; off the deep fibers of the vastus intermedius
Insertion: synovial membrane of the knee joint
Action: pulls the synovial membrane of the knee superior with knee extension; prevents impingement of the synovial membrane between patella and the femur
Psoas major:
Origin: transverse processes of L1-L5; vertebral bodies of T12-L4 and the intervening intervertebral discs
Insertion: iliopsoas tendon to the lesser trochanter of the femur
Action: hip flexion; lateral rotation
Illiacus:
Origin: inner surface of upper iliac fossa
Insertion: iliopsoas tendon to the lesser trochanter of the femur
Action: powerful hip flexion; lateral rotation
Pectineus:
Origin: pectineal line of the pubis; superior pubic ramus
Insertion: the pectineal line of the femur (just below the lesser trochanter on the posterior aspect of the femur)
Action: flexes hip; adducts thigh; medially rotates thigh
Posterior Leg Musculature includes:
Gastrocnemius:
Origin: medial head: just above medial condyle of femur; lateral head: just above lateral condyle of femur
Insertion: calcaneus via lateral portion of calcaneal tendon
Action: plantarflex the ankle; knee flexion (when not weight bearing); stabilizes ankle & knee when standing
Soleus:
Origin: upper fibula; soleal line of tibia
Insertion: calcaneus via medial portion of calcaneal tendon
Action: plantarflex the foot Plantaris:
Origin: above the lateral head of gastrocnemius on femur
Insertion: calcaneus, medial to calcaneal tendon, or blending with the calcaneal tendon
Action: like a weak gastrocnemius
Popliteus:
Origin: lateral femoral condyle; arcuate popliteal ligament; lateral meniscus; knee joint capsule
Insertion: posterior tibial surface above the soleal line
Action: insertion fixed: laterally rotates femur on tibia & unlocks knee; origin fixed: medially rotates tibia on femur & unlocks knee
Flexor digitorum longus:
Origin: posterior surface of tibia; crural fascia
Insertion: plantar surface of bases of the 2-5th distal phalanges
Action: primarily flexes 2nd-5th toes; weak plantarflexor; weak inversion & adduction of foot
Tibialis posterior:
Origin: posterior, proximal tibia; interosseous membrane; medial surface of fibula
Insertion: navicular tuberosity (principle); all 3 cuneiforms (plantar surface); bases of 2nd-4th metatarsals; cuboid; sustentaculum tali of calcaneus
Action: stabilizes ankle; inversion & adduction of foot; prevents hyperpronation while in gait; weak plantarflexion of ankle
Flexor hallucis longus:
Origin: posterior, inferior ⅔ of fibula; interosseous membrane; crural fascia & posterior intermuscular septum
Insertion: plantar surface of distal phalanx of hallux
Action: flexes big toe (hallux); weak plantarflexion of the foot; weak inversion & adduction of foot
Anterolateral Leg Musculature includes:
Peroneus longus:
Origin: head of the fibula; proximal ⅔ of lateral fibula; adjacent intermuscular septum
Insertion: plantar surface of cuboid; base of 1st & (2nd) metatarsal; plantar surface of medial cuneiform
Action: eversion & abduction of the foot; weak plantarflexion of the foot at the transverse tarsal joint
Peroneus brevis:
Origin: distal ⅔ of lateral fibula; posterior and anterior intermuscular septum
Insertion: tuberosity on lateral aspect of base of 5th metatarsal
Action: eversion & abduction of the foot; weak plantarflexion of foot
Tibialis anterior:
Origin: lateral tibial condyle; proximal ⅔ of anterolateral surface of tibia; interosseous membrane; anterior intermuscular septum & crural fascia
Insertion: medial & plantar surface of base of 1st metatarsal; medial & plantar surface of the cuneiform
Action: strongest dorsiflexor; inverts & adducts the foot
Extensor hallucis longus:
Origin: medial aspect of the fibula; interosseous membrane; crural fascia
Insertion: dorsal surface of base of proximal and distal phalanx of hallux
Action: extends distal phalanx of big toe; weak dorsiflexor; weak inversion & adduction
Extensor digitorum longus:
Origin: lateral condyle of the tibia; upper anterior surface of fibula; interosseous membrane; crural fascia
Insertion: dorsal surface of the bases of the middle & distal phalanxes of the 2nd-5th rays (via 4 tendons and giving a fibrous expansion)
Action: extends the lateral 4 toes; weak dorsiflexor & everts foot
Peroneus tertius:
Origin: distal ⅓ of anterior fibula; distal & lateral aspect of extensor digitorum
Insertion: dorsal surface of base of 5th metatarsal
Action: extends the 5th toe; weak dorsiflexor & everts foot
Foot Musculature includes:
Abductor hallucis:
Origin: medial process of calcaneal tuberosity; flexor retinaculum; plantar aponeurosis; medial intermuscular septum
Insertion: medial aspect of base of proximal phalanx of hallux
Action: flexes the big toe (primary action); may assist in abduction of big toe
Flexor digitorum brevis:
Origin: medial process of calcaneal tuberosity; plantar aponeurosis
Insertion: both sides of the bases of the middle phalanx of rays 2-5 (each of the 4 tendons splits forming tunnel for FDL)
Action: flexes toes 2-5
Abductor digiti minimi:
Origin: lateral & medial processes of the calcaneal tuberosity; plantar aponeurosis; lateral intermuscular septum
Insertion: lateral aspect of base of proximal phalanx of 5th ray
Action: abducts 5th toe; aids in flexing
Abductor ossis metatarsi quinti:
Origin: from fibers of abductor digiti minimi
Insertion: into the 5th metatarsal
Action: abducts the 5th ray
Quadratus plantae:
Origin: medial head: medial calcaneus; lateral head: lateral calcaneus & long plantar ligament
Insertion: lateral margin of tendon of flexor digitorum longus (FDL); may send slips into the distal tendons
Action: assists FDL in flexing the distal phalanxes of 2nd-5th toes; corrects FDL from pulling toes medially
Lumbricals:
Origin: from tendons of FDL: 1st: medial aspect of tendon to 2nd ray; 2nd-4th: two heads between the tendons in which they lie
Insertion: extensor tendons of EDL on dorsal foot
Action: flex proximal phalanges at MTP; extend middle & distal phalanges at IP
Flexor hallucis brevis:
Origin: medial aspect of the cuboid; lateral cuneiform
Insertion: medial aspect of base of proximal phalanx of hallux; lateral aspect of base of proximal phalanx of hallux
Action: flexes hallux at MTP
Adductor hallucis:
Origin: oblique head: base of 2nd-4th metatarsals & long plantar ligament; transverse head: deep transverse metatarsal ligament & plantar ligaments at MTP joints
Insertion: lateral aspect of base of proximal phalanx of hallux
Action: adduction of hallux at MTP; flexes hallux at MTP
Flexor digiti minimi brevis:
Origin: base of 5th metatarsal; digital sheath of peroneus longus Insertion: lateral aspect of base of proximal phalanx of 5th ray
Action: flexes the 5th toe at MTP
Plantar interossei (3 muscles):
Origin: medial aspect of 3rd-5th metatarsals (each muscle has a single head)
Insertion: medial aspect of base of proximal phalanx of the same ray (of 3rd-5th rays)
Action: adduct toes 3-5; flex toes 3-5 at MTP
Dorsal interossei (4 muscles):
Origin: from both metatarsals between which they lie
Insertion: base of proximal phalanx closest to the axis of the foot (2nd ray)
Action: abduct toes 2-4; flexes toes 2-4 at MTP
Extensor hallucis brevis:
Origin: upper anterolateral calcaneus; inferior extensor retinaculum
Insertion: base of proximal phalanx of hallux
Action: extends hallux
Extensor digitorum brevis:
Origin: upper anterolateral calcaneus; inferior extensor retinaculum
Insertion: middle & distal phalanges of 2nd-4th rays (via EDL)
Action: extends 2nd-4th rays Examples of Muscle Measurements and Modeling A wide variety of techniques can be employed to incorporate muscle and other soft tissue (i.e., tendons, ligaments, other connective tissues, fascia, fat, skin, etc.) information in a kinematic model of a joint and/or extremity. In some embodiments, a hybrid kinematic model of a joint can include information relating to adjacent joint structures (i.e., a knee model can include ankle and/or hip modeling data) as well as relevant soft tissue structures such as muscles and the like. In one exemplary embodiment, an upper extremity model can include modeling data relevant to the various extremity joints (i.e., shoulder, elbow, forearm, wrist, thumb and index finger/other digits) as well as the various muscle compartments (i.e., 50 or more individual muscle compartments) crossing each of these joints. The kinematics of each joint and the force-generating parameters for each muscle can be derived from any combinations of actual patient-specific data, experimental data, databases of relevant patients and/or mathematical approximations. The various models can estimate muscle-tendon lengths and movement arms for each of the muscles over a wide range of postures, movements and/or degrees of freedom. Given a modeled pattern of muscle activations, the hybrid kinematic model can estimate muscle forces, joint movements and surface/subsurface forces and stresses experienced by joint support structures and/or articulating surfaces (including implant component designs therefor).

Depending upon a wide variety of modeling constraints, a more physiologically-accurate hybrid kinematic model can be created and utilized. For example, "coupling" between various joints (i.e., passive finger flexion and wrist extension) can be included in a hybrid kinematic model, if desired. Moreover, various models can accommodate and/or account for differentiation in the "pose" and "tone" (i.e., the stiffness and/or tension of an individual muscle or group of muscles in a given portion of the musculoskeletal system) of various muscles in an extremity and/or joint model. Various models could incorporate data regarding the ability of human and other animals to coactivate agonist and antagonist muscles to increase stiffness while maintaining pose, which can mitigate instability under external loads and/or increase the accuracy of limbs in motor tasks. In various embodiments, the various levels of stress and/or strain in a muscle and/or muscle group modeled may indicate relevant information for the model, such as a value that exceeds a specified threshold and indicates the potential for injury and/or pain generation in a given muscle based upon a certain implant design and/or procedure, which may be important information to a clinician seeking to avoid such an occurrence in a patient during and after surgical recovery.

Where a complete hybrid model of a given joint might be prohibitively complex, or utilize excessive computing capacity, a modified hybrid model can be evaluated that employs kinematic data from major or unique muscle groups and/or other soft tissues, while minor or peripheral groups can be estimated, combined and/or ignored. Similarly, a model may include data from various combinations of muscle types based on subcutaneous depth and/or attachment, including skeletal muscles, "deep" muscles, "intermediate" muscles and "superficial" muscles. Depending upon the number and complexity of muscles modeled, as well as the number of bones spanned by each muscle, various muscles and/or muscle groups (as well as bony attachment points) may be disregarded in order to simplify the relevant model, if necessary.

In various alternative embodiments, hybrid kinematic models could include hybrid modeling of joint structures that account for damage and/or disruption to soft and/or connective tissues as a result of the surgical intervention (i.e., damage along a given surgical path, tissue releases, muscle separation and/or joint capsule removal) and/or that could account for previous, present and/or future damage and/or the formation of scar tissues. In various embodiments, the modeling data may reveal a preferred access path that minimizes and/or accounts for such damage/disruption during the surgical procedure, which may also mandate some change and/or alteration to the implant design and/or surgical procedure to accommodate the altered kinematics.

A wide variety of techniques for modeling anatomical systems can be incorporated into a hybrid kinematic model that can be useful, to varying degrees, in facilitating the design and/or selection of a patient-specific implant, tools and surgical procedure. For example, US Application Publication No. 20110137138 teaches that motion exercise is adapted to provide a degree of muscle tone or muscle relaxation of said patient based on said measurement data, and wherein accelerometers are adapted to provide said measurement data for determination of said degree of muscle tone or muscle relaxation. US Application Publication No. 20070137307 discloses an electromechanical force sensor uses a rotating element that aligns with the force and may carry a force magnitude sensor simplifying and providing more accurate measurement of force-angle and force-magnitude. The ability to detect simply force-angle and force-magnitude enables a variety of training and exercise devices, as well as modeling thereof.

US Application Publication No. 20060286522 discloses systems and methods for animating a character with activation-driven muscle deformation. External loads can be estimated through an iterative joint torque estimation process, and the external loads reflected in a physical model. Kinematic motion and the physical model reflecting external loads can be used to estimate joint torques. Muscle activations can be determined from the joint torques, and a character can be animated with muscle deformation responsive to the muscle activations. Employing these techniques, various types of kinematic motion models and physical models can be created to estimate joint torques that include external loads. Muscle activations can be determined from the estimated joint torques, and a character model can be animated with muscle deformation responsive to the muscle activations. External loads and muscle activations can be estimated through a two-step joint torque determination process. A first set of estimated joint torques can be estimated from the kinematic motion and the physical model. The first set of estimated joint torques can include an artificial external load (also called an "artificial load"). An artificial external load can be an apparent load that is caused by a force and/or torque acting on an object, but without a naturally occurring source in the environment. A non-zero artificial load will typically indicate the presence of unaccounted for external loads. This artificial external load from the first set of estimated joint torques can be redistributed to various points on the body to estimate physically-realizable external loads, which can be explained as physical interactions with the environment (i.e., contact forces with the ground). The external load can be applied to the physical model to produce a loaded physical model, and a second set of estimated joint torques can be estimated from the kinematic motion and the loaded physical model. The second set of estimated joint torques can include the effects of the external loads on the physical system, making them more physically realistic. Muscle activations can be determined from the second set of estimated joint torques, and a character model can be animated with muscle deformation responsive to the muscle activations. By including the effect of external loads and accelerations in the muscle activations, convincing character models with lifelike muscle deformations can be animated. Various of such models for alternative joint implant designs and/or placements can then be queried and/or compared to determine desired and/or undesired implant component features and/or kinematic effects.

In various alternative embodiments, a modeling system such as LifeMOD™ (commercially available from LifeModeler, Inc. of San Clement, Calif.) can be employed that models ligaments and muscles as force-producing soft tissues available in tension forces. Ligaments can be modeled as passive spring/dampers and may or may not be included in a generic full body tissue set. Muscles can be the primary soft tissues used in LifeMOD™ to produce tension forces between bone attachments. As described in US Application Publication No. 20110045952: a major objective of a biomechanical simulation tool is to determine the physiologically relevant muscle forces required for a given muscular-skeletal model performing a prescribed kinematic profile. Examples of kinematic profiles include the flexion of elbow or knee. However, kinematic profiles may also be more complex. For example, a kinematic profile may include the motion of walking. For many models and kinematic profiles there are multiple muscle activations that are possible. The goal of the simulation then becomes choosing the set of muscle activations, or muscle recruitment patterns, that best match what is expected for human motion. Some biomechanical simulations of muscular-skeletal systems have used a PID control scheme, e.g. LifeMOD™, for determining muscle forces required to meet a pre-determined kinematic profile. This is done by using a sensor of the muscle kinematics, e.g. muscle length, muscle velocity, or joint angle, which is compared to a target signal. Output of the control system can be a muscle control force that may further be modified to physiological limitations based on maximum force, velocity, etc. Once various models have been created using data for one or more implant component designs and/or orientations, these models can then be queried and/or compared to determine desired and/or undesired features and/or kinematic effects.

Flowcharts and Modeling Techniques

Various embodiments described herein include a variety of techniques and systems for obtaining and/or using bio-motion modeling data to improve the design, selection, manufacture and use of patient-specific implant, tool, jigs and surgical techniques.

What is claimed is:

1. A method of producing a system for treatment of a joint of a patient, the system including an implant and a jig, the method comprising:
    receiving preoperative patient-specific image data of the joint;
    performing a first segmentation of at least a portion of the patient-specific image data to create a first model of one or more surfaces of the joint;
    performing a shape search of a case database of pre-existing implant designs;
    selecting the original implant design from the case database of pre-existing implant designs that is a best fit with the model;
    performing a second segmentation of a select local portion of the patient-specific image data to create a refined model of at least a portion of a surface of the joint;
    designing a personalized jig based, at least in part, on the refined model;
    manufacturing the personalized jig;
    providing an implant based on the original implant design; and
    packaging the personalized jig with the implant.

2. The method of claim 1, wherein providing includes modifying the original implant design to improve fit with the first model.

3. The method of claim 1, wherein providing includes modifying the original implant design based, at least in part, on the refined model.

4. The method of claim 1, wherein the implant is based on the original implant design without modification.

5. The method of claim 1, wherein the select local portion of the patient-specific image data is a subset of the at least a portion of the patient-specific image data upon which the first segmentation was performed.

6. The method of claim 1, further comprising:
    receiving preoperative patient-specific ligament information;
    performing a multibody simulation based, at least in part, on the selected original implant design and the patient-specific ligament information.

7. The method of claim 6, wherein providing includes modifying the original implant design based on results from the multibody simulation.

8. The method of claim 6, wherein the implant is based on the original implant design without modification.

* * * * *